United States Patent
Ohki et al.

(10) Patent No.: US 6,743,776 B2
(45) Date of Patent: Jun. 1, 2004

(54) CYCLOHEXAPEPTIDES HAVING ANTIMICROBIAL ACTIVITY

(75) Inventors: Hidenori Ohki, Takarazuka (JP); Masaki Tomishima, Osaka (JP); Akira Yamada, Fujiidera (JP); Hisashi Takasugi, Sakai (JP)

(73) Assignee: Fujisawa Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/308,237

(22) PCT Filed: Nov. 18, 1997

(86) PCT No.: PCT/JP97/04193
§ 371 (c)(1),
(2), (4) Date: May 21, 1999

(87) PCT Pub. No.: WO98/23637
PCT Pub. Date: Jun. 4, 1998

(65) Prior Publication Data
US 2002/0193560 A1 Dec. 19, 2002

(30) Foreign Application Priority Data
Nov. 25, 1996 (AU) .................................. P03814

(51) Int. Cl.$^7$ .................. A61K 38/12; A61K 38/03
(52) U.S. Cl. ..................... 514/11; 514/9; 530/317; 530/323
(58) Field of Search .................. 530/317; 514/9, 514/11

(56) References Cited

U.S. PATENT DOCUMENTS 6,107,458 A * 8/2000 Ohki et al. .................. 530/317

FOREIGN PATENT DOCUMENTS

| EP | 0 486 011 A2 | * | 5/1992 | ........... A61K/37/02 |
|----|--------------|---|--------|----------------------|
| EP | 0 561 639 A1 | * | 9/1993 | ........... C07K/7/56 |
| EP | 0 644 199 A1 | * | 3/1995 | ........... C07K/7/56 |
| WO | WO96/11210 | * | 4/1996 | ........... C07K/7/56 |

* cited by examiner

Primary Examiner—Michael Borin
(74) Attorney, Agent, or Firm—Oblon, Spivak, McClelland, Maier & Neustadt, P.C.

(57) ABSTRACT

This invention relates to new polypeptide compounds represented by general formula [I]:

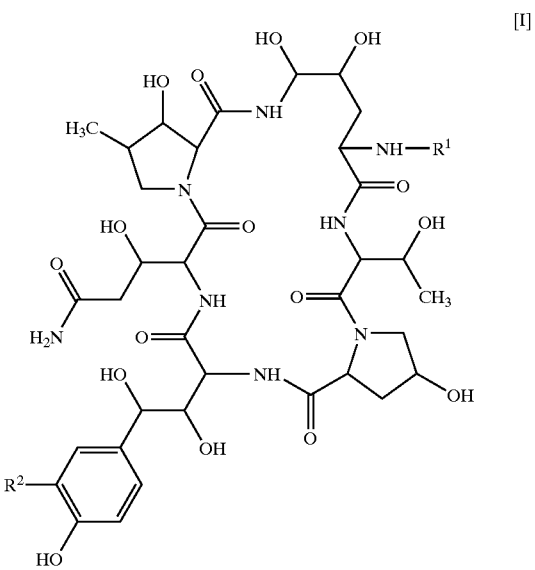

wherein $R^1$ and $R^2$ are as defined in the description and pharmaceutically acceptable salt thereof which have antimicrobial activities (especially, antifungal activities), inhibitory activity on β-1,3-glucan synthase, to process for preparation thereof, to a pharmaceutical composition comprising the same, and to a method for the prophylactic and/or therapeutic treatment of infectious disease including *Pneumocystis carinii* infection (e.g. *Pneumocystis carinii* pneumonia) in a human being or an animal.

34 Claims, No Drawings

CYCLOHEXAPEPTIDES HAVING ANTIMICROBIAL ACTIVITY

TECHNICAL FIELD

The present invention relates to new polypeptide compound and a salt thereof which are useful as a medicament.

BACKGROUND ART

In U.S. Pat. No. 5,376,634, there are disclosed the polypeptide compound and a pharmaceutically acceptable salt thereof, which have antimicrobial activities (especially antifungal activity).

DISCLOSURE OF INVENTION

The present invention relates to new polypeptide compound and a salt thereof.

More particularly, it relates to new polypeptide compound and a salt thereof, which have antimicrobial activities [especially, antifungal activities, in which the fungi may include Aspergillus, Cryptococcus, Candida, Mucor, Actinomyces, Histoplasma, Dermatophyte, Malassezia, Fusarium and the like.], inhibitory activity on β-1,3-glucan synthase, and further which are expected to be useful for the prophylactic and/or therapeutic treatment of Pneumocystis carinii infection (e.g. Pneumocystis carinii pneumonia) in a human being or an animal, to a process for preparation thereof, to a pharmaceutical composition comprising the same, and to a method for the prophylactic and/or therapeutic treatment of infectious diseases including Pneumocystis carinii infection (e.g. Pneumocystis carinii pneumonia) in a human being or an animal.

The object polypeptide compound of the present invention are new and can be represented by the following general formula [I] (SEQ ID No: 1):

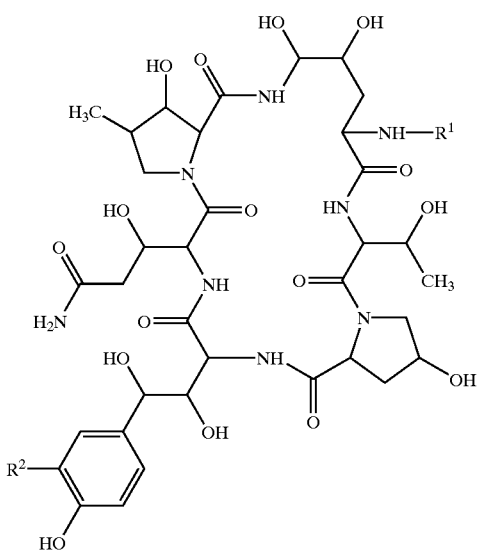

wherein
$R^1$ is aroyl substituted with heterocyclic group which has a suitable substituent selected from the group consisting of
aryl having cyclo(lower)alkyloxy,
aryl having morpholinyl,
aryl having aryloxy(lower)alkoxy,
heterocyclic group having cyclo(lower)alkyl,
heterocyclic group having higher alkyl,
ar(lower)alkyl having lower alkoxy, and
cyclo(lower)alkyl which may have one or more suitable substituent(s);
aroyl substituted with heterocyclic group which has hydroxy and may have additional one or more suitable substituent(s);
aroyl substituted with piperidyl which has aryl having lower alkoxy;
aroyl substituted with thiadiazolyl which has a suitable substituent selected from the group consisting
of aryl having pentyl,
aryl having hexyl,
aryl having methoxy,
aryl having butoxy, and
aryl having higher alkoxy;
aroyl substituted with aryl which has aryl having pentyloxy;
aroyl substituted with piperazinyl which has 3-hexyloxyphenyl;
aroyl substituted with 1,2,3,6-tetrahydropyridyl which may have one or more suitable substituent(s);
aroyl substituted with thienyl which may have one or more suitable substituent(s);
aroyl substituted with furyl which may have one or more suitable substituent(s);
aroyl substituted with heterocyclic(lower)alkyl which may have one or more suitable substituent(s);
aroyl substituted with ar(lower)alkynyl which may have one or more suitable substituent(s);
lower alkanoyl substituted with thiazolyl which may have one or more suitable substituent(s);
aroyl substituted with imidazothiadiazolyl which may have one or more suitable substituent(s);
aroyl substituted with isoxazolyl having halogen which may have one or more suitable substituent(s); or
4-[5-(4-pentyloxyphenyl)isoxazol-3-yl]benzoyl; and
$R^2$ is hydroxy, hydroxysulfonyloxy or lower alkoxy, with proviso that
$R^2$ is not hydroxysulfonyloxy, when $R^1$ is 4-[5-(4-pentyloxyphenyl)isoxazol-3-yl]benzoyl.

The new polypeptide compound [I] and a salt thereof can be prepared by the process as illustrated in the following reaction scheme.

Process 1

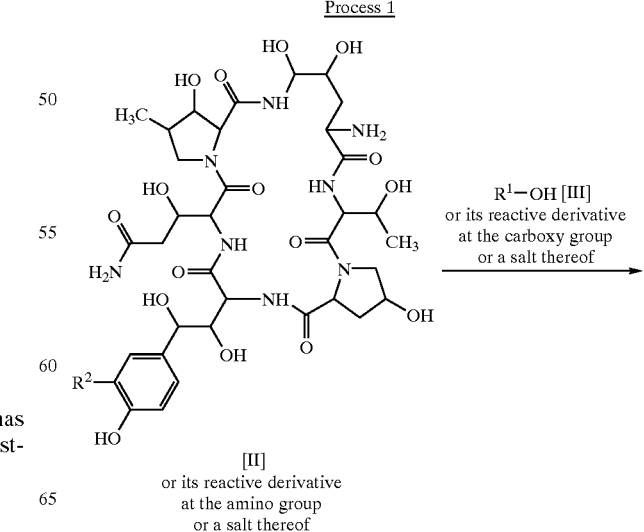

[II]
or its reactive derivative
at the amino group
or a salt thereof

-continued
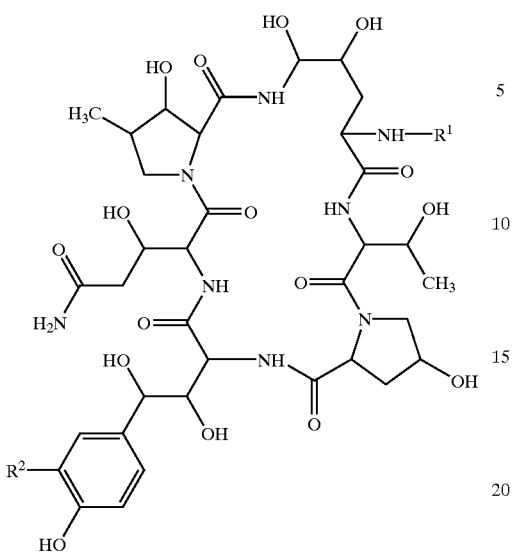
[I]
or a salt thereof
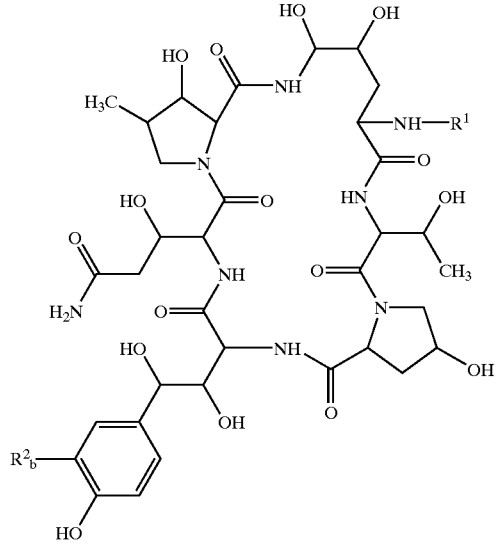
[Ib]
or a salt thereof
Process 2
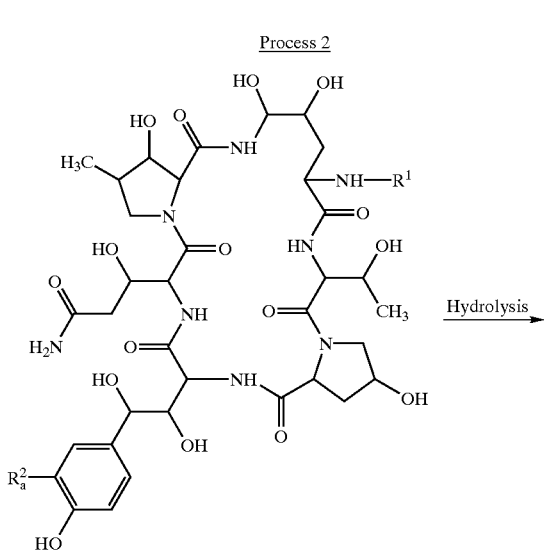
[Ia]
or its reactive derivative
at the sulfonic acid group
or a salt thereof
→ Hydrolysis
Process 3
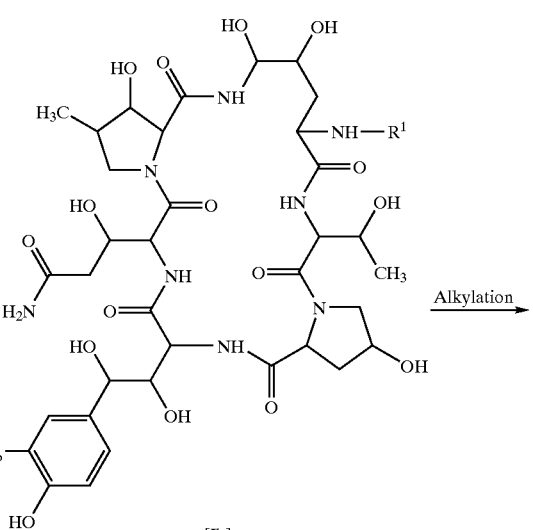
[Ib]
or its reactive derivative
at the hydroxy group
or a salt thereof
→ Alkylation -continued

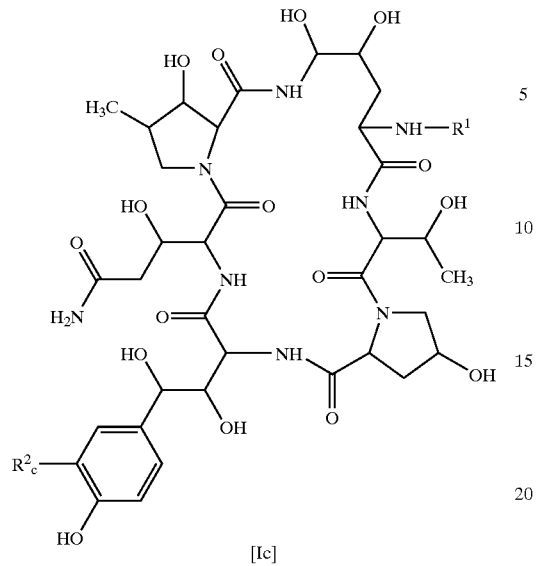

[Ic]
or a salt thereof

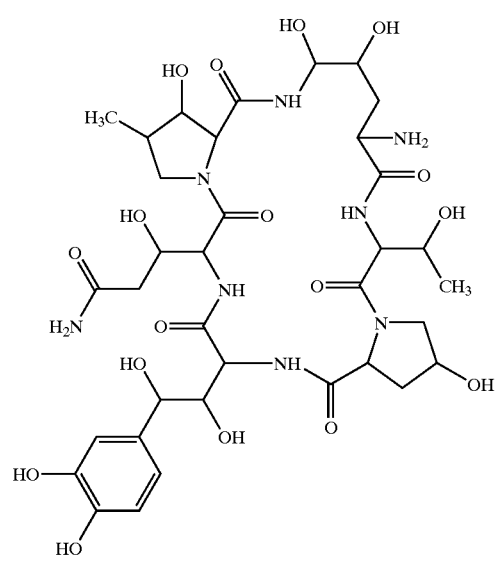

[IIb]
or a salt thereof wherein $R^1$ and $R^2$ are as defined above, $R_a^2$ is hydroxysulfonyloxy, $R_b^2$ is hydroxy or $R_c^2$ is lower alkoxy.

The starting compound [IIb] and [IIc] or a salt thereof are novel and can be prepared by the following schemes.

Process A

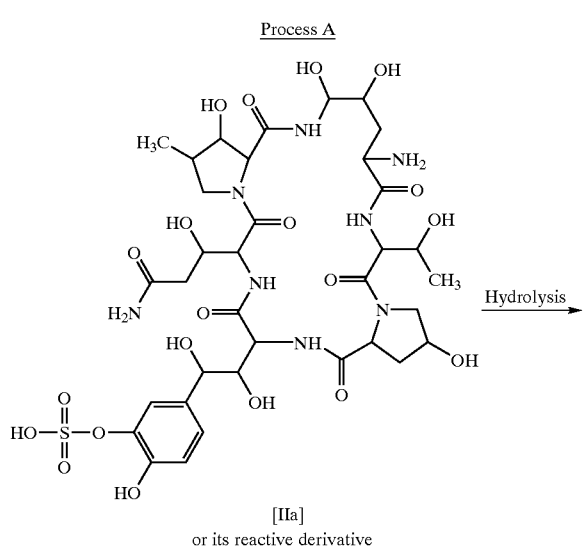

[IIa]
or its reactive derivative
at the sulfonic acid group
or a salt thereof

→ Hydrolysis

Process B

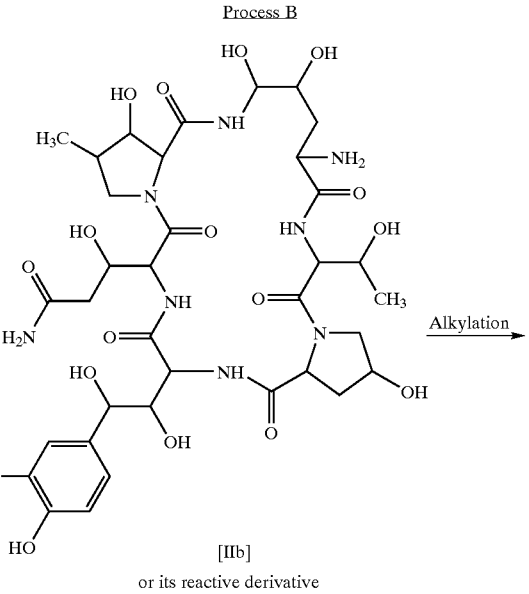

[IIb]
or its reactive derivative
at the hydroxy group
or a salt thereof

→ Alkylation

-continued

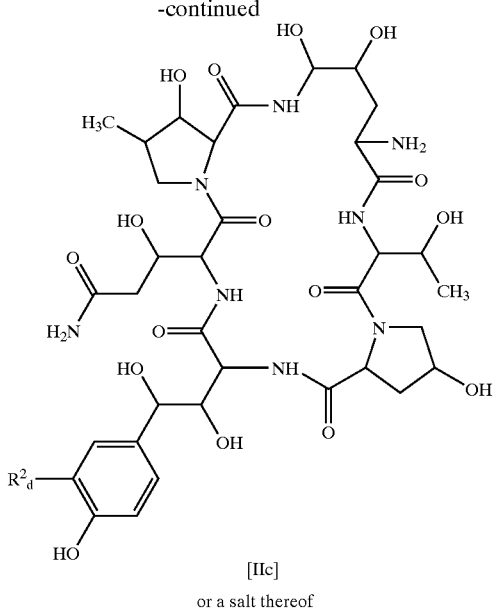

[IIc]

or a salt thereof

Wherein $R_d^2$ is lower alkoxy.

Suitable salts of the object polypeptide compound [I] are pharmaceutically acceptable, conventional non-toxic salts and may include a salt with a base or an acid addition salt such as a salt with an inorganic base, for example, an alkali metal salt (e.g., sodium salt, potassium salt, etc.), an alkaline earth metal salt (e.g., calcium salt, magnesium salt, etc.), an ammonium salt;

a salt with an organic base, for example, an organic amine salt (e.g., triethylamine salt, pyridine salt, picoline salt, ethanolamine salt, triethanolamine salt, dicyclohexylamine salt, N,NI-dibenzylethylenediamine salt, etc.);

an inorganic acid addition salt (e.g., hydrochloride, hydrobromide, sulfate, phosphate, etc.);

an organic carboxylic sulfonic acid addition salt (e.g., formate, acetate, trifluoroacetate, maleate, tartrate, fumarate, methanesulfonate, benzenesulfonate, toluenesulfonate, etc.); a salt with a basic or acidic amino acid (e.g., arginine, aspartic acid, glutamic acid, etc.).

In the above and subsequent descriptions of the present specification, suitable examples and illustration of the various definitions which the present invention intends to include within the scope thereof are explained in detail as follows:

The term "lower" is used to intend a group having 1 to 6 carbon atom(s), unless otherwise provided.

The term "higher" is used to intend a group having 7 to 20 carbon atoms, unless otherwise provided.

Suitable example of "one or more" may be the number of 1 to 6, in which the preferred one may be the number of 1 to 3.

Suitable example of "lower alkanoyl" may include straight or branched one such as formyl, acetyl, 2-methylacetyl, 2,2-dimethylacetyl, propionyl, butyryl, isobutyryl, pentanoyl, 2,2-dimethylpropionyl, hexanoyl, and the like.

Suitable example of "suitable substituent(s)" may include lower alkoxy as mentioned below, higher alkoxy as mentioned below, lower alkyl as mentioned below, higher alkyl as mentioned below, higher alkoxy(lower)alkyl, lower alkoxycarbonyl, oxo, aryl which may have one or more lower alkoxy, aryl which may have one or more higher alkoxy, aryl which may have one or more lower alkyl, aryl which may have one or more higher alkyl, aryl substituted with aryl which may have one or more lower alkoxy, aryl substituted with aryl which may have one or more higher alkoxy, aryl substituted with aryl which may have one or more lower alkyl, aryl substituted with aryl which may have one or more higher alkyl, aroyl which may have one or more lower alkoxy, aroyl which may have one or more higher alkoxy, aroyl which may have one or more lower alkyl, aroyl which may have one or more higher alkyl, heterocyclic group which may have one or more lower alkoxy, heterocyclic group which may have one or more higher alkoxy, aryl having heterocyclic(higher)alkoxy, heterocyclic group which may have aryl having higher alkoxy, heterocyclic group which may have aryl having lower alkoxy(higher)alkoxy, heterocyclic group which may have aryl having lower alkoxy, lower alkoxy(lower)alkyl, halo(lower)alkoxy, lower alkenyloxy, halo(higher)alkoxy, lower alkoxy(higher) alkoxy, aryl which may have one or more lower alkoxy (lower)alkoxy, heterocyclic group, aryl which may have one or more lower alkoxy(higher)alkoxy, aryl which may have one or more higher alkenyloxy, cyclo(lower)alkyl which may have aryl, aryl substituted with heterocyclic group which may have lower alkyl and oxo, cyclo(lower)alkyl which may have one or more lower alkyl, aryl which may have cyclo(lower)alkyl, aryl which may have heterocyclic group, and the like.

Suitable example of "lower alkoxy" may include straight or branched one such as methoxy, ethoxy, propoxy, isopropoxy, butoxy, isobutoxy, tert-butoxy, pentyloxy, tert-pentyloxy, neo-pentyloxy, hexyloxy, isohexyloxy, and the like, in which the preferred one may be methoxy, ethoxy, propoxy, butoxy, pentyloxy, hexyloxy and isohexyloxy.

Suitable example of "higher alkoxy" may include straight or branched one such as heptyloxy, octyloxy, 3,5-dimethyloctyloxy, 3,7-dimethyloctyloxy, nonyloxy, decyloxy, undecyloxy, dodecyloxy, tridecyloxy, tetradecyloxy, hexadecyloxy, heptadecyloxy, octadecyloxy, nonadecyloxy, icosyloxy, and the like, in which the preferred one may be $(C_7-C_{14})$alkoxy, and the more preferred one may be heptyloxy and octyloxy.

Suitable example of "lower alkyl" may include straight or branched one having 1 to 6 carbon atom(s), such as methyl, ethyl, propyl, isopropyl, butyl, isobutyl, sec-butyl, tert-butyl, pentyl, tert-pentyl, neo-pentyl, hexyl, isohexyl, and the like, in which the preferred one may be methyl, pentyl, hexyl and isohexyl.

Suitable example of "higher alkyl" may include straight or branched one having 7 to 20 carbon atoms, such as heptyl, octyl, 3,5-dimethyloctyl, 3,7-dimethyloctyl, nonyl, decyl, undecyl, dodecyl, tridecyl, tetradecyl, pentadecyl, hexadecyl, heptadecyl, octadecyl, nonadecyl, icosyl, and the like, in which the preferred one may be $(C_7-C_{14})$alkyl, and the more preferred one may be heptyl, octyl, nonyl and decyl.

Suitable example of "aryl" and "ar" moiety may include phenyl which may have lower alkyl (e.g., phenyl, mesityl, tolyl, etc.), naphthyl, anthryl, and the like, in which the preferred one may be phenyl and naphthyl.

Suitable example of "aroyl" may include benzoyl, toluoyl, naphthoyl, anthrylcarbonyl, and the like, in which the preferred one may be benzoyl and naphthoyl.

Suitable example of "heterocyclic group" and "heterocyclic" moiety may include unsaturated 3 to 8-membered (more preferably 5 or 6-membered) heteromonocyclic group containing 1 to 4 nitrogen atom(s), for example, pyrrolyl, pyrrolinyl, imidazolyl, pyrazolyl, pyridyl, dihydropyridyl, tetrahydropyridyl, pyrimidyl, pyrazinyl, pyridazinyl, triazolyl (e.g., 4H-1,2,4-triazolyl, 1H-1,2,3-triazolyl, 2H-1,2,3-triazolyl, etc.), tetrazolyl (e.g., 1H-tetrazolyl, 2H-tetrazolyl, etc.), etc.;

saturated 3 to 8-membered (more preferably 5 or 6-membered) heteromonocyclic group containing 1 to 4 nitrogen atom(s), for example, pyrrolidinyl, imidazolidinyl, piperidyl, piperazinyl, etc.;

unsaturated condensed heterocyclic group containing 1 to 4 nitrogen atom(s), for example, indolyl, isoindolyl, indolinyl, indolizinyl, benzimidazolyl, quinolyl, isoquinolyl, indazolyl, benzotriazolyl, etc.;

unsaturated 3 to 8-membered (more preferably 5 or 6-membered) heteromonocyclic group containing 1 to 2 oxygen atom(s) and 1 to 3 nitrogen atom(s), for example, oxazolyl, isoxazolyl, oxadiazolyl (e.g., 1,2,4-oxadiazolyl, 1,3,4-oxadiazolyl, 1,2,5-oxadiazolyl, etc.), etc.;

saturated 3 to 8-membered (more preferably 5 or 6-membered) heteromonocyclic group containing 1 to 2 oxygen atom(s) and 1 to 3 nitrogen atom(s), for example, morpholinyl, sydnonyl, etc.;

unsaturated condensed heterocyclic group containing 1 to 2 oxygen atom(s) and 1 to 3 nitrogen atom(s), for example, benzoxazolyl, benzoxadiazolyl, etc.;

unsaturated 3 to 8-membered (more preferably 5 or 6-membered) heteromonocyclic group containing 1 to 2 sulfur atom(s) and 1 to 3 nitrogen atom(s), for example, thiazolyl, isothiazolyl, thiadiazolyl (e.g., 1,2,3-thiadiazolyl, 1,2,4-thiadiazolyl, 1,3,4-thiadiazolyl, 1,2,5-thiadiazolyl, etc.), dihydrothiazinyl, etc.;

saturated 3 to 8-membered (more preferably 5 or 6-membered) heteromonocyclic group containing 1 to 2 sulfur atom(s) and 1 to 3 nitrogen atom(s), for example, thiazolidinyl, etc.;

unsaturated 3 to 8-membered (more preferably 5 or 6-membered) heteromonocyclic group containing 1 to 2 sulfur atom(s), for example, thienyl, dihydrodithiinyl, dihydrodithionyl, etc.;

unsaturated condensed heterocyclic group containing 1 to 2 sulfur atom(s) and 1 to 3 nitrogen atom(s), for example, benzothiazolyl, benzothiadiazolyl, imidazothiadiazolyl, etc.;

unsaturated 3 to 8-membered (more preferably 5 or 6-membered) heteromonocyclic group containing an oxygen atom, for example, furyl, etc.;

saturated 3 to 8-membered (more preferably 5 or 6-membered) heteromonocyclic group containing an oxygen atom, for example, tetrahydrofuran, tetrahydropyran, etc.;

unsaturated 3 to 8-membered (more preferably 5 or 6-membered) heteromonocyclic group containing an oxygen atom and 1 to 2 sulfur atom(s), for example, dihydrooxathiinyl, etc.;

unsaturated condensed heterocyclic group containing 1 to 2 sulfur atom(s), for example, benzothienyl, benzodithiinyl, etc.;

unsaturated condensed heterocyclic group containing an oxygen atom and 1 to 2 sulfur atom(s), for example, benzoxathiinyl, etc.; and the like.

Suitable example of "halo" may include fluoro, chloro, bromo and iodo.

Suitable example of "lower alkenyloxy" may include vinyloxy, 1-(or 2-)propenyloxy, 1-(or 2- or 3-)butenyloxy, 1-(or 2- or 3- or 4-)pentenyloxy, 1-(or 2- or 3- or 4- or 5-)hexenyloxy, and the like, in which the preferred one may be $(C_2-C_6)$alkenyloxy, and the most preferred one may be 5-hexenyloxy.

Suitable example of "higher alkenyloxy" may include $(C_7-C_{20})$alkenyloxy, in which the preferred one may be 6-heptenyloxy and 7-octenyloxy.

Suitable example of "cyclo(lower)alkyl" may include cyclopropyl, cyclobutyl, cyclopentyl, cyclohexyl, and the like, in which the preferred one may be cyclo$(C_4-C_6)$alkyl, and the most preferred one may be cyclohexyl.

Suitable example of "ar(lower)alkyl" may include benzyl, phenethyl, phenylpropyl, phenylbutyl, phenylpentyl, phenylhexyl, naphthylmethyl, naphthylethyl, naphthylpropyl, naphthylbutyl, naphthylpentyl, naphthylhexyl, and the like, in which the preferred one may be phenyl$(C_1-C_4)$alkyl, and the most preferred one may be phenethyl.

Suitable example of "aroyl" moiety in the term of "aroyl substituted with heterocyclic group which has a suitable substituent selected from the group consisting of aryl having cyclo(lower)alkyloxy, aryl having morpholinyl, aryl having aryloxy(lower)alkoxy, heterocyclic group having cyclo (lower)alkyl, heterocyclic group having higher alkyl, ar(lower)alkyl having lower alkoxy and cyclo(lower)alkyl which may have one or more suitable substituent(s)" can be referred to aforementioned "aroyl", in which the preferred one may be benzoyl.

Suitable example of said "heterocyclic group" moiety can be referred to aforementioned "heterocyclic group", in which the preferred one may be "saturated 3 to 8-membered heteromonocyclic group containing 1 to 4 nitrogen atom(s)" and "unsaturated 3 to 8-membered heteromonocyclic group containing 1 to 2 sulfur atom(s) and 1 to 3 nitrogen atom(s)", and the most preferred one may be piperidyl, piperazinyl and thiadiazolyl.

Suitable example of "aryl having cyclo(lower)alkyloxy" moiety may be cyclopropyloxyphenyl, cyclobutyloxyphenyl, cyclopentyloxyphenyl, cyclohexyloxyphenyl, cyclopentyloxynaphthyl, cyclohexyloxynaphthyl, cyclohexyloxyanthryl, and the like, in which the preferred one may be phenyl having cyclo$(C_4-C_6)$alkyloxy, and the most preferred one may be cyclohexyloxyphenyl.

Suitable example of "aryl having morpholinyl" moiety may be 4-morpholinylphenyl, 3-morpholinylnaphthyl, 2-morpholinylanthryl, and the like, in which the preferred one may be morpholinylphenyl and the most preferred one may be morpholinophenyl.

Suitable example of "aryl having aryloxy(lower)alkoxy" moiety may be phenoxymethoxyphenyl, phenoxyethoxyphenyl, phenoxypropoxyphenyl, phenoxybutoxyphenyl, phenoxypentyloxynaphthyl, phenoxyhexyloxyphenyl, naphthyloxymethoxyphenyl, naphthyloxyethoxynaphthyl, naphthyloxypropoxyphenyl, anthryloxybutoxynaphthyl, and the like, in which the preferred one may be phenoxy$(C_1-C_4)$-alkoxyphenyl, and the most preferred one may be phenoxypropoxyphenyl.

Suitable example of "heterocyclic group having cyclo (lower)alkyl" moiety may be saturated 3 to 8-membered heteromonocyclic group containing 1 to 4 nitrogen atom(s) having cyclopropyl, saturated 3 to 8-membered heteromonocyclic group containing 1 to 4 nitrogen atom(s) having cyclobutyl, saturated 3 to 8-membered heteromonocyclic group containing 1 to 4 nitrogen atom(s) having cyclopentyl, saturated 3 to 8-membered heteromonocyclic group containing 1 to 4 nitrogen atom(s) having cyclohexyl, and the like, in which the preferred one may be piperidyl having cyclo($C_4$–$C_6$)alkyl, and the most preferred one may be piperidyl having cyclohexyl.

Suitable example of "heterocyclic group having higher alkyl" moiety may be saturated 3 to 8-membered heteromonocyclic group containing 1 to 4 nitrogen atom(s) having heptyl, saturated 3 to 8-membered heteromonocyclic group containing 1 to 4 nitrogen atom(s) having octyl, saturated 3 to 8-membered heteromonocyclic group containing 1 to 4 nitrogen atom(s) having nonyl, saturated 3 to 8-membered heteromonocyclic group containing 1 to 4 nitrogen atom(s) having decyl, saturated 3 to 8-membered heteromonocyclic group containing 1 to 4 nitrogen atom(s) having undecyl, saturated 3 to 8-membered heteromonocyclic group containing 1 to 4 nitrogen atom(s) having dodecyl, saturated 3 to 8-membered heteromonocyclic group containing 1 to 4 nitrogen atom(s) having tridecyl, saturated 3 to 8-membered heteromonocyclic group containing 1 to 4 nitrogen atom(s) having tetradecyl, and the like, in which the preferred one may be piperidyl having ($C_7$–$C_{14}$)alkyl, and the most preferred one may be piperidyl having octyl.

Suitable example of "ar(lower)alkyl having lower alkoxy" moiety may be methoxybenzyl, ethoxybenzyl, propoxybenzyl, butoxybenzyl, pentyloxybenzyl, pentyloxyphenethyl, hexyloxyphenethyl, pentyloxyphenylpropyl, hexyloxyphenylbutyl, pentyloxyphenylpentyl, hexyloxyphenylhexyl, and the like, in which the preferred one may be phenethyl having ($C_4$–$C_6$) alkoxy, and the most preferred one may be hexyloxyphenethyl.

Suitable example of "suitable substituent(s)" moiety in the term of "cyclo(lower)alkyl which may have one or more suitable substituent(s)" can be referred to aforementioned "suitable substituent(s)", in which the preferred one may be cyclo(lower)alkyl, and the more preferred one may be cyclo($C_4$–$C_6$)alkyl, and the most preferred one may be cyclohexyl.

Suitable example of "cyclo(lower)alkyl which may have one or more suitable substituent(s)" may be cyclo(lower) alkyl which may have cyclo(lower)alkyl or lower alkyl, in which the preferred one may be cyclo($C_4$–$C_6$)alkyl having cyclo($C_4$–$C_6$)-alkyl or ($C_4$–$C_6$)alkyl, and the most preferred one may be cyclohexyl having cyclohexyl or cyclohexyl having pentyl.

Suitable example of "aroyl" moiety in the term of "aroyl substituted with heterocyclic group which has hydroxy and may have additional one or more suitable substituent(s)" can be referred to aforementioned "aroyl", in which the preferred one may be benzoyl.

Suitable example of "heterocyclic group " moiety in the term of "aroyl substituted with heterocyclic group which has hydroxy and may have additional one or more suitable substituent(s)" can be referred to aforementioned "heterocyclic group", in which the preferred one may be saturated 3 to 8-membered heterocyclic group containing 1 to 4 nitrogen atom(s), and the most preferred one may be piperidyl.

Suitable example of "suitable substituent(s)" moiety in said group may be aryl having lower alkoxy such as methoxyphenyl, ethoxyphenyl, propoxyphenyl, butoxyphenyl, pentyloxyphenyl, hexyloxyphenyl, pentyloxynaphthyl, hexyloxynaphthyl, hexyloxyanthryl, and the like, in which the preferred one may be phenyl having ($C_4$–$C_6$)alkoxy, and the most preferred one may be hexyloxyphenyl.

Suitable example of "aroyl" moiety in the term of "aroyl substituted with piperidyl which has aryl having lower alkoxy" can be referred to aforementioned "aroyl", in which the preferred one may be benzoyl.

Suitable example of "aryl" moiety in the term of "aroyl substituted with piperidyl which has aryl having lower alkoxy" can be referred to aforementioned "aryl", in which the preferred one may be phenyl.

Suitable example of "aroyl substituted with piperidyl which has aryl having lower alkoxy" may be benzoyl substituted with piperidyl which has hexyloxyphenyl, naphthoyl substituted with piperidyl which has hexyloxynaphthyl, and the like, in which the preferred one may be benzoyl substituted with piperidyl which has phenyl having ($C_4$–$C_6$)alkoxy, and the most preferred one may be benzoyl substituted with piperidyl which has hexyloxyphenyl.

Suitable example of "aroyl" moiety in the term of "aroyl substituted with thiadiazolyl which has a suitable substituent selected from the group consisting of aryl having pentyl, aryl having hexyl, aryl having methoxy, aryl having butoxy and aryl having higher alkoxy" can be referred to aforementioned "aroyl", in which the preferred one may be benzoyl.

Suitable example of "aryl" moiety in the term of "aryl having pentyl, aryl having hexyl, aryl having methoxy, aryl having butoxy and aryl having higher alkoxy" can be referred to aforementioned "aryl", in which the preferred one may be phenyl.

Suitable example of "aroyl substituted with thiadiazolyl which has a suitable substituent selected from the group consisting of aryl having pentyl, aryl having hexyl, aryl having methoxy, aryl having butoxy and aryl having higher aloxy" may be benzoyl substituted with thiadiazolyl which has a suitable substituent selected from the group consisting of pentylphenyl, hexylphenyl, methoxyphenyl, butoxyphenyl and heptyloxyphenyl.

Suitable example of "aroyl" moiety in the term of "aroyl substituted with aryl which has aryl having pentyloxy" can be referred to aforementioned "aroyl", in which the preferred one may be benzoyl.

Suitable example of "aryl" moiety in the term of "aroyl substituted with aryl which has aryl having pentyloxy" can be referred to aforementioned "aryl", in which the preferred one may e phenyl.

Suitable example of "aroyl substituted with aryl which has aryl having pentyloxyl" may be benzoyl substituted with phenyl which has pentyloxyphenyl, naphthoyl substituted with naphthyl which has pentyloxyphenyl, anthrylcarbonyl substituted with phenyl which has pentyloxynaphthyl, and the like, in which the preferred one may be benzoyl substituted with phenyl which has pentyloxyphenyl.

Suitable example of "aroyl" in the term of "aroyl substituted with piperazinyl which has 3-hexyloxyphenyl" can be referred to aforementioned "aroyl", in which the preferred one may be benzoyl.

Suitable example of "aroyl substituted with piperazinyl which has 3-hexyloxyphenyl" may be benzoyl substituted with piperazinyl which has 3-hexyloxyphenyl.

Suitable example of "aroyl" moiety in the term of "aroyl substituted with 1,2,3,6-tetrahydropyridyl which may have one or more suitable substituent(s)" can be referred to aforementioned "aroyl" in which the preferred one may be benzoyl.

Suitable example of "suitable substituent(s)" moiety in the term of "aroyl substituted with 1,2,3,6-tetrahydropyridyl which may have one or more suitable substituent(s)" can be referred to aforementioned "suitable substituent(s)", in which the preferred one may be aryl which may have one or more lower alkoxy, and the more preferred one may be phenyl which may have a ($C_4$–$C_6$)alkoxy, and the most preferred one may be hexyloxyphenyl.

Suitable example of "aroyl" moiety in the term of "aroyl substituted with thienyl which may have one or more suitable substituent(s)" can be referred to aforementioned "aroyl", in which the preferred one may be benzoyl.

Suitable example of "suitable substituent(s)" in the term of "aroyl substituted with thienyl which may have one or more suitable substituent(s)" can be referred to aforementioned "suitable substituent(s)", in which the preferred one may be aryl which may have one or more lower alkoxy, and the more preferred one may be phenyl which may have a ($C_4$–$C_6$)alkoxy, and the most preferred one may be pentyloxyphenyl.

Suitable example of "aroyl" moiety in the term of "aroyl substituted with furyl which may have one or more suitable substituent(s)" can be referred to aforementioned "aroyl", in which the preferred one may be benzoyl.

Suitable example of "suitable substituent(s)" moiety in the term of "aroyl substituted with furyl which may have one or more suitable substituent(s)" can be referred to aforementioned "suitable substituent(s)", in which the preferred one may be aryl which may have one or more lower alkoxy, and the more preferred one may be phenyl which may have a ($C_4$–$C_6$)alkoxy, and the most preferred one may be pentyloxyphenyl.

Suitable example of "aroyl" moiety in the term of "aroyl substituted with heterocyclic(lower)alkyl which may have one or more suitable substituent(s)" can be referred to aforementioned "aroyl", in which the preferred one may be benzoyl.

Suitable example of "heterocyclic" moiety in the term of "aroyl substituted with heterocyclic(lower)alkyl which may have one or more suitable substituent(s)" can be referred to aforementioned "heterocyclic" moiety, in which the preferred one may be saturated 3 to 8-membered heteromonocyclic group containing 1 to 4 nitrogen atom(s), and the most preferred one may be piperazinyl.

Suitable example of "suitable substituent(s)" moiety in the term of "aroyl substituted with heterocyclic(lower)alkyl which may have one or more suitable substituent(s)" can be referred to aforementioned "suitable substituent(s)", in which the preferred one may be aryl which may have cyclo(lower)alkyl, and the more preferred one may be phenyl which has cyclo($C_4$–$C_6$)alkyl, and the most preferred one may be cyclohexylphenyl.

Suitable example of "aroyl substituted with heterocyclic (lower)alkyl which may have one or more suitable substituent(s)" may be benzoyl substituted with heterocyclic ($C_1$–$C_6$)alkyl which may have phenyl which may have cyclo($C_3$–$C_6$)alkyl, in which the preferred one may be benzoyl substituted with ($C_1$–$C_4$)alkyl having saturated 3 to 8-membered heteromonocyclic group containing 1 to 4 nitrogen atom(s) which may have phenyl which has cyclo ($C_4$–$C_6$)alkyl, and the most preferred one may be benzoyl substituted with piperazinylmethyl which has phenyl having cyclohexyl or benzoyl substituted with piperazinylethyl which has phenyl having cyclohexyl.

Suitable example of "aroyl" moiety in the term of "aroyl substituted with ar(lower)alkynyl which may have one or more suitable substituent(s)" can be referred to aforementioned "aroyl", in which the preferred one may be benzoyl.

Suitable example of "ar(lower)alkynyl" moiety in the term of "aroyl substituted with ar(lower)alkynyl which may have one or more suitable substituent(s)" may be phenylethynyl, phenylpropynyl, phenylbutynyl, naphthylpentynyl, phenylhexynyl, naphthylethynyl, anthrylpropynyl, and the like, in which the preferred one may be phenyl($C_2$–$C_4$)alkynyl, and the most preferred one may be phenylethynyl.

Suitable example of "suitable substituent(s)" moiety in the term of "aroyl substituted with ar(lower)alkynyl which may have one or more suitable substituent(s)" can be referred to aforementioned "suitable substituent(s)", in which the preferred one may be lower alkoxy, and the more preferred one may be ($C_4$–$C_6$)alkoxy, and the most preferred one may be pentyloxy.

Suitable example of "aroyl substituted with ar(lower)alkynyl which may have one or more suitable substituent(s)" may be benzoyl substituted with phenyl(lower)alkynyl which may have lower alkoxy, in which the preferred one may be benzoyl substituted with phenyl-($C_2$–$C_4$)alkynyl which has ($C_4$–$C_6$)alkoxy, and the most preferred one may be benzoyl substituted with phenylethynyl which has pentyloxy.

Suitable example of "lower alkanoyl" moiety in the term of "lower alkanoyl substituted with thiazolyl which may have one or more suitable substituent(s)" can be referred to aforementioned "lower alkanoyl", in which the preferred one may be ($C_1$–$C_4$)alkanoyl, and the most preferred one may be formyl.

Suitable example of "suitable substituent(s)" in the term of "lower alkanoyl substituted with thiazolyl which may have one or more suitable substituent(s)" can be referred to aforementioned "suitable substituent(s)", in which the preferred one may be aryl substituted with aryl having lower alkoxy, and the more preferred one may be phenyl substituted with phenyl having ($C_4$–$C_6$)alkoxy, and the most preferred one may be phenyl substituted with pentyloxyphenyl.

Suitable example of "aroyl" moiety in the term of "aroyl substituted with imidazothiadiazolyl which may have one or more suitable substituent(s)" can be referred to aforementioned "aroyl", in which the preferred one may be benzoyl.

Suitable example of "suitable substituent(s)" moiety in the term of "aroyl substituted with imidazothiadiazolyl which may have one or more suitable substituent(s)" can be referred to aforementioned "suitable substituent(s)", in which the preferred one may be aryl which may have one or more lower alkoxy or aryl substituted with aryl, and the more preferred one may be aryl having ($C_2$–$C_6$)alkoxy or aryl having phenyl, and the most preferred one may be phenyl having pentyloxy, phenyl having ethoxy or phenyl having phenyl.

Suitable example of "aroyl substituted with imidazothiadiazolyl which may have one or more suitable substituent (s)" may be benzoyl substituted with imidazothiadiazolyl which has phenyl having ($C_2$–$C_6$)alkoxy or benzoyl substituted with imidazothiadiazolyl which has aryl having phenyl, and the most preferred one may be benzoyl substituted with imidazothiadiazolyl which has phenyl having pentyloxy, benzoyl substituted with imidazothiadiazolyl which has phenyl having ethoxy or benzoyl substituted with imidazothiadiazolyl which has phenyl having phenyl.

Suitable example of "aroyl" moiety in the term of "aroyl substituted with isoxazolyl having halogen which may have one or more suitable substituent(s)" can be referred to aforementioned "aroyl", in which the preferred one may be benzoyl.

Suitable example of "suitable substituent(s)" moiety in the term of "aroyl substituted with isoxazolyl having halogen which may have one or more suitable substituent(s)" can be referred to aforementioned "suitable substituent(s)", in which the preferred one may be aryl which may have lower alkoxy, the preferred one may be phenyl which has $(C_4-C_6)$-alkoxy, and the most preferred one may be phenyl having pentyloxy.

Suitable example of "aroyl substituted with isoxazolyl having halogen which may have one or more suitable substituent(s)" may be benzoyl substituted with isoxazolyl having chloro which has phenyl having $(C_4-C_6)$alkoxy, and the most preferred one may be benzoyl substituted with isoxazolyl having chloro which has phenyl having pentyloxy.

The processes for preparing the object polypeptide compound [I] and the starting compounds [IIb] and [IIc] or a salt thereof of the present invention are explained in detail in the following.

Process 1

The object polypeptide compound [I] or a salt thereof can be prepared by reacting the compound [II] or its reactive derivative at the amino group or a salt thereof with the compound [III] or its reactive derivative at the carboxy group or a salt thereof.

Suitable reactive derivative at the carboxy group of the compound [III] may include an acid halide, an acid anhydride, an activated amide, an activated ester, and the like. Suitable examples of the reactive derivatives may be an acid chloride; an acid azide; a mixed acid anhydride with an acid such as substituted phosphoric acid [e.g., dialkylphosphoric acid, phenylphosphoric acid, diphenylphosphoric acid, dibenzylphosphoric acid, halogenated phosphoric acid, etc.], dialkylphosphorous acid, sulfurous acid, thiosulfuric acid, sulfuric acid, sulfonic acid [e.g., methanesulfonic acid, etc.], aliphatic carboxylic acid [e.g., acetic acid, propionic acid, butyric acid, isobutyric acid, pivaric acid, pentanoic acid, isopentanoic acid, 2-ethylbutyric acid, trichloroacetic acid, etc.]; or aromatic carboxylic acid [e.g., benzoic acid, etc.]; a symmetrical acid anhydride; an activated amide with imidazole, 4-substituted imidazole, dimethylpyrazole, triazole, tetrazole or 1-hydroxy-1H-benzotriazole; or an activated ester [e.g., cyanomethyl ester, methoxymethyl ester, dimethyliminomethyl

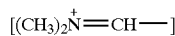

ester, vinyl ester, propargyl ester, p-nitrophenyl ester, 2,4-dinitrophenyl ester, trichlorophenyl ester, pentachloropentyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.], or an ester with a N-hydroxy compound [e.g. N,N-dimethylhydroxylamine, 1-hydroxy-2-(1H)-pyridone, N-hydroxysuccinimide, N-hydroxyphthalimide, 1-hydroxy-1H-benzotriazole, etc.], and the like. These reactive derivatives can optionally be selected from them according to the mind of the compound [III] to be used.

Suitable salts of the compound [III] and its reactive derivative can be referred to the ones as exemplified for the object polypeptide compound [I].

The reaction is usually carried out in a conventional solvent such as water, alcohol [e.g., methanol, ethanol, etc.], acetone, dioxane, acetonitrile, chloroform, methylene chloride, ethylene chloride, tetrahydrofuran, ethyl acetate, N,N-dimethylformamide, pyridine or any other organic solvent which does not adversely influence the reaction. These conventional solvent may also be used in a mixture with water.

In this reaction, when the compound [III] is used in a free acid form or its salt form, the reaction is preferably carried out in the presence of a conventional condensing agent such as N,N'-dicyclohexylcarbodiimide; N-cyclohexyl-N-morpholinoethylcarbodiimide; N-cyclohexyl-N'-(4-diethylaminocyclohexyl)carbodiimide; N,N'-diethylcarbodiimide; N,N'-diisopropylcarbodiimide; N-ethyl-N'-(3-dimethylaminopropyl)carbodiimide; N,N-carbonylbis-(2-methylimidazole); pentamethyleneketene-N-cyclohexylimine; diphenylketene-N-cyclohexylimine; ethoxyacetylene; 1-alkoxy-2-chloroethylene; trialkyl phosphite; ethyl polyphosphate; isopropyl polyphosphate; phosphorus oxychloride (phosphoryl chloride); phosphorus trichloride; thionyl chloride; oxalyl chloride; lower alkyl haloformate [e.g., ethyl chloroformate, isopropyl chloroformate, etc.]; triphenylphosphine; 2-ethyl-7-hydroxybenzisoxazolium salt; 2-ethyl-5-(m-sulfophenyl) isoxazolium hydroxide intramolecular salt; 1-(p-chlorobenzenesulfonyloxy)-6-chloro-1H-benzotriazole; so-called Vilsmeier reagent prepared by the reaction of N,N-dimethylformamide with thionyl chloride, phosgene, trichloromethyl chloroformate, phosphorous oxychloride, methanesulfonyl chloride, etc.; or the like.

The reaction may also be carried out in the presence of an inorganic or organic base such as an alkali metal carbonate, alkali metal bicarbonate, tri(lower)alkylamine, pyridine, di(lower)alkylaminopyridine (e.g., 4-dimethylaminopyridine, etc.), N-(lower)alkylmorpholine, N,N-di(lower)alkylbenzylamine, or the like.

The reaction temperature is not critical, and the reaction is usually carried out under cooling to warming.

The starting compound [IIa] is a known compound. It can be prepared by fermentation and synthetic processes disclosed in EP 0462531 A2.

A culture of Coleophoma sp. F-11899, which is used in said fermentation process, has been deposited with National Institute of Bioscience and Human-Technology Agency of Industrial Science and Technology (former name Fermentation Research Institute Agency of Industrial Science and Technology) (1–3, Higashi 1-chome, Tsukuba-shi, IBARAKI 305, JAPAN) on Oct. 26, 1989 under the number of FERM BP-2635.

Process 2

The compound [Ib] or a salt thereof can be prepared by subjecting the compound [Ia] or its reactive derivative at the sulfonic acid group or a salt thereof to hydrolysis reaction of the sulfonic acid group.

The hydrolysis is preferably carried out in the presence of a base or an acid including Lewis acid.

Suitable base may include an inorganic base and an organic base such as an alkali metal [e.g., sodium, potassium, etc.], an alkaline earth metal [e.g., magnesium, calcium, etc.], the hydroxide or carbonate or hydrogencarbonate thereof, trialkylamine [e.g., trimethylamine, triethylamine, etc.], picoline, 1,5-diazabicyclo[4.3.0]-non-5-ene, or the like.

Suitable acid may include an organic acid [e.g., formic acid, acetic acid, propionic acid, trichloroacetic acid, trifluoroacetic acid, etc.], and an inorganic acid [e.g., hydrochloric acid, hydrobromic acid, sulfuric acid, hydrogen, chloride, hydrogen bromide, etc.].

The elimination using Lewis acid such as trihaloacetic acid [e.g., trichloroacetic acid, trifluoroacetic acid, etc.], or the like is preferably carried out in the presence of cation trapping agents [e.g., anisole, phenol, etc.].

The reaction is usually carried out in a conventional solvent such as water, alcohol [e.g., methanol, ethanol, isopropyl alcohol, etc.], tetrahydrofuran, dioxane, toluene, methylene chloride, ethylene dichloride, chloroform, N,N-dimethylformamide, N,N-dimethylacetamide or any other organic solvent which do not adversely affect the reaction, or the mixture thereof.

The reaction temperature is not critical and the reaction is usually carried out under cooling to warming.

Process 3

The compound [Ic] or a salt thereof can be prepared by subjecting the compound [Ib] or its reactive derivative at the hydroxy group or a salt thereof with the diazo compound [e.g., diazomethane, phenyldiazomethane, diphenyldiazomethane, β-diazopropionic acid, etc.] or a salt thereof to alkylation reaction of the hydroxy group.

This reaction is usually carried out in the solvent such as water, alcohol [e.g., methanol, ethanol, etc.], benzene, N,N-dimethylformamide, tetrahydrofuran, toluene, methylene chloride, ethylene dichloride, chloroform, dioxane, diethyl ether, acetonitrile or any other solvents which do not adversely affect the reaction, or the mixture thereof.

The reaction temperature is not critical and the reaction is usually carried out under cooling to heating.

The reaction may be usually carried out in the presence of an acid including Lewis acid.

Suitable acid may include an organic acid [e.g. formic acid, acetic acid, propionic acid, trichloroacetic acid, trifluoroacetic acid, etc.] and an inorganic acid [e.g. hydrochloric acid, hydrobromic acid, sulfuric acid, hydrogen chloride, hydrogen bromide, zinc halide (e.g., zinc chloride, zinc bromide, etc.), etc.] and the like.

The reaction may be also carried out in the presence of an inorganic or an organic base such as an alkali metal [e.g., sodium, potassium, etc.], an alkali metal hydroxide [e.g., sodium hydroxide, potassium, hydroxide, etc.], an alkali metal hydrogencarbonate [e.g., sodium hydrogencarbonate, potassium hydrogencarbonate, etc.], alkali metal carbonate [e.g., sodium carbonate, potassium carbonate, etc.], tri(lower)alkylamine [e.g., trimethylamine, triethylamine, diisopropylethylamine, etc.], alkali metal hydride [e.g., sodium hydride, etc.], alkali metal (lower)alkoxide [e.g. sodium methoxide, sodium ethoxide, etc.], pyridine, lutidine, picoline, dimethylaminopyridine, N-(lower)alkylmorpholine, N,N-di(lower)alkylbenzylamine, N,N-di(lower)alkylaniline or the like.

When the base, the acid and/or the starting compound are in liquid, they can be used also as a solvent.

Process A

The starting compound [IIb] or a salt thereof can be prepared by subjecting the compound [IIa] or its reactive derivative at the sulfonic acid group or a salt thereof to hydrolysis reaction of the sulfonic acid group.

This reaction can be carried out in a similar manner to that of Process 2 mentioned in the above, and therefore the reaction mode and reaction conditions [e.g., base, acid, catalyst, solvent, reaction temperature, etc.] of this reaction are to be referred to those as explained in Process 2.

Process B

The starting compound [IIc] or a salt thereof can be prepared by subjecting the compound [IIb] or its reactive derivative at the hydroxy group or a salt thereof with the diazo compound [e.g., diazomethane, phenyldiazomethane, diphenyldiazomethane, β-diazopropionic acid, etc.] or a salt thereof to alkylation reaction of the hydroxy group.

This reaction can be carried out in a similar manner to that of Process 3 mentioned in the above, and therefore the reaction mode and reaction conditions [e.g., base, acid, catalyst, solvent, reaction temperature, etc.] of this reaction are to be referred to those as explained in Process 3.

The compounds obtained by the above Processes 1 to 3 and Processes A and B can be isolated and purified by a conventional method such as pulverization, recrystallization, column-chromatography, high-performance liquid chromatography (HPLC), reprecipitation, or the like.

The compounds obtained by the above Processes 1 to 3 and Processes A and B may be obtained as its hydrate, and its hydrate is included within the scope of this invention.

It is to be noted that each of the object compound [I] may include one or more stereoisomer such as optical isomer(s) and geometrical isomer(s) due to asymmetric carbon atom(s) and double bond(s) and all such isomers and mixture thereof are included within the scope of this invention.

Biological Property of the Polypeptide Compound [I] of the Present Invention

In order to show the usefulness of the polypeptide compound [I] of the present invention, the biological data of the representative compound is explained in the following.

Test (Antimicrobial Activity)

In vitro antimicrobial activity of the compound of Example 15 disclosed later was determined by the two-fold agar-plate dilution method as described below.

Test Method

One loopful of an overnight culture of each test microorganism in Sabouraud broth containing 2% Glucose ($10^5$ viable cells per ml) was streaked on yeast nitrogen base dextrose agar (YNBDA) containing graded concentrations of the object polypeptide compound [I], and the minimal inhibitory concentration (MIC) was expressed in terms of μg/ml after incubation at 30° C. for 24 hours.

Test Result

| | MIC (μg/ml) | |
| --- | --- | --- |
| Test compound<br>Test organism | | The object compound<br>of Example 15 |
| candida albicans FP-633 | | 0.1 |

From the test result, it is realized that the object polypeptide compound [I] of the present invention has an antimicrobial activity (especially, antifungal activity).

The pharmaceutical composition of the present invention can be used in the form of a pharmaceutical preparation, for example, in solid, semisolid or liquid form, which contains the object polypeptide compound [I] or a pharmaceutically acceptable salt thereof, as an active ingredient in admixture with an organic or inorganic carrier or excipient which is suitable for rectal; pulmonary (nasal or buccal inhalation); ocular; external (topical); oral administration; parenteral (including subcutaneous, intravenous and intramuscular) administrations; insufflation (including aerosols from metered dose inhalator); nebulizer; or dry powder inhalator.

The active ingredient may be compounded, for example, with the usual non-toxic, pharmaceutically acceptable carriers in a solid form such as granules, tablets, dragees, pellets, troches, capsules, or suppositories; creams; ointments; aerosols; powders for insufflation; in a liquid form such as solutions, emulsions, or suspensions for injection; ingestion; eye drops; and any other form suitable for use. And, if necessary, there may be included in the above preparation auxiliary substance such as stabilizing, thickening, wetting, emulsifying and coloring agents; perfumes or buffer; or any other commonly may be used as additives.

The object polypeptide compound [I] or a pharmaceutically acceptable salt thereof is/are included in the pharmaceutical composition in an amount sufficient to produce the desired antimicrobial effect upon the process or condition of diseases.

For applying the composition to human, it is preferable to apply it by intravenous, intramuscular, pulmonary, oral administration, or insufflation. While the dosage of therapeutically effective amount of the object polypeptide compound [I] varies form and also depends upon the age and condition of each individual patient to be treated, in the case of intravenous administration, a daily dose of 0.01–20 mg of the object polypeptide compound [I] per kg weight of human being in the case of intramuscular administration, a daily dose of 0.1–20 mg of the object polypeptide compound [I] per kg weight of human being, in case of oral administration, a daily dose of 0.5–50 mg of the object polypeptide compound [I] per kg weight of human being is generally given for treating or preventing infectious diseases.

Especially in case of the treatment of prevention of *Pneumocystis carinii* infection, the followings are to be noted.

For administration by inhalation, the compounds of the present invention are conveniently delivered in the form of an aerosol spray presentation from pressurized as powders which may be formulated and the powder compositions may be inhaled with the aid of an insufflation powder inhaler device. The preferred delivery system for inhalation is a metered dose inhalation aerosol, which may be formulated as a suspension or solution of compound in suitable propellants such as fluorocarbons or hydrocarbons.

Because of desirability to directly treat lung and bronchi, aerosol administration is a preferred method of administration. Insufflation is also a desirable method, especially where infection may have spread to ears and other body cavities.

Alternatively, parenteral administration may be employed using drip intravenous administration.

The following Preparations and Examples are given for the purpose of illustrating the present invention in more detail.

Preparation 1

To a suspension of sodium hydride (60% suspension in mineral oil) (1.18 g) in dimethylformamide (25 ml) was added 1-acetyl-4-(4-hydroxyphenyl)piperazine (5 g) and bromocyclohexane (5.59 ml) and stirred for 1 hour at 100° C. The reaction mixture was added to a mixture of water and ethyl acetate. The organic layer was taken and dried over magnesium sulfate. The magnesium sulfate was filtered off, and the filtrate was evaporated under reduced pressure to give 1-acetyl-4-(4-cyclohexyloxyphenyl)piperazine (0.92 g).

Preparation 2

A solution of 3-[2-(4-morpholinophenylamino)ethyl]-2-oxazolidone (5 g) in 30% hydrobromic acid in acetic acid (35 ml) was stirred for 24 hours at ambient temperature. The reaction mixture was pulverized with diisopropyl ether. The precipitate was collected by filtration and added to ethanol (35 ml). The solution was refluxed for 8 hours and pulverized with diisopropyl ether. The precipitate was collected by filtration to give 1-(4-morpholinophenyl)-piperazine dihydrobromide (7.42 g).

IR (KBr): 1608.3, 1521.6, 1259.3, 889.0 cm$^{-1}$

NMR (D$_2$O, δ): 3.3–3.8 (12H, m), 4.1–4.2 (4H, m), 7.24 (2H, d, J=9.3 Hz), 7.58 (2H, d, J=9.3 Hz)

APCI-MASS: m/z=248 (M+H)$^+$

Preparation 3

To a solution of 1-tert-butoxycarbonyl-4-(4-hexyloxyphenyl)-4-hydroxypiperidine (6.856 g) in dichloromethane (34 ml) was added trifluoroacetic acid (17 ml) and stirred for 30 minutes at 4° C. The reaction mixture was adjusted to pH 12 with 2M aqueous NaOH. The organic layer was separated, washed with water and dried over magnesium sulfate and evaporated under reduced pressure to give 4-(4-hexyloxyphenyl)-1,2,3,6-tetrahydropiridine (3.59 g)

IR (KBr): 3263.0, 1604.5, 1511.9, 1251.6, 842.7 cm$^{-1}$

NMR (CDCl$_3$, δ): 0.90 (3H, t, J=6.5 Hz), 1.2–1.6 (6H, m), 1.6–1.9 (3H, m), 2.3–2.5 (2H, m), 3.10 (2H, t, J=5.7 Hz), 3.4–3.6 (2H, m), 3.95 (2H, t, J=6.5 Hz), 6.0–6.1 (1H, m), 6.85 (2H, d, J=8.9 Hz), 7.30 (2H, d, J=8.9 Hz)

APCI-MASS: m/z=260 (M+H)$^+$

Preparation 4

A solution of 4-[4-(3-hydroxyphenyl)piperazin-1-yl]benzoic acid dihydrobromide (2.396 g) in a mixture of 5% NaOH aq. (16.7 ml) and dimethylsulfoxide (33.3 ml) was stirred for 30 minutes at 80° C. Then, 1-bromohexane (0.88 ml) was added thereto and stirred for 8 hours at 80° C. The reaction mixture was added to water and adjusted to pH 2.0 with 1N HCl. The produced precipitate was collected by filtration and dried under reduced pressure to give 4-[4-(3-hexyloxyphenyl)piperazin-1-yl]benzoic acid hydrochloride (3.74 g).

IR (KBr): 1670.1, 1602.6, 1236.1, 1189.9 cm$^{-1}$

NMR (DMSO-d$_6$, δ): 0.88 (3H t, J=6.9 Hz), 1.2–1.5 (6H, m), 1.6–1.8 (2H, m), 3.2–3.5 (8H, m), 3.93 (2H, t, J=6.4 Hz), 6.38 (1H, d, J=8.0 Hz), 6.49 (1H, s), 6.55 (1H, d, J=8.0 Hz), 7.02 (2H, d, J=9.0 Hz), 7.12 (1H, dd, J=8.0 Hz), 7.79 (2H, d, J=9.0 Hz)

APCI-MASS: m/z=383 (M+H)$^+$

Preparation 5

To a solution of methyl 4-[5-[N-(tert-butoxycarbonyl)-piperidin-4-yl]-1,3,4-thiadiazol-2-yl]benzoate (1.28 g) in dichloromethane (12 ml) was added trifluoroacetic acid (25 ml) at 0° C. and the reaction mixture was stirred for 1 hour at room temperature. The solvents were removed under reduced pressure. The precipitate was triturated with diisopropyl ether, collected by filtration, washed with diisopropyl ether and dried under reduced pressure to give 4-[5-(4-methoxycarbonylphenyl)-1,3,4-thiadiazol-2-yl] piperidinium trifluoroacetate (1.31 g).

IR (KBr): 2956, 2840, 1722, 1673, 1436, 1282, 1211, 1180, 1124 cm$^{-1}$

NMR (DMSO-d$_6$, δ): 2.0–2.2 (2H, m), 2.30 (2H, d, J=12.0 Hz), 3.0–3.2 (2H, m), 3.4–3.7 (3H, m), 3.90 (3H, s), 8.12 (4H, s), 8.6–9.0 (2H, br)

APCI-MASS: m/z=304 (M+H)$^+$ free.

Preparation 6

To a suspension of ethyl 4-bromobenzoate (1.37 g), (4-n-pentyloxyphenyl)acetylene (565 mg), triphenylphosphine (16 mg) and copper(I) iodide (6 mg) in triethylamine (10 ml) and pyridine (4 ml) was added palladium(II) chloride bis(triphenylphosphine) (21 mg) and the reaction mixture was stirred for 24 hours at 80° C. After cooling, the precipitate was filtered off, and the filtrate was evaporated under reduced pressure. The residue was taken up to dichloromethane, and the solution was washed successively with 1N HCl, water, brine and dried over magnesium sulfate. The solvents were removed under reduced pressure and the residue was triturated with acetonitrile, collected by filtration and dried under reduced pressure to give ethyl 4-(4-n-pentyloxyphenylethynyl)benzoate (355 mg).

IR (KBr): 2940, 2869, 1706, 1515, 1274, 1103 cm$^{-1}$

NMR (CDCl$_3$, δ): 0.93 (3H, t, J=7.0 Hz), 1.3–1.6 (7H, m), 1.7–1.9 (2H, m), 3.97 (2H, t, J=6.5 Hz), 4.38 (2H, q, J=7.1 Hz), 6.87 (2H, d, J=8.9 Hz), 7.44 (2H, d, J=8.9 Hz), 7.51 (2H, d, J=8.5 Hz), 8.01 (2H, d, J=8.5 Hz)

APCI-MASS: m/z=337 (M+H)$^+$

Preparation 7

To a solution of 4-(4-n-pentyloxyphenyl)benzamide (1.0 g) in tetrahydrofuran (10 ml) was added Lawesson's reagent (1.0 g). The reaction mixture was refluxed for 3 hours and diluted with dichloromethane. The insoluble residue was removed by filtration and the filtrate was evaporated to dry. To a solution of the residue in tetrahydrofuran (10 ml) was added ethyl bromopyruvate (887 mg). The mixture was stirred for 3 hours at room temperature, diluted with dichloromethane (100 ml) and washed with water and brine. The separated organic layer was dried over magnesium sulfate and the solvents were removed under reduced pressure. The residue was triturated with acetonitrile and the solid was collected by filtration and dried under reduced pressure to give ethyl 4-imino-2-oxo-4-[4-(4-n-pentyloxyphenyl)phenyl]-3-vas thiapentanoate (895 mg).

IR (KBr): 3120, 2954, 2863, 1753, 1591, 1498, 1471 cm$^{-1}$

NMR (CDCl$_3$, δ): 0.94 (3H, t, J=7.0 Hz), 1.33 (3H, t, J=7.1 Hz), 1.4–1.6 (4H, m), 1.7–1.9 (2H, m), 3.55 (1H, d, J=12.2 Hz), 3.9–4.1 (3H, m), 4.2–4.4 (2H, m), 4.47 (1H, s), 6.97 (2H, d, J=8.8 Hz), 7.53 (2H, d, J=8.8 Hz), 7.59 (2H, d, J=8.5 Hz), 7.92 (2H, d, J=8.5 Hz)

APCI-MASS: m/z=414 (M+H)$^+$

Preparation 8

To a suspension of ethyl 4-imino-2-oxo-4-[4-(4-n-pentyloxyphenyl)phenyl]-3-thiapentanoate (0.87 g) in tetrahydrofuran (16 ml) and ethanol (8 ml) was added 10% NaOH aq. (1.32 ml). The mixture was refluxed for 1 hour and adjusted to pH 2.0 with 1N HCl. The precipitate was collected by filtration, washed with water and dried under reduced pressure to give crude 4-imino-2-oxo-4-[4-(4-n-pentyloxyphenyl)phenyl]-3-thiapentanoic acid. A suspension of crude 4-imino-2-oxo-4-[4-(4-n-pentyloxyphenyl)phenyl]-3-thiapentanoic acid obtained in ethanol (50 ml) was refluxed for 4 hours. After cooling, the precipitate was collected by filtration, washed with ethanol and dried under reduced pressure to give 2-[4-(4-n-pentyloxyphenyl)phenyl]-4-thiazolecarboxylic acid (353 mg).

IR (KBr): 2958, 2935, 1687, 1602, 1465, 1253, 1199 cm$^{-1}$

NMR (DMSO-d$_6$, δ): 0.91 (3H, t, J=6.9 Hz), 1.3–1.5 (4H, m), 1.7–1.9 (2H, m), 4.02 (2H, t, J=6.5 Hz), 7.04 (2H, d, J=8.8 Hz), 7.69 (2H, d, J=8.8 Hz), 7.79 (2H, d, J=8.5 Hz), 8.02 (2H, d, J=8.5 Hz), 8.49 (1H, s), 13.1 (1H, br s)

APCI-MASS: m/z=368 (M+H)$^+$

Preparation 9

To a suspension of 4-n-pentyloxybenzoic acid (5.0 g) in toluene was added oxalyl chloride (15 ml) and N,N-dimethylformamide (0.1 ml) and the mixture was stirred for 2 hours at room temperature. The solvents were evaporated under reduced pressure to give crude 4-n-pentyloxybenzoyl chloride. To a suspension of N,O-dimethylhydroxylamine a hydrochloride (3.51 g) and pyridine (5.82 ml) in tetrahydrofuran (25 ml) was added the solution of crude 4-n-pentyloxybenzoyl chloride in tetrahydrofuran (25 ml) dropwise at 0° C. and the mixture was stirred for 3 hours at room temperature. To the reaction mixture 1N HCl was added and extracted with ethyl acetate. The organic layer was separated, washed with water and brine, dried over magnesium sulfate and evaporated under reduced pressure to give N-(4-n-pentyloxybenzoyl)-N,O-dimethylhydroxylamine (4.63 g).

NMR (CDCl$_3$, δ): 0.94 (3H, t, J=7.0 Hz), 1.3–1.6 (4H, m), 1.7–1.9 (2H, m), 3.35 (3H, s), 3.56 (3H, s), 3.99 (2H, t, J=6.5 Hz), 6.88 (2H, d, J=8.9 Hz), 7.71 (2H, d, J=8.9 Hz)

APCI-MASS: m/z=252 (M+H)$^+$

Preparation 10

To a solution of N-(4-n-pentyloxybenzoyl)-N,O-dimethylhydroxylamine (4.52 g) in tetrahydrofuran (25 ml) was added 1.6 molar tetrahydrofuran solution of vinylmagnesium bromide (25.5 ml) at −50° C. dropwise and the mixture was stirred for 3 hours at −20° C. To the mixture was added 1N HCl (50 ml) dropwise and the mixture was extracted with ethyl acetate. The organic layer was separated, washed with brine, dried over magnesium sulfate and evaporated under reduced pressure. The residue was purified with silica gel column chromatography (hexane/ethyl acetate)=(8/2) to give 1-(4-n-pentyloxyphenyl)acrolein (2.40 g).

IR (KBr): 2956, 2935, 2867, 1672, 1600, 1510, 1255, 1170 cm$^{-1}$

NMR (CDCl$_3$, δ): 0.94 (3H, t, J=7.1 Hz), 1.3–1.5 (4H, m), 1.7–1.9 (2H, m), 4.03 (2H, t, J=6.5 Hz), 5.86 (1H, dd, J=10.5 and 1.9 Hz), 6.42 (1H, dd, J=17.0 and 1.9 Hz), 6.94 (2H, d, J=8.9 Hz), 7.21 (1H, dd, J=17.0 and 10.9 Hz), 7.95 (2H, d, J=8.9 Hz)

APCI-MASS: m/z=219 (M+H)$^+$

Preparation 11

A suspension of 1-(4-n-pentyloxyphenyl)acrolein (2.38 g), methyl 4-formylbenzoate (1.97 g), 3-benzyl-5-(2-hydroxyethyl)-4-methylthiazolium chloride and triethylamine (0.91 ml) in ethanol (10 ml) was refluxed for 18 hours. After cooling, the solvents were removed under reduced pressure. The solids were taken up in 1N HCl and extracted with dichloromethane. The organic layer was washed successively with water and brine, dried over magnesium sulfate and evaporated under reduced pressure. The residue was triturated with diisopropyl ether, collected by filtration and dried under reduced pressure to give 1-(4-methoxycarbonylphenyl)-4-(4-n-pentyloxyphenyl)butane-1,4-dione (3.41 g).

IR (KBr): 2956, 2867, 1722, 1672, 1606, 1284, 1257, 1110 cm$^{-1}$

NMR (CDCl$_3$, δ): 0.94 (3H, t, J=7.0 Hz), 1.5–1.7 (4H, m), 1.8–2.0 (2H, m), 3.44 (4H, s), 3.95 (3H, s), 4.03 (2H, t, J=6.5 Hz), 6.94 (2H, d, J=8.9 Hz), 7.99 (2H, d, J=8.9 Hz), 8.08 (2H, d, J=8.7 Hz), 8.14 (2H, d, J=8.7 Hz)

APCI-MASS: m/z=383 (M+H)$^+$

Preparation 12

A suspension of 1-(4-methoxycarbonylphenyl)-4-(4-n-pentyloxyphenyl) butane-1,4-dione (765 mg) and phosphorus pentasulfide (533 mg) in tetrahydrofuran (10 ml) was stirred for 6 hours at room temperature, poured into water and stirred for 1 hour. The precipitate was collected by filtration, washed with water and dried under reduced pressure to give methyl 4-[5-(4-n-pentyloxyphenyl)thiophen-2-yl]benzoate (668 mg).

IR (KBr): 2956, 2935, 2867, 1722, 1604, 1438, 1284, 1112, 1022 cm$^{-1}$

NMR (CDCl$_3$, δ): 0.94 (3H, t, J=6.9 Hz), 1.3–1.5 (4H, m), 1.7–1.9 (2H, m), 3.93 (3H, s), 3.99 (2H, t, J=6.5 Hz), 6.88 (2H, d, J=8.8 Hz), 7.19 (1H, d, J=3.8 Hz), 7.37 (1H, d, J=3.8 Hz), 7.55 (2H, d, J=8.8 Hz), 7.66 (2H, d, J=8.5 Hz), 8.04 (2H, d, J=8.5 Hz)

APCI-MASS: m/z=381 (M+H)$^+$

Preparation 13

A solution of 1-(4-methoxycarbonylphenyl)-4-(4-n-pentyloxyphenyl)butane-1,4-dione (765 mg) and p-toluenesulfonic acid monohydrate (8 mg) in toluene (10 ml) was refluxed for 6 hours. The reaction mixture was diluted with dichloromethane, washed with water and brine, and dried over magnesium sulfate. The solvents were removed under reduced pressure and the precipitate was triturated with methanol, collected by filtration, washed with methanol and dried under reduced pressure to give methyl 4-[5-(4-n-pentyloxyphenyl)furan-2-yl]benzoate (665 mg).

IR (KBr): 2956, 2933, 1720, 1284, 1253, 1176, 1110 cm$^{-1}$

NMR (CDCl$_3$, δ): 0.94 (3H, t, J=6.9 Hz), 1.3–1.5 (4H, m), 1.7–1.9 (2H, m), 3.93 (3H, s), 3.99 (2H, t, J=6.5 Hz), 6.62 (1H, d, J=3.5 Hz), 6.85 (1H, d, J=3.5 Hz), 6.94 (2H, d, J=8.8 Hz), 7.67 (2H, d, J=8.8 Hz), 7.76 (2H, d, J=8.5 Hz), 8.05 (2H, d, J=8.5 Hz)

APCI-MASS: m/z=365 (M+H)$^+$

Preparation 14

A mixture of 4-cyclohexylcyclohexanone (1.54 g), 1-(4-ethoxycarbonylphenyl)piperazine (2 g) and titanium(IV) isopropoxide (3.18 ml) was stirred at room temperature. After 1 hour, the IR spectrum of the mixture showed no ketone band, and the viscous solution was diluted with absolute ethanol (8.5 ml). Sodium cyanoborohydride (0.343 g) was added, and the solution was stirred for 3 hours. Water (3 ml) was added with stirring, and the resulting in organic precipitate was filtered and washed with ethanol. The filtrate was extracted with ethyl acetate. The organic layer was taken and dried over magnesium sulfate. The magnesium sulfate was filtered off, and filtrate was evaporated under reduced pressure. The residue was subjected to column chromatography on silica gel and eluted with (hexane/ethyl acetate)=(3/1). The fractions containing the less polar compound were collected and evaporated under reduced pressure to give ethyl 4-[4-(cis-4-cyclohexylcyclohexyl)piperazin-1-yl]benzoate (692 mg) as byproduct. The fractions containing the more polar compound were collected and evaporated under reduced pressure to give ethyl 4-[4-(trans-4-cyclohexylcyclohexyl)piperazin-1-yl]benzoate (587 mg).

Trans Isomer

IR (KBr): 2931.3, 1708.6, 1606.4, 1234.2 cm$^{-1}$

NMR (CDCl$_3$, δ): 0.80–1.5 (12H, m), 1.36 (3H, t, J=7.1 Hz), 1.5–2.1 (8H, m), 2.40 (1H, m), 2.7–2.9 (4H, m), 3.3–3.5 (4H, m), 4.33 (2H, q, J=7.1 Hz), 6.86 (2H, d, J=9.1 Hz), 7.92 (2H, d, J=9.1 Hz)

APCI-MASS: m/z=m/z=399 (M+H)$^+$

Cis Isomer

IR (KBr): 2925.5, 1706.7, 1606.4, 1282.4 cm$^{-1}$

NMR (CDCl$_3$, δ): 0.8–1.9 (20H, m), 1.36 (2H, t, J=7.1 Hz), 2.25 (1H, m), 2.6–2.8 (4H, m), 3.2–3.5 (4H, m), 4.33 (2H, q, J=7.1 Hz), 6.85 (2H, d, J=9.1 Hz), 7.92 (2H, d, J=9.1 Hz)

APCI-MASS: m/z=399 (M+H)$^+$

The following compound was obtained according to a similar manner to that of Preparation 14.

Preparation 15

4-[4-(1-Cyclohexylpiperidin-4-yl)piperidin-1-yl]benzonitrile.

IR (KBr): 2931.3, 2215.8, 1606, 1515.8, 1178.3 cm$^{-1}$

NMR (CDCl$_3$, δ): 1.0–2.6 (23H, m), 2.65–2.95 (2H, m), 2.95–3.25 (2H, m), 3.8–4.0 (2H, m), 6.83 (2H, d, J=8.9 Hz), 7.46 (2H, d, J=8.9 Hz)

APCI-MASS: m/z=352 (M+H)$^+$

Preparation 16

To a suspension of magnesium turnings (0.48 g) in tetrahydrofuran (10 ml) was added dropwise a solution of 4-hexyloxybromobenzene (5 g) in tetrahydrofuran (70 ml) and stirred for 1 hour at ambient temperature. Then to the reaction mixture was added 1-benzyloxycarbonyl-4-piperidone (4.12 g) and stirred for 2 hours under ice-cooling. The reaction was quenched with saturated NH$_4$Cl aq. and extracted with ethyl acetate. The organic layer was taken and dried over magnesium sulfate. The magnesium sulfate was filtered off, and filtrate was evaporated under reduced pressure. The residue was subjected to column chromatography on silica gel and eluted with (hexane/ethyl acetate)=(3/1).

The fractions containing the object compound were collected and evaporated under reduced pressure to give 1-benzyloxycarbonyl-4-(4-hexyloxyphenyl)-4-hydroxypiperidine (3.44 g).

IR (KBr): 3430, 1675.8, 1247.7 cm$^{-1}$

NMR (CDCl$_3$, δ): 0.90 (3H, t, J=6.6 Hz), 1.2–1.85 (11H, m), 1.85–2.1 (2H, m), 3.2–3.5 (2H, m), 3.94 (2H, t, J=6.5 Hz), 4.05–4.2 (2H, m), 5.15 (2H, s), 6.87 (2H, d, J=8.8 Hz), 7.3–7.5 (7H, m)

APCI-MASS: m/z=394 (M+H–H$_2$O)$^+$

The following compound was obtained according to a similar manner to that of Preparation 16.

Preparation 17

1-tert-Butoxycarbonyl-4-(4-hexyloxyphenyl)-4-hydroxypiperidine

IR (KBr): 3434.6, 2954.4, 2931.3, 1693.2, 1670.1, 1172.5 cm$^{-1}$

NMR (CDCl$_3$, δ): 0.90 (3H, t, J=6.5 Hz), 1.2–1.5 (8H, m), 1.49 (9H, s), 1.65–1.85 (4H, m), 1.85–2.1 (2H, m), 3.1–3.35 (2H, m), 4.10 (2H, t, J=7.1 Hz), 4.17 (1H, br s), 6.88 (2H, d, J=8.9 Hz), 7.37 (2H, d, J=8.9 Hz).

Preparation 18

To a solution of 1-benzyloxycarbonyl-4-(4-hexyloxyphenyl)-4-hydroxypiperidine (1.4 g) in methanol (28 ml) was added dry 10% palladium on carbon (0.7 g) and stirred for 6 hours under hydrogen atmosphere. The palladium on carbon was filtered off, and the filtrate was evaporated under reduced pressure to give 4-(4-hexyloxyphenyl)-4-hydroxypiperidine (0.74 g).

IR (KBr): 3332.4, 1610.3, 1513.8, 1249.6 cm$^{-1}$

NMR (CDCl$_3$, δ): 0.90 (3H, t, J=6.5 Hz), 1.2–1.6 (6H, m), 1.6–1.9 (4H, m), 1.9–2.19 (2H, m), 2.35 (2H, br s), 2.85–3.25 (4H, m), 3.95 (2H, t, J=6.5 Hz), 6.87 (2H, d, J=8.8 Hz), 7.40 (2H, d, J=8.8 Hz)

APCI-MASS: m/z=260 (M+H–H$_2$O)$^+$

The following compounds [Preparations 19 and 20] were obtained according to a similar manner to that of Preparation 18.

Preparation 19

4-[4-(4-Hexyloxyphenyl)-4-hydroxypiperidin-1-yl]benzoic acid

IR (KBr): 3548.4, 1668.1, 1600.6, 1187.9 cm$^{-1}$

NMR (DMSO-d$_6$, δ): 0.87 (3H, t, J=6.5 Hz), 1.2–1.5 (6H, m), 1.6–1.8 (4H, m), 1.8–2.1 (2H, m), 3.1–3.4 (2H, m), 3.7–3.85 (2H, m), 3.92 (2H, t, J=6.5 Hz), 4.97 (1H, s), 6.85 (2H, d, J=8.8 Hz), 6.99 (2H, d, J=9.0 Hz), 7.35 (2H, d, J=8.8 Hz), 7.76 (2H, d, J=9.0 Hz), 12.2 (1H, s)

APCI-MASS: m/z=398 (M+H)$^+$

Preparation 20

Ethyl 4-[4-(4-hexyloxyphenyl)piperidin-1-yl]benzoate

IR (KBr): 1700.9, 1606.4, 1511.9, 1274.7, 1178.3 cm$^{-1}$

NMR (CDCl$_3$, δ): 0.90 (3H, t, J=6.5 Hz), 1.2–1.6 (6H, m), 1.40 (3H, t, J=7.2 Hz), 1.7–2.1 (6H, m), 2.5–2.8 (1H, m), 2.8–3.05 (2H, m), 3.93 (2H, t, J=6.5 Hz), 3.9–4.1 (2H, m), 4.32 (2H, q, J=7.2 Hz), 6.84 (2H, d, J=8.7 Hz), 6.90 (2H, d, J=9.0 Hz), 7.12 (2H, d, J=8.7 Hz), 7.92 (2H, d, J=9.0 Hz)

APCI-MASS: m/z=410 (M+H)$^+$

Preparation 21

To a solution of methyl 3-(4-n-hexyloxyphenyl)propionate (1.18 g) in ethanol (10 ml) was added hydrazine monohydrate (1.08 ml) and the mixture was refluxed for 24 hours. After cooling, the solvent was removed under reduced pressure. Water was added and the precipitate was collected by filtration, washed with water and dried under reduced pressure to give 3-(4-n-hexyloxyphenyl)propionohydrazide (0.92 g).

IR (KBr): 3317, 2929, 1625, 1513, 1245 cm$^{-1}$

NMR (DMSO-d$_6$, δ): 0.87 (3H, t, J=6.4 Hz), 1.3–1.5 (6H, m), 1.6–1.8 (2H, m), 2.26 (2H, t, J=7.7 Hz), 2.72 (2H, t, J=7.7 Hz), 3.90 (2H, t, J=6.5 Hz), 4.14 (2H, d, J=4.2 Hz), 6.80 (2H, d, J=8.6 Hz), 7.07 (2H, d, J=8.6 Hz), 8.93 (1H, t, J=4.2 Hz)

APCI-MASS: m/z=265 (M+H)$^+$

The following compounds [Preparations 22 and 23] were obtained according to a similar manner to that of Preparation 21.

Preparation 22

N-(tert-Butoxycarbonyl)isonipecotinohydrazide

IR (KBr): 3320, 2979, 2942, 2846, 1691, 1629, 1527, 1432, 1230, 1178 cm$^{-1}$

NMR (DMSO-d$_6$, δ): 1.39 (9H, s), 1.3–1.7 (4H, m), 2.1–2.3 (1H, m), 2.69 (2H, t, J=11.9 Hz), 3.93 (2H, d, J=13.2 Hz), 4.15 (2H, s), 8.99 (1H, s)

APCI-MASS: m/z=144 (M−Boc)$^+$

Preparation 23

4-(3-Phenoxypropyloxy)benzohydrazide

IR (KBr): 3297, 3182, 2948, 1650, 1502, 1305, 1253 cm$^{-1}$

NMR (DMSO-d$_6$, δ): 2.18 (2H, tt, J=6.2 and 6.2 Hz), 4.12 (2H, t, J=6.2 Hz), 4.18 (2H, t, J=6.2 Hz), 4.41 (2H, s), 6.9–7.1 (5H, m), 7.2–7.4 (2H, m), 7.79 (2H, d, J=8.8 Hz), 9.60 (1H, s)

APCI-MASS: m/z=287 (M+H)$^+$

Preparation 24

To a suspension of 1-acetyl-4-(4-hydroxyphenyl)piperazine (20 g) and potassium bicarbonate (12.55 g) in dimethylsulfoxide (200 ml) was added 1-bromohexane (19.12 ml) and stirred for 24 hours at 80° C. The reaction mixture was added to a mixture of water and ethyl acetate. The organic layer was taken and dried over is magnesium sulfate. The magnesium sulfate was filtered off, and the filtrate was evaporated under reduced pressure to give 1-acetyl-4-(4-hexyloxyphenyl)piperazine (14.5 g).

IR (KBr): 1621.8, 1513.8, 1251.6, 825.4 cm$^{-1}$

NMR (CDCl$_3$, δ): 0.90 (3H, t, J=6.4 Hz), 1.25–1.55 (6H, m), 1.65–1.85 (2H, m), 2.13 (3H, s), 3.02 (2H, t, J=5.2 Hz), 3.04 (2H, t, J=5.2 Hz), 3.61 (2H, t, J=5.2 Hz), 3.76 (2H, t, J=5.2 Hz), 3.91 (2H, t, J=6.5 Hz), 6.83 (2H, d, J=9.1 Hz), 6.89 (2H, d, J=9.1 Hz).

The following compounds [Preparations 25 to 27] were obtained according to a similar manner to that of Preparation 24.

Preparation 25

4-[4-(4-Hexyloxyphenyl)piperazin-1-yl]benzonitrile

IR (KBr): 2212.0, 1602.6, 1510.0, 1247.7, 827.3 cm$^{-1}$

NMR (CDCl$_3$, δ): 0.90 (3H, t, J=6.5 Hz), 1.2–1.6 (6H, m), 1.65–1.9 (2H, m), 3.1–3.3 (4H, m), 3.4–3.6 (4H, m), 3.92 (2H, t, J=6.5 Hz), 6.8–7.0 (6H, m), 7.52 (2H, d, J=9.0 Hz)

APCI-MASS: m/z=364 (M+H)$^+$

Preparation 26

Methyl 4-(3-phenoxypropyloxy)benzoate

IR (KBr): 2944, 2885, 1722, 1604, 1500, 1247 cm$^{-1}$

NMR (CDCl$_3$, δ): 2.28 (2H, tt, J=6.0 and 6.0 Hz), 3.88 (3H, s), 4.16 (2H, t, J=6.0 Hz), 4.21 (2H, t, J=6.0 Hz), 6.8–7.0 (5H, m), 7.2–7.4 (2H, m), 7.98 (2H, d, J=9.0 Hz)

APCI-MASS: m/z=287 (M+H)$^+$

Preparation 27

Methyl 4-[5-(1-n-octylpiperidin-4-yl)-1,3,4-thiadiazol-2-yl]benzoate

IR (KBr): 2925, 2852, 1714, 1440, 1278 cm$^{-1}$

NMR (CDCl$_3$, δ): 0.89 (3H, t, J=6.5 Hz), 1.2–1.4 (10H, m), 1.4–2.4 (10H, m), 3.0–3.1 (2H, m), 3.2–3.3 (1H, m), 3.95 (3H, s), 8.01 (2H, d, J=8.6 Hz), 8.13 (2H, d, J=8.6 Hz)

APCI-MASS: m/z=416 (M+H)$^+$

Preparation 28

A solution of 1-acetyl-4-(4-hexyloxyphenyl)piperazine (14 g) in 1N HCl was refluxed for 5 hours. The reaction mixture was adjusted to pH 8 with saturated Na$_2$CO$_3$ aq. and extracted with ethyl acetate. The organic layer was dried over magnesium sulfate. The magnesium sulfate was filtered off, and the filtrate was evaporated under reduced pressure. To the residue was added ethyl acetate and 4N HCl in ethyl acetate (23 ml) and stirred for 1 hour. The resulting precipitate was collected by filtration to give 1-(4-hexyloxyphenyl)piperazine dihydrochloride (8.669 g).

IR (KBr): 1604.5, 1513.8, 1259.3 cm$^{-1}$

NMR (DMSO-d$_6$, δ): 0.874 (3H, t, J=6.6 Hz), 1.2–1.5 (6H, m), 1.6–1.8 (2H, m), 3.2–3.55 (8H, m), 3.92 (2H, t, J=6.4 Hz), 6.92 (2H, d, J=9.1 Hz), 7.15 (2H, d, J=9.1 Hz), 8.27 (1H, br s), 9.61 (2H, br s)

APCI-MASS: m/z=263 (M+H)$^+$

The following compound was obtained according to a similar manner to that of Preparation 28.

Preparation 29

1-(4-Cyclohexyloxyphenyl)piperazine dihydrochloride

Preparation 30

To a suspension of 1-(4-hexyloxyphenyl)piperazine dihydrochloride (0.914 g) and potassium bicarbonate (0.564 g) in dimethylsulfoxide (5 ml) was added ethyl p-fluorobenzoate (0.2 ml) and stirred for 10 hours at 150° C. The reaction mixture was added to a mixture of water and ethyl acetate. The organic layer was taken and dried over magnesium sulfate. The magnesium sulfate was filtered off, and the filtrate was evaporated under reduced pressure to give ethyl 4-[4-(4-hexyloxyphenyl)piperazin-1-yl]benzoate (0.347 g).

IR (KBr): 1710.6, 1606.4, 1511.9, 1286.3, 1224.6 cm$^{-1}$

NMR (CDCl$_3$, δ): 0.90 (3H, t, J=6.5 Hz), 1.2–1.55 (6H, m), 1.37 (3H, t, J=7.1 Hz), 1.65–1.85 (2H, m), 3.1–3.25 (4H, m), 3.4–3.55 (4H, m), 3.92 (2H, t, J=6.5 Hz), 4.33 (2H, q, J=7.1 Hz), 6.8–7.0 (6H, m), 7.95 (2H, d, J=9.0 Hz).

The following compounds [Preparations 31 to 38] were obtained according to a similar manner to that of Preparation 30.

Preparation 31

Methyl 4-[4-(4-cyclohexylphenyl)piperazin-1-yl]methylbenzoate

IR (KBr): 2925.5, 1720.2, 1276.6, 1108.9 cm$^{-1}$

NMR (CDCl$_3$, δ): 1.1–2.0 (10H, m), 2.42 (1H, m), 2.5–2.7 (4H, m), 3.1–3.3 (4H, m), 3.61 (2H, s), 3.91 (3H, s), 6.85 (2H, d, J=8.7 Hz), 7.10 (2H, d, J=8.7 Hz), 7.43 (2H, d, J=8.2 Hz), 8.00 (2H, d, J=8.2 Hz).

Preparation 32

Ethyl 4-[4-(4-cyclohexyloxyphenyl)piperazin-1-yl]benzoate

Preparation 33

3-[2-(4-Morpholinophenylamino)ethyl]-2-oxazolidone

IR (KBr): 3330.5, 1740, 1523.5, 1118.5 cm$^{-1}$

NMR (CDCl$_3$, δ): 2.9–3.2 (4H, m), 3.2–3.7 (4H, m), 3.60 (2H, dd, J=8.3 and 6.5 Hz), 3.8–4.0 (4H, m), 4.29 (2H, dd, J=8.9 and 7.1 Hz), 6.5–6.7 (2H, m), 6.8–7.0 (2H, m)

APCI-MASS: m/z=292 (M+H)$^+$

Preparation 34

4-[4-(4-Morpholinophenyl)piperazin-1-yl]benzonitrile

IR (KBr): 2210.0, 1600.6, 1511.9, 1234.2 cm$^{-1}$

NMR (CDCl$_3$, δ): 3.2–3.15 (4H, m), 3.15–3.3 (4H, m), 3.4–3.55 (4H, m), 3.8–3.9 (4H, m), 6.8–7.0 (6H, m), 7.52 (2H, d, J=9.0 Hz)

APCI-MASS: m/z=349 (M+H)$^+$

Preparation 35
Diphenylmethyl 4-[4-(4-hexyloxyphenyl)-4-hydroxypiperidin-1-yl]benzoate
IR (KBr): 3463.5, 1681.6, 1604.5, 1184.1 cm$^{-1}$
NMR (CDCl$_3$, δ): 0.90 (3H, t, J=6.5 Hz), 1.2–1.6 (6H, m), 1.65–1.95 (4H, m), 2.0–2.3 (2H, m), 3.3–3.5 (2H, m), 3.65–3.85 (2H, m), 3.95 (2H, t, J=6.5 Hz), 6.88 (2H, d, J=8.9 Hz), 6.8–7.0 (2H, m), 7.09 (1H, s), 7.2–7.5 (10H, m), 8.03 (2H, d, J=8.9 Hz)
APCI-MASS: m/z=564 (M+H)$^+$ Preparation 36
Ethyl 4-[4-(4-hexyloxyphenyl)-1,2,3,6-tetrahydropyridin-1-yl]benzoate
IR (KBr): 2931.3, 1706.7, 1608.3, 1515.8 cm$^{-1}$
NMR (CDCl$_3$, δ): 0.91 (3H, t, J=6.5 Hz), 1.2–1.6 (6H, m), 1.37 (3H, t, J=7.1 Hz), 1.7–1.9 (2H, m), 2.67 (2H, m), 3.63 (2H, t, J=5.6 Hz), 3.96 (2H, m, J=6.5 Hz), 3.9–4.1 (2H, m), 4.32 (2H, q, J=7.1 Hz), 6.0–6.1 (1H, m), 7.34 (2H, d, J=8.8 Hz), 7.94 (2H, d, J=8.8 Hz)
FAB-MASS: m/z=406 (M+H)$^+$ Preparation 37
4-[4-(3-Methoxyphenyl)piperazin-1-yl]benzonitrile
IR (KBr): 2829.1, 2213.9, 1604.5, 1174.4 cm$^{-1}$
NMR (CDCl$_3$, δ): 3.3–3.4 (4H, m), 3.4–3.55 (4H, m), 3.81 (3H, s), 6.46 (1H, d, J=9.0 Hz), 6.49 (1H, s), 6.56 (1H, d, J=9.0 Hz), 6.90 (2H, d, J=9.0 Hz), 7.13 (1H, dd, J=9.0 Hz), 7.52 (2H, d, J=9.0 Hz).

Preparation 38
4-[4-(Piperidin-4-yl)piperidin-1-yl]benzonitrile
IR (KBr): 3332.4, 2212.0, 1602.6, 1513.8, 1178 cm$^{-1}$
NMR (CDCl$_3$, δ): 1.0–1.5 (6H, m), 1.6–2.0 (4H, m), 1.91 (1H, s), 2.5–2.7 (2H, m), 2.7–2.9 (2H, m), 3.0–3.2 (2H, m), 3.8–4.0 (2H, m), 6.84 (2H, d, J=9.0 Hz), 7.45 (2H, d, J=9.0 Hz)
APCI-MASS: m/z=270 (M+H)$^+$ Preparation 39
A solution of 4-[4-(4-hexyloxyphenyl)piperazin-1-yl]-benzonitrile (0.582 g) in the mixture of conc. HCl (5.8 ml) and acetic acid (2.9 ml) was refluxed for 3 hours. The reaction mixture was pulverized with water (25 ml). The precipitate was collected by filtration to give 4-[4-(4-hexyloxyphenyl)piperazin-1-yl]benzoic acid hydrochloride (0.51 g).
IR (KBr): 1726.0, 1699.0, 1606.4, 1511.9 cm$^{-1}$
NMR (DMSO-d$_6$, δ): 0.88 (3H, t, J=6.5 Hz), 1.2–1.5 (6H, m), 1.6–1.8 (2H, m), 3.5–3.9 (8H, m), 4.00 (2H, t, J=6.4 Hz), 7.07 (2H, d, J=8.9 Hz), 7.09 (2H, d, J=8.9 Hz), 7.61 (2H, d, J=8.9 Hz), 7.84 (2H, d, J=8.9 Hz)
APCI-MASS: m/z=383 (M+H)$^+$ The following compounds [Preparations 40 to 42] were obtained according to a similar manner to that of Preraration 39.

Preparation 40
4-[4-(4-Morpholinophenyl)piperazin-1-yl]benzoic acid dihydrochloride
IR (KBr): 1706.7, 1602.6, 1513.8, 1232.3 cm$^{-1}$
NMR (DMSO-d$_6$, δ): 2.9–3.0 (4H, m), 3.1–3.2 (4H, m), 3.3–3.5 (4H, m), 3.65–3.8 (4H, m), 6.87 (2H, d, J=8.7 Hz), 6.93 (2H, d, J=8.7 Hz), 7.02 (2H, d, J=9.0 Hz), 7.79 (2H, d, J=9.0 Hz)
APCI-MASS: m/z=368 (M+H)$^+$ Preparation 41
4-[4-(3-Hydroxyphenyl)piperazin-1-yl]benzoic acid dihydrobromide
IR (KBr): 3183.9, 1679.7, 1604.5, 1232.3 cm$^{-1}$
NMR (DMSO-d$_6$, δ): 3.3–3.7 (8H, m), 6.45 (1H, d, J=7.9 Hz), 6.62 (1H, d, J=7.9 Hz), 6.68 (1H, s), 7.04 (2H, d, J=9.0 Hz), 7.13 (1H, dd, J=7.9 Hz), 7.81 (2H, d, J=9.0 Hz)
APCI-MASS: m/z=299 (M+H)$^+$ Preparation 42
4-[4-(1-Cyclohexylpiperidin-4-yl)piperidin-1-yl]benzoic acid dihydrobromide
IR (KBr): 1668.1, 1606, 1186 cm$^{-1}$
NMR (DMSO-d$_6$, δ): 1.0–2.3 (21H, m), 2.7–4.1 (8H, m), 6.94 (2H, d, J=8.6 Hz), 7.76 (2H, d, J=8.6 Hz)
APCI-MASS: m/z=371 (M+H)$^+$ Preparation 43
To a solution of ethyl 4-[4-(4-hexyloxyphenyl)piperazin-1-yl]benzoate (2.19 g) in the mixture of ethanol (22 ml) and tetrahydrofuran (22 ml) was added 2N NaOH aq. and refluxed for 5 hours. The reaction mixture was adjusted to pH 1–1.5 with 1N HCl and the resulting precipitate was collected by filtration to give 4-[4-(4-hexyloxyphenyl)piperazin-1-yl]benzoic acid hydrochloride (1.99 g).
IR (KBr): 1664.3, 1600.6, 1511.9, 1230.4 cm$^{-1}$
NMR (DMSO-d$_6$, δ): 0.88 (3H, t, J=6.5 Hz), 1.2–1.5 (6H, m), 1.55–1.8 (2H, m), 3.0–3.6 (8H, m), 3.88 (2H, t, J=6.4 Hz) 6.83 (2H, d, J=9.2 Hz), 6.94 (2H, d, J=9.2 Hz), 7.01 (2H, d, J=8.9 Hz), 7.78 (2H, d, J=8.9 Hz).

The following compounds [Preparations 44 to 60] were obtained according to a similar manner to that of Preparation 43.

Preparation 44
4-[4-(trans-4-Cyclohexylcyclohexyl)piperazin-1-yl]benzoic acid hydrochloride
IR (KBr): 2919.7, 2852.2, 1695.1, 1606.4, 1234.2 cm$^{-1}$
NMR (DMSO-d$_6$, δ): 0.8–2.0 (20H, m), 2.12 (1H, m), 2.9–3.6 (8H, m), 7.03 (2H, d, J=9.0 Hz), 7.81 (2H, d, J=9.0 Hz)
APCI-MASS: m/z=371 (M+H)$^+$ Preparation 45
4-[4-(cis-$^4$-Cyclohexylcyclohexyl)piperazin-1-yl]benzoic acid hydrochloride
IR (KBr): 1693.2, 1604.5, 1232.3, 1186.0 cm$^{-1}$
NMR (DMSO-d$_6$, δ): 0.8–2.0 (21H, m), 3.2–3.3 (8H, m), 7.03 (2H, d, J=9.0 Hz), 7.80 (2H, d, J=9.0 Hz)
APCI-MASS: m/z=371 (M+H)$^+$ Preparation 46
4-[4-(4-Cyclohexylphenyl)piperazin-1-yl]methylbenzoic acid hydrochloride
IR (KBr): 2925.5, 1704.8, 1251.6 cm$^{-1}$ Preparation 47
4-[4-(4-Cyclohexyloxyphenyl)piperazin-1-yl]benzoic acid hydrochloride Preparation 48
4-[4-(4-Hexyloxyphenyl)piperidin-1-yl]benzoic acid
IR (KBr): 1670.1, 1602.6, 1513.8, 1394.3, 1216.9 cm$^{-1}$
NMR (DMSO-d$_6$, δ): 0.87 (3H, t, J=6.5 Hz), 1.2–1.5 (6H, m), 1.5–1.9 (6H, m), 2.55–3.0 (3H, m), 3.95 (2H, t, J=6.5 Hz), 3.9–4.0 (2H, m), 6.84 (2H, d, J=8.7 Hz), 6.92 (2H, d, J=8.9 Hz), 7.15 (2H, d, J=8.7 Hz), 7.73 (2H, d, J=8.9 Hz)
APCI-MASS: m/z=382 (M+H)$^+$ Preparation 49
4-[4-(4-Hexyloxyphenyl)-1,2,3,6-tetrahydropyridin-1-yl]benzoic acid
IR (KBr): 1668.1, 1602.6, 1513.8, 1230.4 cm$^{-1}$
NMR (DMSO-d$_6$, δ): 0.88 (3H, m), 1.2–1.5 (6H, m), 1.6–1.8 (2H, m), 2.5–2.7 (2H, m), 3.5–3.7 (2H, m), 3.8–4.1 (4H, m), 6.18 (1H, m), 6.90 (2H, d, J=8.8 Hz), 6.97 (2H, d, J=8.0 Hz), 7.40(2H, d, J=8.8 Hz), 7.78 (2H, d, J=8.0 Hz)
APCI-MASS: m/z=380 (M+H)$^+$ Preparation 50
4-(4-n-Pentyloxyphenylethynyl)benzoic acid
IR (KBr): 2958, 2931, 1685, 1598, 1513, 1425, 1286, 1247 cm$^{-1}$ NMR (DMSO-d₆, δ): 0.90 (3H, t, J=7.0 Hz), 1.3–1.5 (4H, m), 1.7–1.9 (2H, m), 4.01 (2H, t, J=6.5 Hz), 6.99 (2H, d, J=8.8 Hz), 7.51 (2H, d, J=8.8 Hz), 7.62 (2H, d, J=8.3 Hz), 7.95 (2H, d, J=8.3 Hz), 13.1 (1H, br s)

APCI-MASS: m/z=309 (M+H)⁺

Preparation 51

4-[5-[2-(4-n-Hexyloxyphenyl)ethyl]-1,3,4-thiadiazol-2-yl]benzoic acid

IR (KBr): 2935, 1679, 1513, 1241 cm⁻¹

NMR (DMSO-d₆, δ): 0.87 (3H, t, J=6.5 Hz), 1.2–1.5 (6H, m), 1.6–1.8 (2H, m), 3.03 (2H, t, J=7.5 Hz), 3.44 (2H, t, J=7.5 Hz), 3.91 (2H, t, J=6.5 Hz), 6.84 (2H, d, J=8.6 Hz), 7.18 (2H, d, J=8.6 Hz), 8.03 (2H, d, J=8.9 Hz), 8.08 (2H, d, J=8.9 Hz)

APCI-MASS: m/z=411 (M+H)⁺

Preparation 52

4-[5-(4-n-Pentylphenyl)-1,3,4-thiadiazol-2-yl]benzoic acid

IR (KBr): 2954, 2923, 2854, 1685, 1604, 1429, 1288 cm⁻¹

NMR (DMSO-d₆, δ): 0.87 (3H, t, J=6.6 Hz), 1.2–1.4 (4H, m), 1.5–1.7 (2H, in), 2.67 (2H, t, J=7.6 Hz), 7.42 (2H, d, J=8.2 Hz), 7.95 (2H, d, J=8.2 Hz), 8.11 (4H, s)

APCI-MASS: m/z=353 (M+H)⁺

Preparation 53

4-[5-(4-n-Hexylphenyl)-1,3,4-thiadiazol-2-yl]benzoic acid

IR (KBr): 2954, 2921, 2852, 1685, 1429, 1290 cm⁻¹

NMR (DMSO-d₆, δ): 0.93 (3H, t, J=6.7 Hz), 1.2–1.8 (8H, m), 2.73 (2H, t, J=7.7 Hz), 7.48 (2H, d, J=8.2 Hz), 8.01 (2H, d, J=8.1 Hz), 8.19 (4H, s)

APCI-MASS: m/z=367 (M+H)⁺

Preparation 54

4-[5-(4-n-Heptyloxyphenyl)-1,3,4-thiadiazol-2-yl]benzoic acid

IR (KBr): 2923, 2856, 1689, 1604, 1430, 1292, 1250 cm⁻¹

NMR (DMSO-d₆, δ): 0.88 (3H, t, J=6.5 Hz), 1.2–1.5 (8H, m), 1.6–1.8 (2H, m), 4.07 (2H, t, J=6.5 Hz), 7.13 (2H, d, J=8.8 Hz), 7.97 (2H, d, J=8.8 Hz), 8.12 (4H, s)

APCI-MASS: m/z=397 (M+H)⁺

Preraration 55

4-[5-(4-n-Butoxyphenyl)-1,3,4-thiadiazol-2-yl]benzoic acid

IR (KBr): 2958, 2869, 1687, 1604, 1432, 1294, 1251, 1174 cm⁻¹

NMR (DMSO-d₆, δ): 0.95 (3H, t, J=7.3 Hz), 1.4–1.6 (2H, m), 1.7–1.9 (2H, m), 4.08 (2H, t, J=7.4 Hz), 7.13 (2H, d, J=8.8 Hz), 7.97 (2H, d, J=8.8 Hz), 8.12 (4H, s)

APCI-MASS: m/z=355 (M+H)⁺

Preparation 56

4-[5-(4-Methoxyphenyl)-1,3,4-thiadiazol-2-yl]benzoic acid

IR (KBr): 1687, 1604, 1517, 1430, 1292, 1253, 1178 cm⁻¹

NMR (DMSO-d₆, δ): 3.86 (3H, s), 7.14 (2H, d, J=8.9 Hz), 7.98 (2H, d, J=8.9 Hz), 8.12 (4H, s), 13.26 (1H, br s)

APCI-MASS: m/z=313 (M+H)⁺

Preparation 57

4-[5-[4-(3-Phenoxypropyloxy)phenyl]-1,3,4-thiadiazol-2-yl]benzoic acid

IR (KBr): 2948, 1689, 1602, 1411, 1292, 1243, 1174 cm⁻¹

NMR (DMSO-d₆, δ): 2.22 (2H, tt, J=6.2 and 6.2 Hz), 4.15 (2H, t, J=6.2 Hz), 4.26 (2H, t, J=6.2 Hz), 6.9–7.0 (3H, m), 7.17 (2H, d, J=8.9 Hz), 7.2–7.4 (2H, m), 7.98 (2H, d, J=8.9 Hz), 8.12 (4H, s)

APCI-MASS: m/z=433 (M+H)⁺

Preparation 58

4-[5-(1-n-Octylpiperidin-4-yl)-1,3,4-thiadiazol-2-yl]benzoic acid hydrochloride

IR (KBr): 2933, 2871, 1714, 1438, 1278, 1110 cm⁻¹

NMR (DMSO-d₆, δ): 0.87 (3H, t, J=0.9 Hz), 1.2–1.5 (10H, m), 1.6–2.4 (4H, m), 3.0–3.2 (2H, m), 3.3–3.4 (1H, m), 3.4–4.0 (4H, m), 8.10 (4H, s), 11.67 (1H, s)

APCI-MASS: m/z=402 (M+H)⁺

Preparation 59

4-[5-(4-n-Pentyloxyphenyl)thiophen-2-yl]benzoic acid

IR (KBr): 2956, 2935, 2867, 1685, 1604, 1288, 1251, 1182 cm⁻¹

NMR (DMSO-d₆, δ): 0.90 (3H, t, J=6.9 Hz), 1.3–1.5 (4H, m), 1.6–1.8 (2H, m), 4.01 (2H, t, J=6.5 Hz), 6.98 (2H, d, J=8.8 Hz), 7.41 (1H, d, J=3.5 Hz), 7.5–7.7 (3H, m), 7.78 (2H, d, J=8.5 Hz), 7.95 (2H, d, J=8.5 Hz)

APCI-MASS: m/z=367 (M+H)⁺

Preparation 60

4-[5-(4-n-Pentyloxyphenyl)furan-2-yl]benzoic acid

IR (KBr): 2958, 2935, 1681, 1608, 1538, 1294, 1253 cm⁻¹

NMR (DMSO-d₆, δ): 0.91 (3H, t, J=6.9 Hz), 1.3–1.5 (4H, m), 1.6–1.8 (2H, m), 4.01 (2H, t, J=6.4 Hz), 6.96 (1H, d, J=3.5 Hz), 7.02 (2H, d, J=8.8 Hz), 7.19 (1H, d, J=3.5 Hz), 7.76 (2H, d, J=8.8 Hz), 7.85 (2H, d, J=8.5 Hz), 7.98 (2H, d, J=8.5 Hz)

APCI-MASS: m/z=351 (M+H)⁺

Preparation 61

To a suspension of 3-(4-n-hexyloxyphenyl)propionohydrazide (0.92 g) in tetrahydrofuran (25 ml) and pyridine (0.84 ml) was added a solution of 4-methoxycarbonylbenzoyl chloride (0.73 g) in tetrahydrofuran (10 ml) dropwise at 5° C. The reaction mixture was stirred for 1 hour and poured into ice-water. The precipitate was collected by filtration, washed with water and dried under reduced pressure to give 1-[3-(4-n-hexyloxyphenyl)propanoyl]-2-(4-methoxycarbonylbenzoyl)hydrazine (1.43 g).

IR (KBr): 3234, 2929, 1724, 1689, 1646, 1515, 1282, 1108 cm⁻¹

NMR (DMSO-d₆, δ): 0.87 (3H, t, J=6.4 Hz), 1.3–1.5 (6H, m), 1.6–1.8 (2H, m), 2.4–2.5 (2H, m), 2.81 (2H, d, J=7.7 Hz), 3.89 (3H, s), 3.91 (2H, t, J=6.5 Hz), 6.83 (2H, d, J=8.6 Hz), 7.15 (2H, d, J=8.6 Hz), 7.98 (2H, d, J=8.5 Hz), 8.07 (2H, d, J=8.5 Hz), 9.97 (1H, s), 10.51 (1H, s)

APCI-MASS: m/z=427 (M+H)⁺

The following compounds [Preparations 62 to 68] were obtained according to a similar manner to that of Preparation 61.

Preparation 62

1-(4-Methoxycarbonylbenzoyl)-2-(4-n-pentylbenzoyl)hydrazine

IR (KBr): 2958, 2929, 1724, 1685, 1646, 1282 cm⁻¹

NMR (DMSO-d₆, δ): 0.86 (3H, t, J=6.7 Hz), 1.2–1.4 (4H, m), 1.5–1.7 (2H, m), 2.65 (2H, t, J=6.8 Hz), 3.90 (3H, s), 7.34 (2H, d, J=8.1 Hz), 7.84 (2H, d, J=8.1 Hz), 8.05 (2H, d, J=3.4 Hz), 8.07 (2H, d, J=3.4 Hz), 10.50 (1H, s), 10.69 (1H, s)

APCI-MASS: m/z=369 (M+H)⁺

Preparation 63

1-[N-(tert-Butoxycarbonyl)piperidin-4-yl)carbonyl]-2-(4-methoxycarbonylbenzoyl)hydrazine IR (KBr): 3291, 2940, 1727, 1664, 1540, 1436, 1278 cm⁻¹

NMR (DMSO-d₆, δ): 1.41 (9H, s), 1.4–1.9 (4H, m), 2.3–2.5 (1H, m), 2.79 (2H, t, J=11.5 Hz), 3.89 (3H, s), 3.96 (2H, d, J=13.5 Hz), 7.97 (2H, d, J=8.6 Hz), 8.06 (2H, d, J=8.6 Hz), 9.96 (1H, s), 10.50 (1H, s)

APCI-MASS: m/z=306 (M−Boc)⁺

Preparation 64

1-(4-Methoxycarbonylbenzoyl)-2-[4-(3-phenoxypropyloxy)-benzoyl]hydrazine

IR (KBr): 3228, 2950, 2883, 1722, 1685, 1645, 1604, 1465, 1280, 1247 cm$^{-1}$

NMR (DMSO-d$_6$, δ): 2.21 (2H, tt, J=6.2 and 6.2 Hz), 3.91 (3H, s), 4.15 (2H, t, J=6.2 Hz), 4.23 (2H, t, J=6.2 Hz), 6.9–7.1 (3H, m), 7.08 (2H, d, J=8.8 Hz), 7.29 (2H, dd, J=8.8 and 7.2 Hz), 7.91 (2H, d, J=8.8 Hz), 8.03 (2H, d, J=8.6 Hz), 8.10 (2H, d, J=8.6 Hz), 10.42 (1H, S), 10.63 (1H, s)

APCI-MASS: m/z=449 (M+H)$^+$

Preparation 65

1-(4-Methoxybenzoyl)-2-(4-methoxycarbonylbenzoyl)-hydrazine

IR (KBr): 3267, 3068, 1722, 1679, 1643, 1610, 1558, 1506, 1284, 1257 cm$^{-1}$

NMR (DMSO-d$_6$, δ): 3.84 (3H, s), 3.90 (3H, s), 7.06 (2H, d, J=8.9 Hz), 7.92 (2H, d, J=8.9 Hz), 8.03 (2H, d, J=8.7 Hz), 8.10 (2H, d, J=8.7 Hz), 10.42 (1H, s), 10.63 (1H, s)

APCI-MASS: m/z=329 (M+H)$^+$

Preparation 66

1-(4-n-Butoxybenzoyl)-2-(4-methoxycarbonylbenzoyl)-hydrazine

IR (KBr): 3305, 2956, 1724, 1683, 1643, 1610, 1284, 1251, 1184, 1108 cm$^{-1}$

NMR (DMSO-d$_6$, δ): 0.94 (3H, t, J=7.3 Hz), 1.4–1.6 (2H, m), 1.6–1.8 (2H, m), 3.90 (3H, s), 4.06 (2H, t, J=6.4 Hz), 7.05 (2H, d, J=8.8 Hz), 7.90 (2H, d, J=8.8 Hz), 8.03 (2H, d, J=8.6 Hz), 8.10 (2H, d, J=8.6 Hz), 10.42 (1H, s), 10.64 (1H, s)

APCI-MASS: m/z=371 (M+H)$^+$

Preparation 67

1-(4-n-Heptyloxybenzoyl)-2-(4-methoxycarbonylbenzoyl)-hydrazine

IR (KBr): 3237, 2929, 2858, 1726, 1683, 1643, 1610, 1284, 1253 cm$^{-1}$

NMR (DMSO-d$_6$, δ): 0.87 (3H, t, J=6.5 Hz), 1.2–1.5 (8H, m), 1.6–1.8 (2H, m), 3.90 (3H, s), 4.04 (2H, d, J=6.4 Hz), 7.04 (2H, d, J=8.8 Hz), 7.90 (2H, d, J=8.8 Hz), 8.03 (2H, d, J=8.6 Hz), 8.10 (2H, d, J=8.6 Hz), 10.42 (1H, s), 10.64 (1H, s)

APCI-MASS: m/z=413 (M+H)$^+$

Preparation 68

1-(4-n-Hexylbenzoyl)-2-(4-methoxycarbonylbenzoyl)-hydrazine

IR (KBr): 3330, 2958, 2925, 2854, 1726, 1685, 1647, 1282, 1108 cm$^{-1}$

NMR (DMSO-d$_6$, δ): 0.86 (3H, t, J=6.6 Hz), 1.2–1.4 (6H, m), 1.5–1.7 (2H, m), 2.65 (2H, t, J=7.5 Hz), 3.90 (3H, s), 7.34 (2H, d, J=8.2 Hz), 7.84 (2H, d, J=8.2 Hz), 8.0–8.2 (4H, m), 10.50 (1H, s), 10.68 (1H, s)

APCI-MASS: m/z=383 (M+H)$^+$

Preparation 69

A suspension of 1-[3-(4-n-hexyloxyphenyl)propanoyl]-2-(4-methoxycarbonylbenzoyl)hydrazine (1.0 g) and diphosphorus pentasulfide (730 mg) in tetrahydrofuran (20 ml) was stirred for 1 hour at 60° C. To a reaction mixture was added water and the mixture was stirred for 1 hour at room temperature. The precipitate was collected by filtration, washed with water and dried under reduced pressure to give methyl 4-[5-[2-(4-n-hexyloxyphenyl)ethyl]-1,3,4-thiadiazol-2-yl]benzoate (883 mg).

IR (KBr): 2927, 1724, 1513, 1280, 1108 cm$^{-1}$

NMR (CDCl$_3$, δ): 0.90 (3H, t, J=6.5 Hz), 1.2–1.6 (6H, m), 1.7–1.9 (2H, m), 3.11 (2H, t, J=7.6 Hz), 3.46 (2H, t, J=7.6 Hz), 3.93 (2H, t, J=6.5 Hz), 3.95 (3H, s), 6.84 (2H, d, J=8.6 Hz), 7.14 (2H, d, J=8.6 Hz), 7.98 (2H, d, J=8.4 Hz), 8.12 (2H, d, J=8.4 Hz)

APCI-MASS: m/z=425 (M+H)$^+$

The following compounds [Preparations 70 to 76] were obtained according to a similar manner to that of Preparation 69.

Preparation 70

Methyl 4-[5-(4-n-pentylphenyl)-1,3,4-thiadiazol-2-yl]-benzoate

IR (KBr): 2956, 2929, 2856, 1722, 1434, 1280, 1110 cm$^{-1}$

NMR (CDCl$_3$, δ): 0.91 (3H, t, J=6.7 Hz), 1.2–1.4 (4H, m), 1.5–1.7 (2H, m), 2.68 (2H, t, J=7.7 Hz), 3.96 (3H, s), 7.31 (2H, d, J=8.3 Hz), 7.92 (2H, d, J=8.3 Hz), 8.07 (2H, d, J=8.0 Hz), 8.16 (2H, d, J=8.0 Hz)

APCI-MASS: m/z=367 (M+H)$^+$

Preparation 71

Methyl 4-[5-[N-(tert-butoxycarbonyl)piperidin-4-yl]-1,3,4-thiadiazol-2-yl]benzoate IR (KBr): 2975, 1716, 1691, 1403, 1276, 1238, 1174, 1112 cm$^{-1}$ NMR (CDCl$_3$, δ): 1.49 (9H, s), 1.7–1.9 (2H, m), 2.1–2.2 (2H, m), 2.8–3.0 (2H, m), 3.3–3.5 (1H, m), 3.96 (3H, s), 4.22 (2H, d, J=13.3 Hz), 8.01 (2H, d, J=8.8 Hz), 8.14 (2H, d, J=8.8 Hz)

APCI-MASS: m/z=304 (M−Boc)$^+$

Preparation 72

Methyl 4-[5-[4-(3-phenoxypropyloxy)phenyl]-1,3,4-thiadiazol-2-yl]benzoate

IR (KBr): 2954, 1727, 1602, 1436, 1284, 1251, 1182 cm$^{-1}$

NMR (CDCl$_3$, δ): 2.30 (2H, tt, J=6.1 and 6.1 Hz), 3.96 (3H, s), 4.18 (2H, t, J=6.1 Hz), 4.25 (2H, t, J=6.1 Hz), 6.9–7.0 (3H, m), 7.02 (2H, d, J=8.8 Hz), 7.2–7.4 (2H, m), 7.95 (2H, d, J=8.5 Hz), 8.06 (2H, d, J=8.6 Hz), 8.15 (2H, d, J=8.6 Hz)

APCI-MASS: m/z=447 (M+H)$^+$

Preparation 73

Methyl 4-[5-(4-methoxyphenyl)-1,3,4-thiadiazol-2-yl]-benzoate

IR (KBr): 2952, 1710, 1606, 1517, 1432, 1278, 1251, 1180, 1110 cm$^{-1}$

NMR (CDCl$_3$, δ): 3.88 (3H, s), 3.95 (3H, s), 6.98 (2H, d, J=8.8 Hz), 7.94 (2H, d, J=8.8 Hz), 8.07 (2H, d, J=8.6 Hz), 8.13 (2H, d, J=8.6 Hz)

APCI-MASS: m/z=327 (M+H)$^+$

Preparation 74

Methyl 4-[5-(4-n-butoxyphenyl)-1,3,4-thiadiazol-2-yl]-benzoate

IR (KBr): 2962, 2942, 2873, 1718, 1606, 1436, 1280, 1251, 1180 cm$^{-1}$

NMR (CDCl$_3$, δ): 1.00 (3H, t, J=7.3 Hz), 1.4–1.6 (2H, m), 1.7–1.9 (2H, m), 3.95 (3H, s), 4.03 (2H, t, J=6.5 Hz), 6.99 (2H, d, J=8.9 Hz), 7.94 (2H, d, J=8.9 Hz), 8.06 (2H, d, J=8.6 Hz), 8.15 (2H, d, J=8.6 Hz)

APCI-MASS: m/z=369 (M+H)$^+$

Preparation 75

Methyl 4-[5-(4-n-heptyloxyphenyl)-1,3,4-thiadiazol-2-yl]benzoate

IR (KBr): 2933, 2861, 1718, 1515, 1434, 1278, 1106 cm$^{-1}$

NMR (CDCl$_3$, δ): 0.90 (3H, t, J=6.5 Hz), 1.3–1.6 (8H, m), 1.8–2.0 (2H, m), 3.95 (3H, s), 4.03 (2H, t, J=6.5 Hz), 6.99 (2H, d, J=8.8 Hz), 7.94 (2H, d, J=8.8 Hz), 8.06 (2H, d, J=8.6 Hz), 8.15 (2H, d, J=8.6 Hz)

APCI-MASS: m/z=411 (M+H)$^+$

Preparation 76

Methyl 4-[5-(4-n-hexylphenyl)-1,3,4-thiadiazol-2-yl]-benzoate

IR (KBr): 2925, 2854, 1720, 1432, 1280, 1110 cm$^{-1}$

NMR (CDCl$_3$, δ): 0.89 (3H, t, J=6.6 Hz), 1.3–1.7 (6H, m), 2.67 (2H, t, J=7.7 Hz), 3.96 (3H, s), 7.31 (2H, d, J=8.3 Hz), 7.92 (2H, d, J=8.3 Hz), 8.07 (2H, d, J=8.6 Hz), 8.16 (2H, d, J=8.6 Hz)

APCI-MASS: m/z=381 (M+H)$^+$

Preparation 77

To a solution of 1-hydroxybenzotriazole (5.35 g) and 4-[4-(4-hexyloxyphenyl)piperazin-1-yl]benzoic acid hydrochloride (15 g) in the mixture of triethylamine (9.64 ml) and dichloromethane (450 ml) was added 1-ethyl-3-(3'-dimethylaminopropyl) carbodiimide hydrochloride (WSCD.HCl) (12.6 g) and stirred for 4 hours at ambient temperature. The reaction mixture was added to water. The organic layer was taken and dried over magnesium sulfate. Magnesium sulfate was filtered off, and the filtrate was evaporated under reduced pressure to give 1-[4-[4-(4-hexyloxyphenyl)piperazin-1-yl]benzoyloxy]benzotriazole (16.78 g).

IR (KBr): 1783.8, 1600.6, 1511.9, 1232.3, 1184.1 cm$^{-1}$

NMR (CDCl$_3$, δ): 0.91 (3H, t, J=6.5 Hz), 1.2–1.6 (6H, m), 1.7–1.9 (2H, m), 3.1–3.3 (4H, m), 3.5–3.7 (4H, m), 3.93 (2H, t, J=6.5 Hz), 6.87 (2H, d, J=9.2 Hz), 6.95 (2H, d, J=9.2 Hz), 7.00 (2H, d, J=9.2 Hz), 7.35–7.6 (3H, m), 8.09 (1H, d, J=8.2 Hz), 8.15 (2H, d, J=9.2 Hz)

The following compounds [Preparations 78 to 97] were obtained according to a similar manner to that of Preparation 77.

Preparation 78

1-[4-[4-(trans-4-Cyclohexylcyclohexyl)piperazin-1-yl]-benzoyloxy]benzotriazole

IR (KBr): 2925.5, 1764.5, 1600.6, 1234.2 cm$^{-1}$

NMR (CDCl$_3$, δ): 0.8–1.4 (12H, m), 1.5–2.1 (8H, m), 2.27 (1H, m), 2.6–2.8 (4H, m), 3.4–3.6 (4H, m), 6.93 (2H, d, J=9.1 Hz), 7.3–7.6 (3H, m), 8.08 (1H, d, J=8.1 Hz), 8.11 (2H, d, J=9.1 Hz)

APCI-MASS: m/z=488 (M+H)$^+$

Preparation 79

1-[4-[4-(cis-4-Cyclohexylcyclohexyl)piperazin-1-yl]-benzoyloxy]benzotriazole

IR (KBr): 1762.6, 1600.6, 1232.3, 1186.0 cm$^{-1}$

NMR (CDCl$_3$, δ): 0.8–2.0 (20H, m), 2.26 (1H, m), 2.6–2.8 (4H, m), 3.4–3.6 (4H, m), 6.94 (2H, d, J=9.0 Hz), 7.35–7.6 (3H, m), 8.08 (1H, d, J=8.1 Hz), 8.11 (2H, d, J=9.0 Hz)

APCI-MASS: m/z=488 (M+H)$^+$

Preparation 80

1-[4-[4-(4-Cyclohexyloxyphenyl)piperazin-1-yl]-benzoyloxy]benzotriazole

Preparation 81

1-[4-[4-(4-Morpholinophenyl)piperazin-1-yl]benzoyloxy]-benzotriazole

IR (KBr): 1780.0, 1600.6, 1513.8, 1232.3, 1184.1 cm$^{-1}$

NMR (CDCl$_3$, δ): 3.09 (4H, t, J=4.8 Hz), 3.26 (4H, t, J=5.1 Hz), 3.62 (4H, t, J=5.1 Hz), 3.87 (4H, t, J=4.8 Hz), 6.91 (2H, d, J=9.0 Hz), 7.00 (2H, d, J=9.0 Hz), 7.35–7.6 (3H, m), 8.09 (1H, d, J=7.1 Hz), 8.15 (2H, d, J=9.1 Hz)

Preparation 82

1-[4-[4-(4-Hexyloxyphenyl)-4-hydroxypiperidin-1-yl]-benzoyloxy]benzotriazole

IR (KBr): 3513.7, 1733.7, 1598.7, 1186.0 cm$^{-1}$

NMR (CDCl$_3$, δ): 0.91 (3H, t, J=6.5 Hz), 1.2–2.05 (11H, m), 2.05–2.3 (2H, m), 3.4–3.6 (2H, m), 3.8–4.0 (2H, m), 3.96 (2H, t, J=6.5 Hz), 6.90'(2H, d, J=8.8 Hz), 7.00 (2H, d, J=9.2 Hz), 7.3–7.6 (5H, m), 8.07 (1H, d, J=8.2 Hz), 8.12 (2H, d, J=9.2 Hz)

APCI-MASS: m/z=515 (M+H)$^+$

Preparation 83

1-[4-[4-(4-Hexyloxyphenyl)piperidin-1-yl]benzoyloxy]-benzotriazole

IR (KBr): 2933.2, 1768.4, 1602.6, 1515.8, 1259.3, 1186.0 cm$^{-1}$

NMR (CDCl$_3$, δ): 0.90 (3H, t, J=6.5 Hz), 1.2–1.6 (6H, m), 1.7–2.1 (6H, m), 2.65–2.9 (1H, m), 3.0–3.2 (2H, m), 3.94 (2H, t, J=6.5 Hz), 4.05–4.2 (2H, m), 6.86 (2H, d, J=8.7 Hz), 6.98 (2H d, J=9.1 Hz), 7.14 (2H, d, J=8.7 Hz), 7.35–7.6 (3H, m), 8.08 (1H, d, J=8.2 Hz), 8.12 (2H, d, J=9.1 Hz)

Preparation 84

1-[4-[4-(4-Pentyloxyphenyl)phenyl]benzoyloxy]-benzotriazole

Preparation 85

1-[4-[4-(3-Hexyloxyphenyl)piperazin-1-yl]benzoyloxy]-benzotriazole

IR (KBr): 1774.2, 1602.6, 1236.1, 1187.9 cm$^{-1}$

NMR (CDCl$_3$, δ): 0.91 (3H, t, J=6.6 Hz), 1.2–1.6 (6H, m), 1.7–1.9 (2H, m), 3.3–3.5 (4H, m), 3.5–3.7 (4H, m), 3.96 (2H, t, J=6.5 Hz), 6.47 (1H, d, J=8.0 Hz), 6.51 (1H, s), 6.56 (1H, d, J=8.0 Hz), 6.98 (2H, d, J=9.0 Hz), 7.20 (1H, dd, J=8.0 Hz), 7.3–7.6 (3H, m), 8.08 (1H, d, J=8.2 Hz), 8.15 (2H, d, J=9.0 Hz)

Preparation 86

1-[4-[4-(4-Hexyloxyphenyl)-1,2,3,6-tetrahydropyridin-1-yl]benzoyloxy]benzotriazole IR (KBr): 1766.5, 1600.6, 1513.8, 1232.3, 1182.2 cm$^{-1}$ NMR (CDCl$_3$, δ): 0.91 (3H, t, J=6.5 Hz), 1.2–1.6 (6H, m), 1.6–1.9 (2H, m), 2.6–2.8 (2H, m), 3.75 (2H, t, J=5.7 Hz), 3.97 (2H, t, J=6.5 Hz), 4.05–4.2 (2H, m), 6.0–6.15 (1H, m), 6.89 (2H, d, J=8.8 Hz), 6.96 (2H, d, J=9.1 Hz), 7.35 (2H, d, J=8.8 Hz), 7.3–7.6 (3H, m), 8.08 (1H, d, J=8.2 Hz), 8.14 (2H, d, J=9.1 Hz)

Preparation 87

1-[4-[4-(1-Cyclohexylpiperidin-4-yl)piperidin-1-yl]-benzoyloxy]benzotriazole

IR (KBr): 1766.5, 1606, 1240, 1186.0, 918.0 cm$^{-1}$

NMR (CDCl$_3$, δ): 1.0–2.5 (23H, m), 2.8–3.2 (4H, m), 3.9–4.1 (2H, m), 6.92 (2H, d, J=9.1 Hz), 7.3–7.6 (3H, m), 8.0–8.2 (3H, m)

APCI-MASS: m/z=488 (M+H)$^+$

Preparation 88

1-[4-[5-[2-(4-n-Hexyloxyphenyl)ethyl]-1,3,4-thiadiazol-2-yl]benzoyloxy]benzotriazole IR (KBr): 2942, 2865, 1785, 1513, 1240, 995 cm$^{-1}$ NMR (CDCl$_3$, δ): 0.90 (3H, t, J=6.6 Hz), 1.2–1.5 (6H, m), 1.7–1.9 (2H, m), 3.14 (2H, t, J=7.6 Hz), 3.50 (2H, t, J=7.6 Hz), 3.94 (2H, t, J=6.5 Hz), 6.85 (2H, d, J=8.6 Hz), 7.15 (2H, d, J=8.6 Hz), 7.4–7.6 (3H, m), 8.1–8.2 (1H, m), 8.16 (2H, d, J=8.6 Hz), 8.38 (2H, d, J=8.6 Hz)

APCI-MASS: m/z=528 (M+H)$^+$

Preparation 89

1-[4-[5-(4-n-Pentylphenyl)-1,3,4-thiadiazol-2-yl]-benzoyloxy]benzotriazole

IR (KBr): 2956, 2929, 2865, 1776, 1608, 1434, 1402, 1232 cm$^{-1}$

NMR (CDCl$_3$, δ): 0.91 (3H, t, J=6.6 Hz), 1.2–1.4 (4H, m), 1.5–1.7 (2H, m), 2.70 (2H, t, J=7.7 Hz), 7.34 (2H, d, J=8.3 Hz), 7.4–7.6 (3H, m), 7.96 (2H, d, J=8.3 Hz), 8.12 (1H, d, J=9.1 Hz), 8.26 (2H, d, J=8.7 Hz), 8.41 (2H, d, J=8.7 Hz)

APCI-MASS: m/z=470 (M+H)$^+$

Preparation 90

1-[4-[5-(4-n-Hexylphenyl)-1,3,4-thiadiazol-2-yl]-benzoyloxy]benzotriazole

IR (KBr): 2956, 2925, 2856, 1770, 1606, 1434, 1232, 1029 cm$^{-1}$

NMR (CDCl$_3$, δ): 0.90 (3H, t, J=6.6 Hz), 1.2–1.5 (6H, m), 1.6–1.8 (2H, m), 2.69 (2H, t, J=7.7 Hz), 7.33 (2H, d, J=8.3 Hz), 7.4–7.6 (3H, m), 7.95 (2H, d, J=8.3 Hz), 8.12 (1H, d, J=8.1 Hz), 8.25 (2H, d, J=8.7 Hz), 8.40 (2H, d, J=8.7 Hz)

APCI-MASS: m/z=484 (M+H)$^+$

Preparation 91
1-[4-[5-(4-n-Heptyloxyphenyl)-1,3,4-thiadiazol-2-yl]-benzoyloxy]benzotriazole IR (KBr): 2925, 2856, 1770, 1602, 1440, 1263, 1222, 1029 cm$^{-1}$ NMR (CDCl$_3$, δ): 0.91 (3H, t, J=6.5 Hz), 1.2–1.6 (8H, m), 1.7–1.9 (2H, m), 4.04 (2H, t, J=6.5 Hz), 7.01 (2H, d, J=8.8 Hz), 7.4–7.7 (3H, m), 7.97 (2H, d, J=8.8 Hz), 8.12 (1H, d, J=8.2 Hz), 8.24 (2H, d, J=8.6 Hz), 8.40 (2H, d, J=8.6 Hz)

APCI-MASS: m/z=514 (M+H)$^+$

Preparation 92
1-[4-[5-(4-n-Butoxyphenyl)-1,3,4-thiadiazol-2-yl]-benzoyloxy]benzotriazole IR (KBr): 2956, 2873, 1774, 1602, 1442, 1251, 1180 cm$^{-1}$ NMR (CDCl$_3$, δ): 1.00 (3H, t, J=7.2 Hz), 1.5–1.7 (2H, m), 1.7–1.9 (2H, m), 4.06 (2H, t, J=6.7 Hz), 7.02 (2H, d, J=8.7 Hz), 7.4–7.6 (3H, m), 7.98 (2H, d, J=8.7 Hz), 8.13 (1H, d, J=8.0 Hz), 8.25 (2H, d, J=8.2 Hz), 8.41 (2H, d, J=8.2 Hz)

APCI-MASS: m/z=472 (M+H)$^+$

Preparation 93
1-[4-[5-(4-Methoxyphenyl)-1,3,4-thiadiazol-2-yl]-benzoyloxy]benzotriazole NMR (CDCl$_3$, δ): 3.91 (3H, s), 7.04 (2H, d, J=8.9 Hz), 7.2–7.5 (3H, m), 8.00 (2H, d, J=8.9 Hz), 8.13 (1H, d, J=8.1 Hz), 8.25 (2H, d, J=8.7 Hz), 8.42 (2H, d, J=8.7 Hz)

Preparation 94
1-[4-[5-[4-(3-Phenoxypropyloxy)phenyl]-1,3,4-thiadiazol-2-yl]benzoyloxy]benzotriazole IR (KBr): 2927, 1778, 1603, 1438, 1240, 1178 cm$^{-1}$ NMR (CDCl$_3$, δ): 2.31 (2H, tt, J=6.0 and 6.0 Hz), 4.19 (2H, t, J=6.0 Hz), 4.27 (2H, t, J=6.0 Hz), 6.93 (2H, d, J=8.8 Hz), 7.0–7.2 (3H, m), 7.2–7.6 (5H, m), 7.98 (2H, d, J=8.8 Hz), 8.13 (1H, d, J=8.3 Hz), 8.25 (2H, d, J=8.3 Hz), 8.41 (2H, d, J=8.3 Hz)

APCI-MASS: m/z=550 (M+H)$^+$

Preparation 95
1-[4-[5-(1-n-Octylpiperidin-4-yl)-1,3,4-thiadiazol-2-yl]benzoyloxy]benzotriazole IR (KBr): 3421, 2925, 2856, 1697, 1452, 1380, 1259, 1099 cm$^{-1}$ NMR (CDCl$_3$, δ): 0.89 (3H, t, J=6.8 Hz), 1.2–1.7 (12H, m), 1.9–2.5 (10H, m), 3.0–3.2 (2H, m), 3.2–3.4 (1H, m), 7.4–7.6 (3H, m), 8.12 (1H, d, J=8.1 Hz), 8.20 (2H, d, J=8.6 Hz), 8.39 (2H, d, J=8.6 Hz)

APCI-MASS: m/z=519 (M+H)$^+$

Preparation 96
1-[4-[5-(4-n-Pentyloxyphenyl)thiophen-2-yl]benzoyloxy]-benzotriazole IR (KBr): 2865, 1772, 1691, 1600, 1540, 1513, 1454, 1251, 1180 cm$^{-1}$ NMR (CDCl$_3$, δ): 0.95 (3H, t, J=7.2 Hz), 1.3–1.6 (4H, m), 1.7–2.0 (2H, m), 4.00 (2H, t, J=6.4 Hz), 6.94 (2H, d, J=8.4 Hz), 7.25 (1H, d, J=3.5 Hz), 7.4–7.7 (6H, m), 7.81 (2H, d, J=8.1 Hz), 8.11 (1H, d, J=8.4 Hz), 8.27 (2H, d, J=8.1 Hz)

APCI-MASS: m/z=484 (M+H)$^+$

Preparation 97
1-[4-[5-(4-n-Pentyloxyphenyl)furan-2-yl]benzoyloxy]-benzotriazole IR (KBr): 2948, 2865, 1778, 1600, 1502, 1479, 1253 cm$^{-1}$ NMR (CDCl$_3$, δ): 0.95 (3H, t, J=7.2 Hz), 1.3–1.6 (4H, m), 1.7–1.9 (2H, m), 4.01 (2H, t, J=6.5 Hz), 6.68 (1H, d, J=3.6 Hz), 6.9–7.1 (3H, m), 7.4–7.6 (3H, m), 7.71 (2H, d, J=8.8 Hz), 7.90 (2H, d, J=8.7 Hz), 8.11 (1H, d, J=8.2 Hz), 8.28 (2H, d, J=8.7 Hz)

APCI-MASS: m/z=468 (M+H)$^+$

Preparation 98
To a solution of 4-n-pentyloxybenzoic acid benzotriazole-1-yl ester (20 g) in N,N-dimethylformamide (100 ml) was added thiosemicarbazide (6.73 g) and stirred for 7 hours at ambient temperature. The reaction mixture was pulverized with diisopropyl ether. The precipitate was collected by filtration to give 1-(4-n-pentyloxybenzoyl)-3-thiosemicarbazide (20 g).

IR (KBr): 3419.2, 3151.1, 1691.3, 1259.3 cm$^{-1}$

NMR (DMSO-d$_6$, δ): 0.90 (3H, t, J=7.0 Hz), 1.2–1.5 (4H, m), 1.6–1.8 (2H, m), 4.02 (2H, t, J=6.5 Hz), 6.98 (2H, d, J=8.8 Hz), 7.58 (2H, s), 9.28 (1H, s), 10.22 (1H, s)

APCI-MASS: m/z=282 (M+H)$^+$

Preparation 99
To a slurry of 1-(4-n-pentyloxybenzoyl)-3-thiosemicarbazide (20 g) in toluene (213.3 ml) at 40° C., was added dropwise over 30 minutes, methanesulfonic acid (6.92 ml). The mixture was refluxed for 12 hours. After cooling to 10° C, the resulting precipitate was filtered and dried. The precipitate was dissolved in water, the solution was adjusted to pH 9 with 1N sodium hydroxide and extracted with ethyl acetate. The organic layer was separated, washed with brine, dried over magnesium sulfate and evaporated under reduced pressure to give 2-amino-5-(4-n-pentyloxyphenyl)-1,3,4-thiadiazole (4.314 g).

IR (KBr): 3261.0, 3174.3, 1608.3, 1255.4 cm$^{-1}$

NMR (CDCl$_3$, δ): 0.94 (3H, t, J=7.0 Hz), 1.2–1.6 (4H, m), 1.6–1.9 (2H, m), 3.99 (2H, t, J=6.5 Hz), 5.53 (2H, s), 6.92 (2H, d, J=8.8 Hz), 7.70 (2H, d, J=8.8 Hz)

APCI-MASS: m/z=264 (M+H)$^+$

Preparation 100
To a suspension of 2-amino-5-(4-n-pentyloxyphenyl)-1,3,4-thiadiazole (4.314 g) in ethanol (43 ml) was added ethyl 4-bromoacetylbenzoate (4.21 g) and refluxed for 4 hours. The reaction mixture was pulverized with ethyl acetate. The precipitate was filtered and dried. To a suspension of the powder in xylene (40 ml) was added trifluoroacetic acid (10 ml) and refluxed for 3 hours. The reaction mixture was pulverized with diisopropyl ether. The precipitate was filtered and dried to give 4-[2-(4-pentyloxyphenyl)imidazo[2,1-b][1,3,4]thiadiazol-6-yl]benzoic acid ethyl ester trifluoroacetic acid salt (5.3 g).

IR (KBr): 1710.6, 1610.3, 1272.8 cm$^{-1}$

APCI-MASS: m/z=436 (M+H)$^+$

Preparation 101
To a solution of 4-[2-(4-pentyloxyphenyl)imidazo-[2,1-b][1,3,4]thiadiazol-6-yl]benzoic acid ethyl ester trifluoroacetic acid salt (5.2 g) in the mixture of methanol (104 ml) and tetrahydrofuran (52 ml) was added 2N NaOH aq. (47 ml) and refluxed for 36 hours. The reaction mixture was adjusted to pH 1–2 with 1N HCl and the resulting precipitate was collected by filtration to give 4-[2-(4-pentyloxyphenyl)-imidazo[2,1-b][1,3,4]thiadiazol-6-yl]benzoic acid (4.27 g).

IR (KBr): 1681.6, 1606.4, 1255.4, 1174.4 cm$^{-1}$

APCI-MASS: m/z=408 (M+H)$^+$

Preparation 102
To a solution of 1-hydroxybenzotriazole (1.67 g) and 4-[2-(4-pentyloxyphenyl)imidazo[2,1-b][1,3,4]thiadiazol-6-yl]-benzoic acid (4.2 g) in dichloromethane (170 ml) was added 1-ethyl-3-(31-dimethylaminopropyl)carbodiimide hydrochloride (WSCD.HCl) (2.95 g) and stirred for 6 hours at ambient temperature. The reaction mixture was added to water. The organic layer was taken and dried over magnesium sulfate. Magnesium sulfate was filtered off, and the filtrate was evaporated under reduced pressure to give 1-[4-[2-(4-pentyloxyphenyl)imidazo[2,1-b][1,3,4]thiadiazol-6-yl]-benzoyloxy]benzotriazole (2.456 g).

IR (KBr): 1772.3, 1604.5, 1251.6, 983.5 cm$^{-1}$

NMR (CDCl$_3$, δ): 0.96 (3H, t, J=7.0 Hz), 1.2–1.6 (4H, m), 1.6–1.9 (2H, m), 4.05 (2H, t, J=6.5 Hz), 7.01 (2H, d, J=8.3

Hz), 7.4–7.6 (3H, m), 7.83 (2H, d, J=8.3 Hz), 8.07 (2H, d, J=8.0 Hz), 8.10 (1H, d, J=8.2 Hz), 8.21 (1H, s), 8.33 (2H, d, J=8.0 Hz)

APCI-MASS: m/z=525 (M+H)$^+$

The following compound was obtained according to a similar manner to that of Preparation 98.

Preparation 103

1-[4-(4-Ethoxyphenyl)benzoyl]-3-thiosemicarbazide

IR (KBr): 3295.7, 3263.0, 1668.1, 1257.4 cm$^{-1}$

NMR (DMSO-d$_6$, δ): 1.35 (3H, t, J=7.0 Hz), 4.08 (2H, q, J=7.0 Hz), 7.03 (2H, d, J=8.8 Hz), 7.68 (2H, d, J=8.8 Hz), 7.6–8.1 (6H, m), 9.35 (1H, s), 10.40 (1H, s)

APCI-MASS: m/z=316 (M+H)$^+$

The following compounds [Preparations 104 and 105] were obtained according to a similar manner to that of Preparation 99.

Preparation 104

2-Amino-5-[4-(4-ethoxyphenyl)phenyl]-1,3,4-thiadiazole

IR (KBr): 3432.7, 1602.6, 1500.3, 825.4 cm$^{-1}$

Preparation 105

2-Amino-5-(4-phenylphenyl)-1,3,4-thiadiazole

IR (KBr): 3278.4, 3085.5, 1643.1, 1513.8 cm$^{-1}$

APCI-MASS: m/z=254 (M+H)$^+$

The following compounds [Preparations 106 and 107] were obtained according to a similar manner to that of Preparation 100.

Preparation 106

4-[2-[4-(4-Ethoxyphenyl)phenyl]imidazo[2,1-b][1,3,4]-thiadiazol-6-yl]benzoic acid ethyl ester trifluoroacetic acid salt IR (KBr): 1708.6, 1604.5, 1274.7, 1105.0, 819.6, 729.0 cm$^{-1}$ APCI-MASS: m/z=470 (M+H)$^+$ Preparation 107

4-[2-(4-Phenylphenyl)imidazo[2,1-b][1,3,4]thiadiazol-6-yl]benzoic acid ethyl ester trifluoroacetic acid salt IR (KBr): 1710.6, 1606.4, 1278.6, 1106.9 cm$^{-1}$ APCI-MASS: m/z=426 (M+H)$^+$ The following compounds [Preparations 108 to 110] were obtained according to a similar manner to that of Preparation 101.

Preparation 108

4-[2-[4-(4-Ethoxyphenyl)phenyl]imidazo[2,1-b][1,3,4]-thiadiazol-6-yl]benzoic acid IR (KBr): 1683.6, 1604.5, 1278.6, 1253.5, 821.5, 727.0 cm$^{-1}$ Preparation 109

4-[2-(4-Phenylphenyl)imidazo[2,1-b][1,3,4]thiadiazol-6-yl]benzoic acid

IR (KBr): 1706.7, 1608.3, 1276.6, 1251.6 cm$^{-1}$

APCI-MASS: m/z=398 (M+H)$^+$

Preparation 110

4-[4-(4-n-Pentylcyclohexyl)piperazin-1-yl]benzoic acid monohydrochloride

IR (KBr): 2923.6, 2854.1, 1693.2, 1610.3 cm$^{-1}$

APCI-MASS: m/z=359 (M+H)$^+$

The following compounds [Preparations 111 and 112] were obtained according to a similar manner to that of Preparation 102.

Preparation 111

1-[4-[2-[4-(4-Ethoxyphenyl)phenyl]imidazo[2,1-b][1,3,4]-thiadiazol-6-yl]benzoyloxy]benzotriazole IR (KBr): 1778.0, 1714.4, 1602.6, 1276.6, 1255.4, 821.5, 779.1 cm$^{-1}$ APCI-MASS: m/z=559 (M+H)$^+$ Preparation 112

1-[4-[2-(4-Phenylphenyl)imidazo[2,1-b][1,3,4]thiadiazol-6-yl]benzoyloxy]benzotriazole IR (KBr): 1778.0, 1714.4, 1606.4, 1278.6, 1251.6, 821.5, 723.2 cm$^{-1}$ APCI-MASS: m/z=515 (M+H)$^+$ Preparation 113

To a solution of 4-phenylbenzoic acid (10.0 g), 1-hydroxybenzotriazole (7.5 g) and thiosemicarbazide (5.1 g) in dimethylformamide (50 ml) was added 1-ethyl-3-(3'-dimethylaminopropyl) carbodiimide hydrochloride (14.45 g) and stirred for 12 hours at ambient temperature. The reaction mixture was pulverized with water. The precipitate was collected by filtration and dried under reduced pressure to give 1-(4-phenylbenzoyl)-3-thiosemicarbazide (10.274 g).

IR (KBr): 3369.0, 3185.8, 1656.6, 1610.3, 1261.2, 744.4 cm$^{-1}$

APCI-MASS: m/z=272 (M+H)$^+$

The following compounds [Preparations 114 and 115] were obtained according to a similar manner to that of Preparation 77.

Preparation 114

1-[4-[4-(4-n-Pentylcyclohexyl)piperazin-1-yl]-benzoyloxy]benzotriazole

IR (KBr): 2919.7, 2848.3, 1778.0, 1600.6, 1232.3 cm$^{-1}$

NMR (CDCl$_3$, δ): 0.89 (3H, t, J=6.6 Hz), 0.8–1.1 (2H, m), 1.1–2.0 (15H, m), 2.6–2.8 (4H, m), 3.4–3.6 (4H, m), 6.93 (2H, d, J=9.2 Hz), 7.4–7.6 (3H, m), 8.0–8.2 (3H, m)

APCI-MASS: m/z=476 (M+H)$^+$

Preparation 115

1-[4-[2-[4-(4-Cyclohexylphenyl)piperazin-1-yl]ethyl]-benzoyloxy]benzotriazole

IR (KBr): 2923.6, 1799.3, 1781.9, 1608.3, 1232.3, 979.7 cm$^{-1}$

NMR (CDCl$_3$, δ): 1.1–1.6 (6H, m), 1.6–2.1 (4H, m), 2.43 (1H, m), 2.6–2.8 (6H, m), 2.9–3.1 (2H, m), 3.2–3.4 (4H, m), 6.88 (2H, d, J=8.6 Hz), 7.12 (2H, d, J=8.6 Hz), 7.46 (2H, d, J=8.3 Hz), 7.4–7.7 (3H, m), 8.11 (1H, dd, J=1.4 and 7.7 Hz), 8.21 (2H, d, J=8.3 Hz)

APCI-MASS: m/z=510 (M+H)$^+$

Preparation 116

To a suspension of 1-(4-cyclohexylphenyl)piperazine dihydrobromide (2.5 g) and potassium bicarbonate (2.125 g) in N,N-dimethylformamide (6 ml) was added methyl 4-(2-chloroethylphenyl) benzoate (1.22 g) and stirred for 24 hours at 120° C. The reaction mixture was added to a mixture of water and ethyl acetate. The organic layer was taken and dried over magnesium sulfate. The magnesium sulfate was filtered off, and the filtrate was evaporated under reduced pressure to give methyl 4-[2-[4-(4-cyclohexylphenyl)-piperazin-1-yl]ethyl]benzoate (1.247 g).

IR (KBr): 2927.4, 2852.2 1724.0, 1652.7, 1278.6 cm$^{-1}$

NMR (CDCl$_3$, δ): 1.2–1.5 (5H, m), 1.7–2.0 (5H, m), 2.42 (1H, m), 2.6–2.8 (6H, m), 2.8–3.0 (2H, m), 3.1–3.3 (4H, m), 3.91 (3H, s), 6.87 (2H, d, J=8.7 Hz), 7.11 (2H, d, J=8.7 Hz), 7.29 (2H, d, J=8.3 Hz), 7.96 (2H, d, J=8.3 Hz)

APCI-MASS: m/z=407 (M+H)$^+$

The following compound was obtained according to a similar manner to that of Preparation 43.

Preparation 117

4-[2-[4-(4-Cyclohexylphenyl)piperazin-1-yl]ethyl] benzoic acid

IR (KBr): 3673.7, 3648.7, 1710.6, 1515.8, 1243.9, 1228.4 cm$^{-1}$

APCI-MASS: m/z=393 (M+H)$^+$

Preparation 118

To a solution of 4-(4'-hydroxyphenyl)benzoic acid (15.00 g) in dimethylformamide (150 ml) were added successively n-propyl bromide (14.63 ml) and potassium carbonate (24.19 g). The mixture was stirred at 60° C. for 24 hours, during this period additional n-propyl bromide (1.27 ml) and potassium carbonate (1.94 g) were added into the mixture. After cooling to room temperature, the reaction mixture was poured into water (600 ml) and then the mixture was stirred for 30 minutes at room temperature. The resulting precipitate was filtered, washed with water, and dried to give the objective compound, propyl 4-(4'-propoxyphenyl)benzoate (20.48 g), as a white solid.

IR (KBr): 2966, 1711, 1605 cm$^{-1}$

NMR (CDCl$_3$, δ): 1.06 (6H, m), 1.83 (4H, m), 3.97 (2H, t, J=6.6 Hz), 4.30 (2H, t, J=6.6 Hz), 6.98 (2H, m), 7.59 (4H, m), 8.08 (2H, m)

APCI-MASS: m/z=299 (M+H)$^+$

Preparation 119

To a mixture of propyl 4-(4'-propoxyphenyl)benzoate (20.00 g) in a mixture of ethanol (100 ml) and tetrahydrofuran (40 ml) was added hydrazine monohydrate (32.5 ml). The mixture was refluxed for 2 hours, during this period additional hydrazine monohydrate (32.5 ml) was added into the mixture. After cooling to room temperature, the reaction mixture was poured into water (1800 ml) and then the mixture was stirred for 30 minutes at room temperature. The resulting precipitate was filtered, washed with water, and dried to give the objective compound, 4-(4'-propoxyphenyl)-benzoyl hydrazine (17.63 g), as a white solid.

IR (KBr): 3338, 3277, 3194, 2966, 2929, 1612 cm$^{-1}$

NMR (DMSO-d$_6$, δ): 0.99 (3H, t, J=7.4 Hz), 1.75 (2H, m), 3.98 (2H, t, J=6.5 Hz), 4.50 (2H, s), 7.03 (2H, d, J=8.8 Hz), 7.68 (4H, m), 7.89 (2H, d, J=8.4 Hz), 9.79 (1H, s)

APCI-MASS: m/z=271 (M+H)$^+$

The Starting Compound in the following Examples 1 to 30 and The Object Compounds (1) to (30) in the following Examples 1 to 30 are illustrated by chemical formulae as below.

The Starting Compound (the same in Examples 1 to 30)

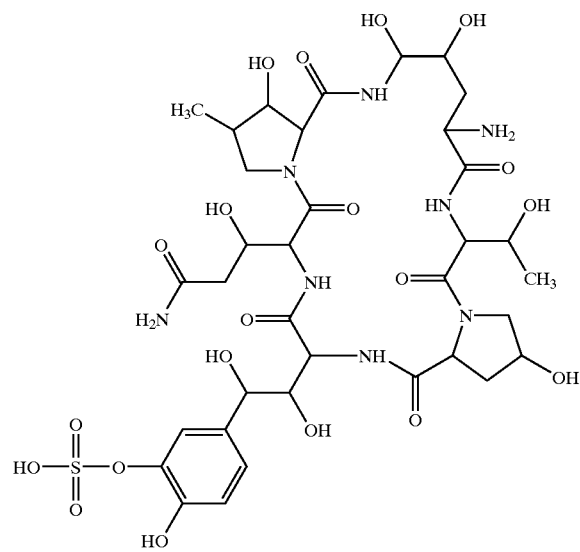

The object Compounds (1) to (30)

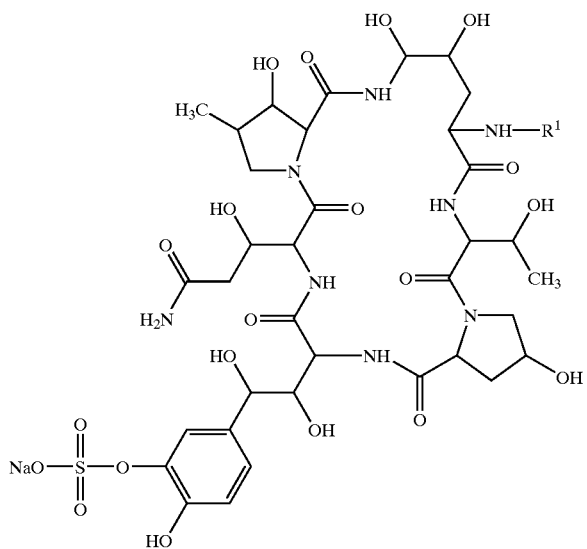

In the following Examples, The Object Compound (X) [e.g. The Object Compound (1)] means the object compound of Example (X) [e.g. Example (1)].

| Example No. | R$^1$ |
|---|---|
| 1 | —CO—C$_6$H$_4$—N(piperazine)N—C$_6$H$_4$—O—(CH$_2$)$_5$CH$_3$ |
| 2 | —CO—C$_6$H$_4$—N(piperazine)N—cyclohexyl-cyclohexyl |

-continued
| Example No. | R¹ |
|---|---|
| 3 | 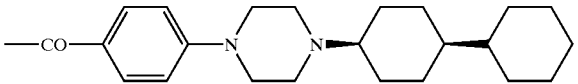 |
| 4 | 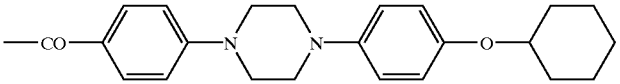 |
| 5 | 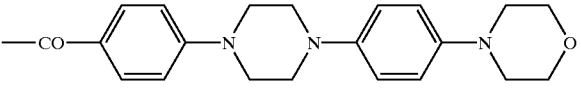 |
| 6 | 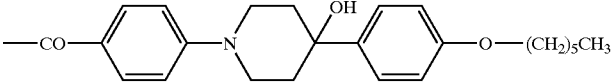 |
| 7 | 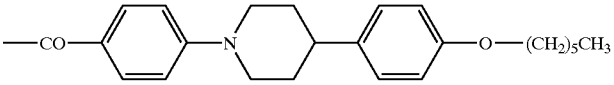 |
| 8 | 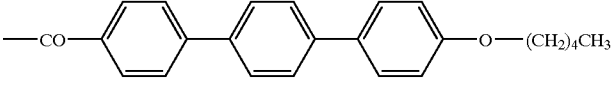 |
| 9 | 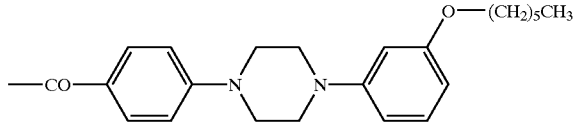 |
| 10 | 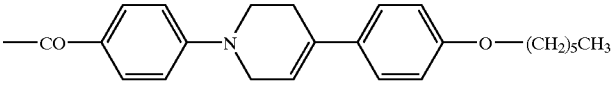 |
| 11 | 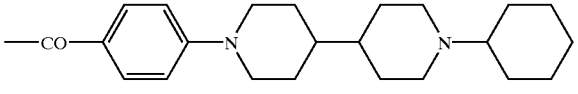 |
| 12 | 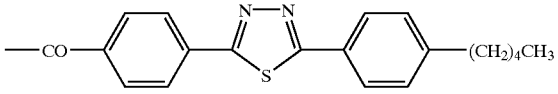 |
| 13 | 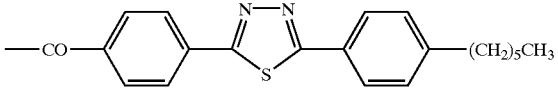 |
| 14 | 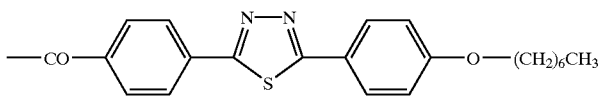 |
| 15 | 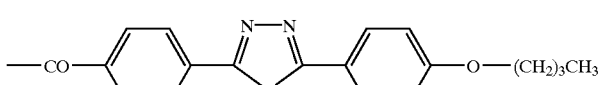 |
| 16 | 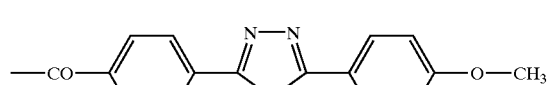 |

-continued
| Example No. | R¹ |
|---|---|
| 17 | 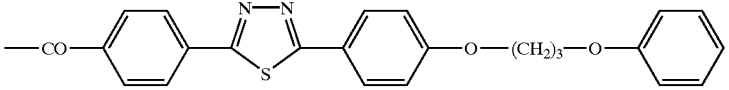 |
| 18 | 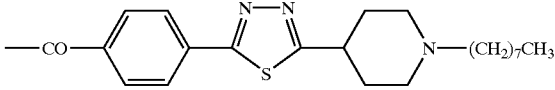 |
| 19 | 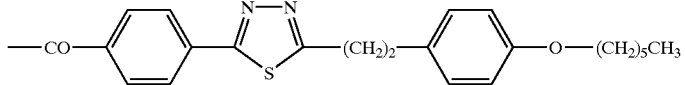 |
| 20 | 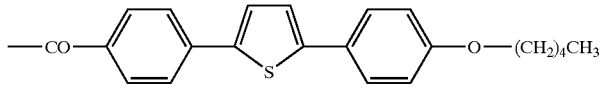 |
| 21 | 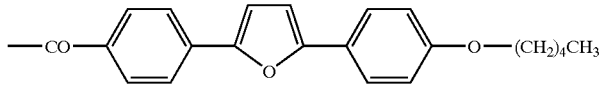 |
| 22 | 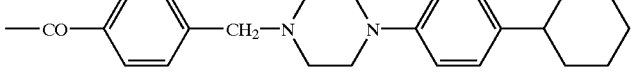 |
| 23 | 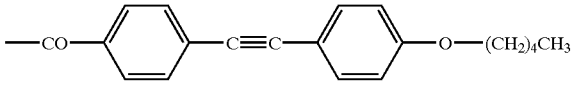 |
| 24 | 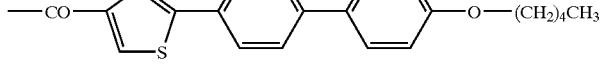 |
| 25 | 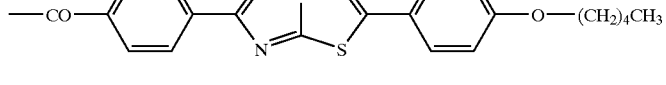 |
| 26 | 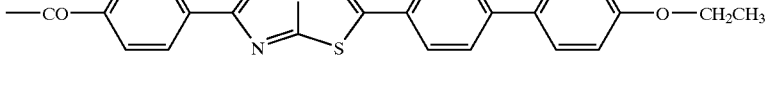 |
| 27 | 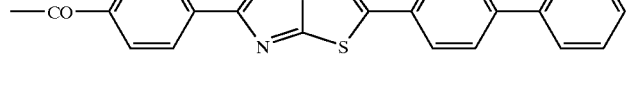 |
| 28 | 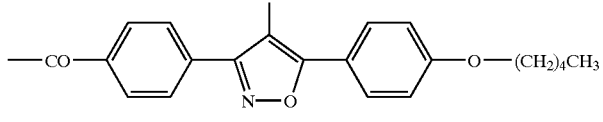 |
| 29 | 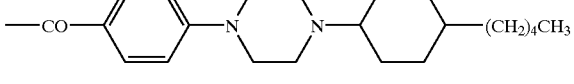 |
| 30 | 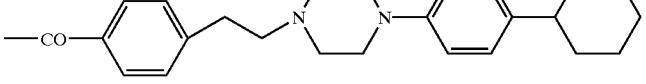 |

EXAMPLE 1

To a solution of The Starting Compound (33.55 g) and 1-[4-[4-(4-hexyloxyphenyl)piperazin-1-yl]benzoyloxy]-benzotriazole (17.48 g) in dimethylformamide (335.5 ml) was added diisopropylethylamine (7.32 ml) and stirred for 8 hours at ambient temperature. The reaction mixture was pulverized with ethyl acetate. The precipitate was collected by filtration and dried under reduced pressure. The powder was added to water and subjected to ion-exchange column chromatography on DOWEX-50WX4 (Trademark: prepared by Dow Chemical) and eluted with water. The fractions containing The Object Compound were combined and subjected to column chromatography on ODS (YMC-gel ODS-AM•S-50) (Trademark : prepared by Yamamura Chemical Lab.) and eluted with 25% acetonitrile aq. The fractions containing The Object Compound were combined and evaporated under reduced pressure to remove acetonitrile. The residue was lyophilized to give The Object Compound (1) (27.86 g).

The Object Compounds (2) to (21) were obtained according to a similar manner to that of Example 1.

EXAMPLE 2

IR (KBr): 3350, 1666.2, 1629.6, 1238.1 cm$^{-1}$

NMR (DMSO-d$_6$, δ): 0.96 (3H, d, J=6.7 Hz), 0.8–1.5 (15H, m), 1.5–2.1 (12H, m), 2.1–2.65 (4H, m), 3.0–3.2 (5H, m), 3.1–3.55 (4H, m), 3.65–4.5 (14H, m), 4.6–5.5 (11H, m), 6.72 (1H, d, J=8.2 Hz), 6.81 (1H, s), 6.83 (1H, d, J=8.2 Hz), 6.99 (2H, d, J=8.6 Hz), 7.04 (1H, s), 7.25–7.5 (3H, m), 7.81 (2H, d, J=8.6 Hz), 8.09 (1H, d, J=8.7 Hz), 8.28 (1H, d, J=8.7 Hz), 8.45 (1H, d, J=6.7 Hz), 8.83 (1H, s)

FAB-MASS: m/z=1231 (M–SO$_3$+Na)$^+$

EXAMPLE 3

IR (KBr): 3359.4, 1666.2, 1629.6, 1511.9 cm$^{-1}$

NMR (DMSO-d$_6$, δ): 0.96 (3H, d, J=6.7 Hz), 0.7–2.1 (27H, m), 2.1–2.7 (4H, m), 3.0–3.4 (9H, m), 3.6–4.5 (14H, m), 4.6–5.5 (11H, m), 6.72 (1H, d, J=8.2 Hz), 6.81 (1H, s), 6.83 (1H, d, J=8.2 Hz), 6.99 (2H, d, J=8.6 Hz), 7.04 (1H, s), 7.2–7.5 (3H, m), 7.81 (2H, d, J=8.6 Hz), 8.09 (1H, d, J=8.7 Hz), 8.28 (1H, d, J=8.7 Hz), 8.45 (1H, d, J=6.7 Hz), 8.83 (1H, s)

FAB-MASS: m/z=1231 (M–SO$_3$+Na)$^+$

EXAMPLE 4

IR (KBr): 3353.6, 1668.1, 1629.6, 1508.1, 1234.2 cm$^{-1}$

NMR (DMSO-d$_6$, δ): 0.96 (3H, d, J=7.0 Hz), 1.05 (3H, d, J=6.0 Hz), 0.8–2.6 (17H, m), 3.0–4.5 (23H, m), 4.5–5.3 (10H, m), 5.45 (1H, d, J=4.8 Hz), 6.6–7.2 (10H, m), 7.2–7.5 (3H, m), 8.06 (2H, d, J=8.9 Hz), 8.25 (1H, d, J=8.0 Hz), 8.40 (1H, d, J=8 Hz), 8.61 (1H, d, J=6.7 Hz), 8.82 (1H, s)

FAB-MASS: m/z=1343 (M+Na)$^+$

Analysis Calcd. for C$_{58}$H$_{77}$N$_{10}$O$_{22}$SNa.8H$_2$O: C, 47.54; H, 6.40; N, 9.56. Found: C, 47.65; H, 6.36; N, 9.42.

EXAMPLE 5

IR (KBr): 3355.5, 1668.1, 1629.6, 1511.9, 1234.2 cm$^{-1}$

NMR (DMSO-d$_6$, δ): 0.96 (3H, d, J=6.8 Hz), 1.07 (3H, d, J=5.7 Hz), 1.7–2.1 (3H, m), 2.1–2.7 (4H, m), 2.99 (4H, t, J=4.7 Hz), 3.1–3.3 (5H, m), 3.35–3.5 (4H, m), 3.6–3.8 (2H, m), 3.72 (4H, t, J=4.7 Hz), 3.8–4.5 (12H, m), 4.65–5.05 (7H, m), 5.07 (1H, d, J=5.6 Hz), 5.13 (1H, d, J=3.2 Hz), 5.21 (1H, d, J=4.6 Hz), 5.45 (1H, d, J=6.0 Hz), 6.73 (1H, d, J=8.2 Hz), 6.81 (1H, s), 6.83 (1H, dd, J=1.9 and 8.2 Hz), 6.87 (2H, d, J=9.4 Hz), 6.93 (2H, d, J=9.4 Hz), 7.00 (2H, d, J=9.0 Hz), 7.04 (1H, d, J=1.9 Hz), 7.2–7.5 (3H, m), 7.81 (2H, d, J=9.0 Hz), 8.04 (1H, d, J=9.0 Hz), 8.21 (1H, d, J=8.4 Hz), 8.39 (1H, d, J=7.1 Hz), 8.83 (1H, s)

FAB-MASS: m/z=1330 (M+Na)$^+$

Analysis Calcd. for C$_{56}$H$_{74}$N$_{11}$O$_{22}$SNa.6H$_2$O: C, 47.49; H, 6.12; N, 10.88. Found: C, 47.26; H, 6.07; N, 10.73.

EXAMPLE 6

IR (KBr): 3349, 1668.1, 1627.6, 1247.7 cm$^{-1}$

NMR (DMSO-d$_6$, δ): 0.87 (3H, t, J=6.6 Hz), 0.96 (3H, d, J=6.8 Hz), 1.06 (3H, d, J=5.8 Hz), 1.2–1.5 (6H, m), 1.6–2.7 (13H, m), 3.1–3.4 (3H, m), 3.6–4.5 (18H, m), 3.7–5.1 (8H, m), 5.11 (1H, d, J=5.6 Hz), 5.14 (1H, d, J=3.1 Hz), 5.22 (1H, d, J=4.6 Hz), 5.45 (1H, d, J=6.0 Hz), 6.73 (1H, d, J=8.3 Hz), 6.81 (1H, s), 6.83 (1H, d, J=8.3 Hz), 6.85 (2H, d, J=8.8 Hz), 6.98 (2H, d, J=8.9 Hz), 7.04 (1H, s), 7.2–7.5 (5H, m), 7.78 (2H, d, J=8.8 Hz), 8.06 (1H, d, J=9.3 Hz), 8.24 (1H, d, J=8.1 Hz), 8.37 (1H, d, J=7.5 Hz), 8.83 (1H, s)

FAB-MASS: m/z=1360 (M+Na)$^+$

Analysis Calcd. for C$_{59}$H$_{80}$N$_9$O$_{23}$SNa.6H$_2$O: C, 48.99; H, 6.41; N, 8.71. Found: C, 48.78; H, 6.28; N, 8.59.

EXAMPLE 7

IR (KBr): 3384.5, 1666.2, 1627.6, 1510.0, 1047.2 cm$^{1}$

NMR (DMSO-d$_6$, δ): 0.88 (3H, t, J=6.6 Hz), 0.96 (3H, d, J=6.8 Hz), 1.31 (3H, d, J=6.4 Hz), 1.2–1.5 (6H, m), 1.5–2.1 (9H, m), 2.1–2.45 (3H, m), 2.5–3.0 (4H, m), 3.1–3.35 (1H, m), 3.6–4.5 (18H, m), 4.7–5.3 (7H, m), 5.08 (1H, d, J=5.6 Hz), 5.14 (1H, d, J=3.2 Hz), 5.22 (1H, d, J=4.5 Hz), 5.45 (1H, d, J=6.0 Hz), 6.73 (1H, d, J=8.2 Hz), 6.8–6.9 (4H, m), 6.97 (2H, d, J=9.0 Hz), 7.04 (1H, s), 7.15 (2H, d, J=8.7 Hz), 7.2–7.5 (3H, m), 7.79 (2H, d, J=8.7 Hz), 8.04 (1H, d, J=9.0 Hz), 8.22 (1H, d, J=8.4 Hz), 8.36 (1H, d, J=7.1 Hz), 8.84 (1H, s)

FAB-MASS: m/z=1353 (M+Na)$^+$

Analysis Calcd. for C$_{59}$H$_{80}$N$_9$O$_{22}$SNa.5H$_2$O: C, 50.17; H, 6.42; N, 8.92. Found: C, 50.09; H, 6.36; N 8.88.

EXAMPLE 8

IR (KBr): 3334.3, 1668.1, 1631.5, 1521.6, 1247.7 cm$^{-1}$

NMR (DMSO-d$_6$, δ): 0.91 (3H, t, J=7.2 Hz), 0.96 (3H, d, J=7.3 Hz), 1.09 (3H, d, J=5.8 Hz), 1.2–1.5 (4H, m), 1.65–2.1 (5H, m), 2.1–2.7 (4H, m), 3.1–3.3 (1H, m), 3.6–4.6 (16H, m), 4.7–5.3 (7H, m), 5.11 (1H, d, J=5.5 Hz), 5.17 (1H, d, J=3.1 Hz), 5.26 (1H, d, J=4.5 Hz), 5.54 (1H, d, J=5.9 Hz), 6.73 (1H, d, J=8.2 Hz), 6.82 (1H, d, J=8.2 Hz), 6.85 (1H, s), 7.04 (2H, d, J=8.5 Hz), 7.06 (1H, s), 7.2–7.5 (3H, m), 7.6–7.9 (8H, m), 8.01 (2H, d, J=8.4 Hz), 8.1 (1H, d, J=9.0 Hz), 8.3 (1H, d, J=8.4 Hz), 8.8 (1H, d, J=7.1 Hz), 8.85 (1H, s)

FAB-MASS: m/z=1323 (M+Na)$^+$

Analysis Calcd. for C$_{59}$H$_{73}$N$_8$O$_{22}$SNa.5H$_2$O: C, 50.93; H, 6.01; N 8.05. Found: C, 51.14; H, 6.13; N, 8.03.

EXAMPLE 9

IR (KBr): 3349.7, 1668.1, 1629.6, 1236.1 cm$^{1}$

NMR (DMSO-d$_6$, δ): 0.91 (3H, t, J=6.3 Hz), 0.96 (3H, d, J=6.8 Hz), 1.06 (3H, d, J=5.8 Hz), 1.2–1.5 (6H, m), 1.5–2.1 (5H, m), 2.1–2.7 (4H, m), 3.1–3.5 (9H, m), 3.6–4.5 (16H, m), 4.7–5.3 (7H, m), 5.07 (1H, d, J=5.6 Hz), 5.14 (1H, d, J=3.2 Hz), 5.22 (1H, d, J=4.5 Hz), 5.45 (1H, d, J=5.9 Hz), 6.38 (1H, d, J=8.0 Hz), 6.49 (1H, s), 6.56 (1H, d, J=8.0 Hz), 6.72 (1H, d, J=8.2 Hz), 6.80 (1H, s), 6.82 (1H, d, J=8.2 Hz), 7.00 (2H, d, J=9.0 Hz), 7.04 (1H, s), 7.12 (1H, dd, J=8.0 Hz), 7.2–7.5 (3H, m), 7.81 (2H, d, J=9.0 Hz), 8.08 (1H, d, J=9.0 Hz), 8.25 (1H, d, J=8.4 Hz), 8.39 (1H, d, J=7.1 Hz), 8.83 (1H, s)

FAB-MASS: m/z=1345 (M+Na)$^+$

Analysis Calcd. for $C_{58}H_{79}N_{10}O_{22}SNa \cdot 5H_2O$: C, 49.29; H, 6.35; N, 9.91. Found: C, 49.12; H, 6.11; N, 9.81.

EXAMPLE 10

IR (KBr): 3332.4, 1664.3, 1627.6, 1510.0, 1234.2 cm$^{-1}$

NMR (DMSO-d$_6$, δ): 0.91 (3H, t, J=6.6 Hz), 0.96 (3H, d, J=6.7 Hz), 1.07 (3H, d, J=5.9 Hz), 1.2–1.5 (6H, m), 1.6–2.1 (5H, m), 2.1–2.7 (6H, m), 3.1–3.3 (1H, m), 3.5–4.5 (20H, m), 4.65–5.2 (9H, m), 5.22 (1H, d, J=4.4 Hz), 5.46 (1H, d, J=6 Hz), 6.18 (1H, m), 6.73 (1H, d, J=8.2 Hz), 6.81 (1H, s), 6.83 (1H, d, J=8.2 Hz), 6.90 (2H, d, J=8.9 Hz), 6.97 (2H, d, J=9.1 Hz), 7.04 (1H, s), 7.2–7.5 (3H, m), 7.40 (2H, d, J=8.9 Hz), 7.81 (2H, d, J=9.1 Hz), 8.03 (1H, d, J=9.0 Hz), 8.21 (1H, d, J=8.4 Hz), 8.36 (1H, d, J=7.1 Hz), 8.83 (1H, s)

FAB-MASS: m/z=1342 (M+Na)$^+$

Analysis Calcd. for $C_{59}H_{78}N_9O_{22}SNa \cdot 7H_2O$: C, 48.99; H, 6.41; N, 8.71. Found: C, 48.65; H, 6.03; N, 8.64.

EXAMPLE 11

IR (KBr): 3380, 1664.3, 1631.5, 1243.9 cm$^1$

NMR (DMSO-d$_6$, δ): 0.92 (3H, d, J=8.3 Hz), 1.06 (3H, d, J=5.7 Hz), 1.0–2.1 (32H, m), 2.1–3.0 (8H, m), 3.1–3.3 (1H, m), 3.6–4.5 (16H, m), 4.65–5.2 (7H, m), 5.07 (1H, d, J=5.6 Hz), 5.14 (1H, d, J=3.1 Hz), 5.22 (1H, d, J=4.5 Hz), 5.43 (1H, d, J=6.0 Hz), 6.72 (1H, d, J=8.2 Hz), 6.81 (1H, s), 6.83 (1H, d, J=8.2 Hz), 6.92 (2H, d, J=8.8 Hz), 7.04 (1H, s), 7.25–7.5 (3H, m), 7.76 (2H, d, J=8.8 Hz), 8.06 (1H, d, J=8.2 Hz), 8.25 (1H, d, J=8.6 Hz), 8.35 (1H, d, J=8.2 Hz), 8.83 (1H, s)

FAB-MASS: m/z=1311 (M+Na)$^+$

Analysis Calcd. for $C_{58}H_{84}N_{10}O_{21}S \cdot 8H_2O$: C, 48.60; H, 7.03; N, 9.77. Found: C, 48.58; H, 6.57; N, 9.69.

EXAMPLE 12

IR (KBr): 3357, 2933, 1631, 1535, 1515, 1442, 1280, 1047 cm$^{-1}$

NMR (DMSO-d$_6$, δ): 0.88 (3H, t, J=6.7 Hz), 0.97 (3H, d, J=6.8 Hz), 1.10 (3H, d, J=5.9 Hz), 1.2–1.4 (4H, m), 1.5–1.7 (2H, m), 1.7–2.1 (3H, m), 2.1–2.4 (3H, m), 3.5–3.6 (1H, m), 2.67 (2H, t, J=7.7 Hz), 3.1–3.3 (1H, m), 3.7–4.6 (14H, m), 4.8–5.1 (7H, m), 5.09 (1H, d, J=5.4 Hz), 5.16 (1H, d, J=3.1 Hz), 5.24 (1H, d, J=4.6 Hz), 5.53 (1H, d, J=5.9 Hz), 6.73 (1H, d, J=8.2 Hz), 6.8–7.0 (2H, m), 7.04 (1H, s), 7.22 (1H, br s), 7.3–7.5 (4H, m), 7.95 (2H, d, J=8.2 Hz), 8.0–8.2 (5H, m), 8.21 (1H, d, J=7.7 Hz), 8.83 (1H, s), 8.90 (1H, d, J=7.0 Hz)

FAB-MASS: m/z=1315.1 (M+Na)$^+$

Analysis Calcd. for $C_{55}H_{69}N_{10}O_{21}NaS \cdot 6H_2O$: C, 47.14; H, 5.83; N, 9.99. Found: C, 47.39; H, 5.69; N, 10.05.

EXAMPLE 13

IR (KBr): 3438, 3357, 2931, 1631, 1537, 1515, 1442, 1280, 1047 cm$^{-1}$

NMR (DMSO-d$_6$, δ): 0.87 (3H, t, J=6.7 Hz), 0.97 (3H, d, J=6.8 Hz), 1.09 (3H, d, J=6.0 Hz), 1.2–1.4 (6H, m), 1.5–1.7 (2H, m), 1.8–2.1 (2H, m), 2.2–2.4 (3H, m), 2.5–2.6 (1H, m), 2.67 (2H, t, J=7.7 Hz), 3.1–3.3 (1H, m), 3.4–4.5 (14H, m), 4.7–5.1 (7H, m), 5.08 (1H, d, J=5.5 Hz), 5.17 (1H, d, J=3.2 Hz), 5.23 (1H, d, J=4.6 Hz), 5.53 (1H, d, J=5.8 Hz), 6.73 (1H, d, J=8.2 Hz), 6.8–7.0 (2H, m), 7.04 (1H, s), 7.2–7.5 (5H, m), 7.95 (2H, d, J=8.2 Hz), 8.0–8.3 (6H, m), 8.84 (1H, s), 8.89 (1H, d, J=7.0 Hz)

APCI-MASS: m/z=1328.9 (M+Na)$^+$

Analysis Calcd. for $C_{56}H_{71}N_{10}O_{21}S_2Na \cdot 7H_2O$: C, 46.92; H, 5.98; N, 9.77. Found: C, 47.07; H, 5.52; N, 9.76

EXAMPLE 14

IR (KBr): 3386, 2935, 2858, 1666, 1631, 1515, 1442, 1257, 1047 cm$^{-1}$

NMR (DMSO-d$_6$, δ): 0.88 (3H, t, J=6.7 Hz), 0.97 (3H, d, J=6.7 Hz), 1.09 (3H, d, J=5.9 Hz), 1.2–1.5 (8H, m), 1.7–2.1 (5H, m), 2.2–2.5 (3H, m), 2.5–2.6 (1H, m), 3.1–3.3 (1H, m), 3.7–4.5 (16H, m), 4.7–5.1 (7H, m), 5.11 (1H, d, J=5.5 Hz), 5.18 (1H, d, J=3.1 Hz), 5.26 (1H, d, J=4.6 Hz), 5.54 (1H, d, J=5.8 Hz), 6.73 (1H, d, J=8.2 Hz), 6.8–7.0 (2H, m), 7.05 (1H, s), 7.13 (2H, d, J=8.8 Hz), 7.2–7.5 (3H, m), 7.97 (2H, d, J=8.8 Hz), 8.0–8.2 (5H, m), 8.24 (1H, d, J=7.7 Hz), 8.85 (1H, s), 8.92 (1H, d, J=7.0 Hz)

FAB-MASS: m/z=1359 (M+Na)$^+$

Analysis Calcd. for $C_{57}H_{73}N_{10}O_{22}S_2Na \cdot 7H_2O$: C, 46.78; H, 5.99; N, 9.57. Found C, 46.90; H, 6.24; N, 9.56.

EXAMPLE 15

IR (KBr): 3350, 2956, 1633, 1517, 1444, 1255, 1047 cm$^{-1}$

NMR (DMSO-d$_6$, δ): 0.9–1.1 (6H, m), 1.09 (3H, d, J=5.5 Hz), 1.4–1.6 (2H, m), 1.7–2.0 (5H, m), 2.1–2.5 (3H, m), 2.5–2.6 (1H, m), 3.1–3.3 (1H, m), 3.7–4.5 (16H, m), 4.7–5.1 (7H, m), 5.12 (1H, d, J=5.5 Hz), 5.19 (1H, d, J=2.9 Hz), 5.27 (1H, d, J=4.4 Hz), 5.57 (1H, d, J=5.7 Hz), 6.74 (1H, d, J=8.2 Hz), 6.8–6.9 (2H, m), 7.06 (1H, s), 7.14 (2H, d, J=8.9 Hz), 7.2–7.5 (3H, m), 7.97 (2H, d, J=8.9 Hz), 8.0–8.2 (5H, m), 8.26 (1H, d, J=7.7 Hz), 8.86 (1H, s), 8.94 (1H, d, J=7.0 Hz)

FAB-MASS: 1317 (M+Na)$^+$

Analysis Calcd. for $C_{54}H_{67}N_{10}O_{22}S_2Na \cdot 7H_2O$: C, 45.63; H, 5.74; N, 9.85. Found: C, 45.80; H, 6.05; N, 9.83.

EXAMPLE 16

IR (KBr): 3365, 3342, 1639, 1519, 1442, 1278, 1256, 1047 cm$^{-1}$

NMR (DMSO-d$_6$, δ): (3H, d, J=6.8 Hz), 1.10 (3H, d, J=6.0 Hz), 1.7–2.0 (3H, m), 2.1–2.4 (3H, m), 2.5–2.6 (1H, m), 3.1–3.2 (1H, m), 3.7–3.8 (2H, m), 3.86 (3H, s), 3.9–4.6 (12H, m), 4.7–5.1 (7H, m), 5.09 (1H, d, J=5.6 Hz), 5.16 (1H, d, J=3.1 Hz), 5.25 (1H, d, J=4.5 Hz), 5.49 (1H, d, J=5.9 Hz), 6.73 (1H, d, J=8.2 Hz), 6.8–6.9 (2H, m), 7.06 (1H, s), 7.15 (2H, d, J=8.9 Hz), 7.2–7.5 (3H, m), 7.99 (2H, d, J=8.9 Hz), 8.1–8.4 (6H, m), 8.83 (1H, s), 8.94 (1H, d, J=7.0 Hz)

FAB-MASS: m/z=1275.4 (M+Na)$^+$

Analysis Calcd. for $C_{51}H_{61}N_{10}O_{22}S_2Na \cdot 7H_2O$: C, 44.41; H, 5.48; N, 10.15. Found: C, 44.52; H, 5.35; N, 10.10.

EXAMPLE 17

IR (KBr): 3350, 1660, 1633, 1515, 1444, 1243, 1047 cm$^{-1}$

NMR (DMSO-d$_6$, δ): 0.97 (3H, d, J=6.8 Hz), 1.10 (3H, d, J=5.9 Hz), 1.8–2.1 (3H, m), 2.2–2.5 (5H, m), 2.5–2.6 (1H, m), 3.1–3.3 (1H, m), 3.7–4.6 (18H, m), 4.8–5.1 (7H, m), 5.09 (1H, d, J=5.6 Hz), 5.16 (1H, d, J=3.2 Hz), 5.24 (1H, d, J=4.5 Hz), 5.54 (1H, d, J=5.9 Hz), 6.73 (1H, d, J=8.2 Hz), 6.8–7.5 (13H, m), 7.98 (2H, d, J=8.8 Hz), 8.0–8.2 (5H, m), 8.23 (1H, d, J=7.7 Hz), 8.84 (1H, s), 8.91 (1H, d, J=7.1 Hz)

FAB-MASS: m/z=1395 (M+Na)$^+$

Analysis Calcd. for $C_{59}H_{69}N_{10}O_{23}NaS_2 \cdot 5H_2O$: C, 48.42; H, 5.44; N, 9.57. Found: C, 48.28; H, 5.42; N, 9.52.

EXAMPLE 18

IR (KBr): 3350, 1668, 1631, 1537, 1513, 1442, 1278, 1245, 1043 cm$^{-1}$

NMR (DMSO-d$_6$, δ): 0.87 (3H, t, J=6.8 Hz), 0.96 (3H, d, J=6.8 Hz), 1.08 (3H, d, J=5.9 Hz), 1.2–1.4 (10H, m), 1.4–1.6 (2H, m), 1.7–2.0 (5H, m), 2.1–2.6 (8H, m), 3.0–3.3 (5H, m), 3.7–4.5 (16H, m), 4.7–5.1 (7H, m), 5.08 (1H, d, J=5.6 Hz), 5.14 (1H, d, J=3.2 Hz), 5.22 (1H, d, J=4.6 Hz), 5.51 (1H, d, J=6.0 Hz), 6.73 (1H, d, J=8.2 Hz), 6.8–7.0 (2H, m), 7.0–7.4 (4H, m), 8.0–8.2 (5H, m), 8.20 (1H, d, J=7.7 Hz), 8.83 (1H, s), 8.92 (1H, d, J=7.0 Hz)

FAB-MASS: m/z=1364.2 (M+2Na)$^+$

Analysis Calcd. for $C_{57}H_{81}N_{11}O_{21}S_2 \cdot 6H_2O$: C, 47.92; H, 6.56; N, 10.79. Found: C, 48.19; H, 6.38; N, 10.65.

EXAMPLE 19

IR (KBr): 3325, 1675, 1648, 1540, 1513 cm$^{-1}$

NMR (DMSO-d$_6$, δ): 0.87 (3H, t, J=7.2 Hz), 0.96 (3H, d, J=6.7 Hz), 1.08 (3H, d, J=5.7 Hz), 1.2–1.5 (6H, m), 1.6–2.0 (5H, m), 2.1–2.4 (3H, m), 2.5–2.6 (1H, m), 3.03 (2H, t, J=7.9 Hz), 3.2–3.3 (1H, m), 3.4–3.5 (1H, m), 3.6–3.8 (2H, m), 3.8–4.5 (14H, m), 4.7–5.2 (7H, m), 5.09 (1H, d, J=5.6 Hz), 5.16 (1H, d, J=3.1 Hz), 5.25 (1H, d, J=4.5 Hz), 5.49 (1H, d, J=5.9 Hz), 6.73 (1H, d, J=8.2 Hz), 6.8–7.0 (4H, m), 7.05 (1H, s), 7.2–7.5 (5H, m), 8.0–8.2 (5H, m), 8.22 (1H, d, J=7.7 Hz), 8.84 (1H, s), 8.91 (1H, d, J=7.0 Hz)

APCI-MASS: m/z=1373.5 (M+Na)$^+$

Analysis Calcd. for $C_{58}H_{75}N_{10}O_{22}S_2Na \cdot 6H_2O$: C, 47.73; H, 6.01; N, 9.60. Found: C, 47.89; H, 6.21; N, 9.47.

EXAMPLE 20

IR (KBr): 3334, 2944, 1668, 1631, 1533, 1452, 1278, 1249, 1079 cm$^{-1}$

NMR (DMSO-d$_6$, δ): 0.90 (3H, t, J=7.0 Hz), 0.96 (3H, d, J=6.7 Hz), 1.08 (3H, d, J=5.7 Hz), 1.3–1.5 (4H, m), 1.7–2.1 (5H, m), 2.1–2.4 (3H, m), 2.6–2.7 (1H, m), 3.1–3.3 (1H, m), 3.6–4.5 (16H, m), 4.7–5.1 (7H, m), 5.11 (1H, d, J=5.5 Hz), 5.18 (1H, d, J=3.0 Hz), 5.26 (1H, d, J=4.4 Hz), 5.54 (1H, d, J=5.8 Hz), 6.73 (1H, d, J=8.2 Hz), 6.8–7.1 (5H, m), 7.2–7.4 (3H, m), 7.45 (1H, d, J=3.8 Hz), 7.6–7.8 (3H, m), 7.76 (2H, d, J=8.3 Hz), 7.95 (2H, d, J=8.3 Hz), 8.10 (1H, d, J=8.2 Hz), 8.26 (1H, d, J=7.7 Hz), 8.75 (1H, d, J=7.0 Hz), 8.85 (1H, s)

FAB-MASS: m/z=1329.3 (M+Na)$^+$

Analysis Calcd. for $C_{57}H_{71}N_8O_{22}S_2Na \cdot 6.5H_2O$: C, 48.06; H, 5.94; N, 7.87. Found: C, 48.14; H, 6.21; N, 7.82.

EXAMPLE 21

IR (KBr): 3376, 2925, 1668, 1631, 1504, 1247 cm$^{-1}$

NMR (DMSO-d$_6$, δ): 0.90 (3H, t, J=7.2 Hz), 0.96 (3H, d, J=6.7 Hz), 1.08 (3H, d, J=5.4 Hz), 1.3–1.5 (4H, m), 1.6–2.1 (5H, m), 2.2–2.6 (4H, m), 3.1–3.3 (1H, m), 3.6–4.6 (16H, m), 4.7–5.2 (7H, m), 5.11 (1H, d, J=5.5 Hz), 5.16 (1H, d, J=3.1 Hz), 5.26 (1H, d, J=4.4 Hz), 5.54 (1H, d, J=5.9 Hz), 6.73 (1H, d, J=8.2 Hz), 6.8–7.5 (10H, m), 7.77 (2H, d, J=8.7 Hz), 7.86 (2H, d, J=8.4 Hz), 7.97 (2H, d, J=8.4 Hz), 8.08 (1H, d, J=8.2 Hz), 8.25 (1H, d, J=7.7 Hz), 8.75 (1H, d, J=7.0 Hz), 8.85 (1H, s)

FAB-MASS: m/z=1313.9 (M+Na)$^+$

Analysis Calcd. for $C_{57}H_{71}N_8O_{23}SNa \cdot 7H_2O$: C, 48.30; H, 6.04; N, 7.91. Found: C, 48.56; H, 6.30; N, 7.90.

EXAMPLE 22

To a solution of 1-hydroxybenzotriazole (45.5 mg) and 4-[4-(4-cyclohexylphenyl)piperazin-1-yl]methylbenzoic acid hydrochloride (106 mg) in the mixture of triethylamine (78.1 μl) and dimethylformamide (2.6 ml) was added 1-ethyl-3-(3'-dimethylaminopropyl)carbodiimide hydrochloride (80.3 mg) and stirred for 2 hours at ambient temperature. Then to the reaction mixture was added The Starting Compound (262.4 mg) and 4-dimethylaminopyridine (37.7 mg) and stirred for 4 hours at ambient temperature. The reaction mixture was pulverized with ethyl acetate. The precipitate was collected by filtration and dried over reduced pressure. The powder was added to water and subjected to ion-exchange column chromatography on DOWEX-50WX4 and eluted with water. The fractions containing The Object Compound were combined and subjected to column chromatography on ODS (YMC-gel ODS-AM S-50) and eluted with 30–50% acetonitrile aq. The fractions containing The Object Compound were combined and evaporated under reduced pressure to remove acetonitrile. The residue was lyophilized to give The Object Compound (22) (55 mg).

IR (KBr): 3363.2, 1666.2, 1631.5, 1274.7 cm$^{-1}$

NMR (DMSO-d$_6$, δ): 0.96 (3H, d, J=6.6 Hz), 1.07 (3H, d, J=5.8 Hz), 0.9–2.1 (13H, m), 2.1–2.7 (5H, m), 3.1–3.6 (9H, m), 3.6–4.6 (16H, m), 4.7–5.6 (11H, m), 6.73 (1H, d, J=8.2 Hz), 6.8–6.95 (4H, m), 7.06 (1H, s), 7.09 (2H, d, J=8.4 Hz), 7.2–7.5 (3H, m), 7.6 (2H, d, J=7.3 Hz), 8.1 (1H, d, J=8.7 Hz), 8.3 (1H, d, J=8.7 Hz), 8.78 (1H, d, J=6.7 Hz), 8.84 (1H, s)

FAB-MASS: m/z=1240 (M−SO$_3$+Na)$^+$

The Object Compounds (23) to (30) were obtained according to a similar manner to that of Example 22.

EXAMPLE 23

IR (KBr): 3350, 2929, 1673, 1646, 1631, 1538, 1513, 1456, 1247, 1047 cm$^{-1}$

NMR (DMSO-d$_6$, δ): 0.90 (3H, t, J=7.2 Hz), 0.96 (3H, d, J=6.9 Hz), 1.08 (3H, d, J=5.7 Hz), 1.2–1.5 (4H, m), 1.7–2.0 (5H, m), 2.1–2.5 (3H, m), 2.6–2.7 (1H, m), 3.7–4.6 (16H, m), 4.8–5.1 (7H, m), 5.09 (1H, d, J=5.5 Hz), 5.16 (1H, d, J=3.1 Hz), 5.24 (1H, d, J=4.5 Hz), 5.52 (1H, d, J=5.7 Hz), 6.73 (1H, d, J=8.3 Hz), 6.8–7.0 (2H, m), 7.0–7.1 (3H, m), 7.2–7.5 (3H, m), 7.51 (2H, d, J=8.6 Hz), 7.60 (2H, d, J=8.2 Hz), 7.93 (2H, d, J=8.2 Hz), 8.10 (1H, d, J=8.4 Hz), 8.24 (1H, d, J=7.7 Hz), 8.81 (1H, d, J=7.0 Hz), 8.84 (1H, s)

FAB-MASS: m/z=1271 (M+Na)$^+$

Analysis Calcd. for $C_{55}H_{69}N_8O_{22}SNa \cdot 6H_2O$: C, 48.67; H, 6.02; N, 8.26. Found: C, 48.82; H, 6.18; N, 8.20.

EXAMPLE 24

IR (KBr): 3365, 2935, 2873, 1656, 1631, 1535, 1457, 1247, 1047 cm$^{-1}$

NMR (DMSO-d$_6$, δ): 0.87 (3H, t, J=7.2 Hz), 0.96 (3H, d, J=6.7 Hz), 1.12 (3H, d, J=5.7 Hz), 1.3–1.5 (4H, m), 25 1.6–2.1 (5H, m), 2.2–2.5 (4H, m), 3.1–3.3 (1H, m), 3.6–3.8 (2H, m), 4.0–4.6 (14H, m), 4.8–5.0 (3H, m), 5.0–5.2 (6H, m), 5.24 (1H, d, J=4.5 Hz), 5.56 (1H, d, J=5.7 Hz), 6.73 (1H, d, J=8.2 Hz), 6.8–6.9 (2H, m), 7.0–7.5 (6H, m), 7.70 (2H, d, J=8.8 Hz), 7.79 (2H, d, J=8.5 Hz), 8.0–8.1 (2H, m), 8.13 (2H, d, J=8.5 Hz), 8.30 (1H, s), 8.62 (1H, d, J=7.0 Hz), 8.83 (1H, s)

FAB-MASS: m/z=1330 (M+Na)$^+$

Analysis Calcd. for $C_{56}H_{70}N_9O_{22}S_2Na \cdot 6H_2O$: C, 47.49; H, 5.84; N, 8.90. Found: C, 47.87; H, 5.49; N, 8.88.

EXAMPLE 25

IR (KBr): 3359, 1673.9, 1648.8, 1257.4 cm$^{-1}$

NMR (DMSO-d$_6$, δ): 0.91 (3H, t, J=7.1 Hz), 0.96 (3H, d, J=6.7 Hz), 1.09 (3H, d, J=5.9 Hz), 1.3–1.5 (4H, m), 1.6–2.7 (9H, m), 3.19 (1H, m), 3.6–4.6 (15H, m), 4.7–5.3 (11H, m), 5.53 (1H, d, J=5.9 Hz), 6.73 (1H, d, J=8.3 Hz), 6.83 (1H, d, J=8.3 Hz), 6.88 (1H, s), 7.06 (1H, s), 7.14 (2H, d, J=8.9 Hz), 7.2–7.4 (3H, m), 7.90 (2H, d, J=8.9 Hz), 7.97 (4H, m), 8.08 (1H, d, J=6 Hz), 8.31 (1H, d, J=5 Hz), 8.76 (1H, d, J=5 Hz), 8.85 (1H, s), 8.86 (1H, s)

FAB-MASS: m/z=1325 (M+Na)$^+$

Analysis Calcd. for C$_{57}$H$_{70}$N$_{11}$O$_{22}$S$_2$Na.8H$_2$O: C, 45.87; H, 5.81; N, 10.32. Found C, 46.04; H, 5.77; N, 10.28.

EXAMPLE 26

IR (KBr): 3334, 1668.1, 1648.8, 1631.5 cm$^{-1}$

NMR (DMSO-d$_6$, δ): 0.97 (3H, d, J=6.6 Hz), 1.08 (3H, d, J=5.1 Hz), 1.36 (3H, t, J=6.9 Hz), 1.6–2.7 (7H, m), 3.17 (1H, m), 3.6–4.6 (15H, m), 4.7–5.3 (11H, m), 5.53 (1H, d, J=5.8 Hz), 6.73 (1H, d, J=8.2 Hz), 6.82 (1H, d, J=8.2 Hz), 6.87 (1H, s), 7.04 (1H, s), 7.06 (2H, d, J=8.7 Hz), 7.2–7.5 (3H, m), 7.73 (2H, d, J=8.7 Hz), 7.87 (2H, d, J=8.4 Hz), 7.8–8.2 (7H, m), 8.26 (1H, d, J=7.9 Hz), 8.75 (1H, d, J=7 Hz), 8.85 (1H, s), 8.92 (1H, s)

FAB-MASS: m/z=1358 (M+Na)$^+$

EXAMPLE 27

IR (KBr): 3355.5, 1666.2, 1631.5 cm$^{-1}$

NMR (DMSO-d$_6$, δ): 0.97 (3H, d, J=6.7 Hz), 1.09 (3H, d, J=5.6 Hz), 1.7–2.7 (7H, m), 3.18 (1H, m), 3.6–4.6 (13H, m), 4.7–5.3 (11H, m), 5.53 (1H, d, J=5.9 Hz), 6.73 (1H, d, J=8.2 Hz), 6.82 (1H, d, J=8.2 Hz), 6.86 (1H, s), 7.05 (1H, s), 7.2–7.6 (6H, m), 7.79 (2H, d, J=6.9 Hz), 7.9–8.2 (9H, m), 8.27 (1H, d, J=7.9 Hz), 8.76 (1H, d, J=7 Hz), 8.85 (1H, s), 8.93 (1H, s)

FAB-MASS: m/z=1314 (M−Na)$^+$

EXAMPLE 28

IR (KBr): 3357.5, 1648.8, 1631.5, 1261.2 cm$^{-1}$

NMR (DMSO-d$_6$, δ): 0.91 (3H, t, J=7.1 Hz), 0.96 (3H, d, J=8.1 Hz), 1.09 (3H, d, J=7.5 Hz), 1.3–1.5 (4H, m), 1.6–2.7 (9H, m), 3.19 (1H, m), 3.6–4.6 (15H, m), 4.7–5.3 (11H, m), 5.53 (1H, d, J=5.8 Hz), 6.73 (1H, d, J=8.3 Hz), 6.82 (1H, d, J=8.3 Hz), 6.85 (1H, s), 7.05 (1H, s), 7.19 (2H, d, J=9.0 Hz), 7.1–7.5 (3H, m), 7.9–8.2 (7H, m), 8.28 (1H, d, J=8.3 Hz), 8.85 (1H, s), 8.92 (1H, d, J=7.2 Hz)

FAB-MASS: m/z=1302 (M−Na)$^+$

Analysis Calcd. for C$_{56}$H$_{69}$ClN$_9$O$_{23}$SNa.7H$_2$O: C, 46.30; H, 5.76; N, 8.68. Found: C, 46.57; H, 5.67; N, 8.69.

EXAMPLE 29

IR (KBr): 3344.0, 1664.3, 1627.6 cm$^{-1}$

NMR (DMSO-d$_6$, δ): 0.86 (3H, t, J=6.5 Hz), 0.96 (3H, d, J=6.5 Hz), 1.04 (3H, d, J=5.6 Hz), 0.8–1.6 (14H, m), 1.7–2.6 (11H, m), 3.0–3.6 (9H, m), 3.6–4.5 (13H, m), 4.6–5.3 (11H, m), 5.45 (1H, d, J=6.0 Hz), 6.73 (1H, d, J=8.2 Hz), 6.82 (1H, d, J=8.2 Hz), 6.84 (1H, s), 7.02 (2H, d, J=8.6 Hz), 7.05 (1H, s), 7.2–7.5 (3H, m), 7.83 (2H, d, J=8.6 Hz), 8.08 (1H, d, J=8.8 Hz), 8.28 (1H, d, J=7.4 Hz), 8.47 (1H, d, J=6.4 Hz), 8.84 (1H, s)

FAB-MASS: m/z=1275 (M+Na)$^+$

Analysis Calcd: for C$_{57}$H$_{84}$N$_{10}$O$_{21}$S.9H$_2$O: C, 47.56; H, 7.14; N, 9.73. Found C, 47.73; H, 6.93; N, 9.68.

EXAMPLE 30

IR (KBr): 3361.3, 1668.1, 1631.5 cm$^{-1}$

NMR (DMSO-d$_6$, δ): 0.96 (3H, d, J=6.7 Hz), 1.06 (3H, d, J=5.8 Hz), 1.1–1.5 (6H, m), 1.5–2.1 (7H, m), 2.1–3.5 (18H, m), 3.5–4.5 (13H, m), 4.7–5.3 (11H, m), 5.50 (1H, d, J=5.9 Hz), 6.73 (1H, d, J=8.2 Hz), 6.82 (1H, d, J=8.2 Hz), 6.84 (1H, s), 6.85 (1H, d, J=8.1 Hz), 7.04 (1H, s), 7.06 (1H, d, J=8.1 Hz), 7.2–7.5 (5H, m), 7.83 (2H, d, J=8.1 Hz), 8.08 (1H, d, J=9.7 Hz), 8.28 (1H, d, J=8 Hz), 8.66 (1H, d, J=7.2 Hz), 8.85 (1H, s)

FAB-MASS: m/z=1309 (M+Na)$^+$

Analysis Calcd. for C$_{60}$H$_{82}$N$_{10}$O$_{21}$S.6H$_2$O C, 50.77; H, 6.67; N, 9.87. Found: C, 50.78; H, 6.82; N, 9.70.

The Starting Compound (31) in the following Example 31 and The Object Compound (31) in the following Example 31 are illustrated by chemical formulae as below.

The Starting Compound (31)

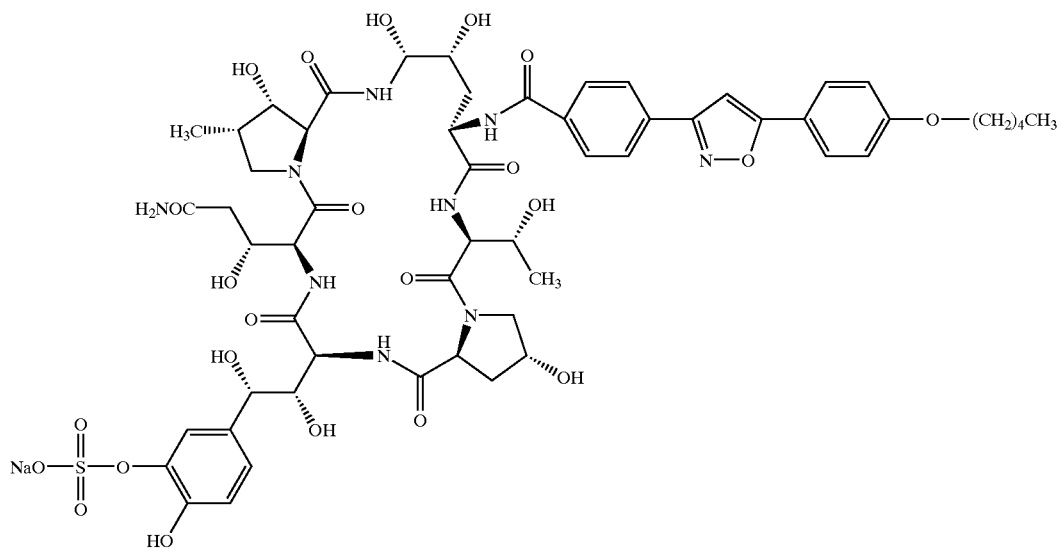

The Object Compound (31)

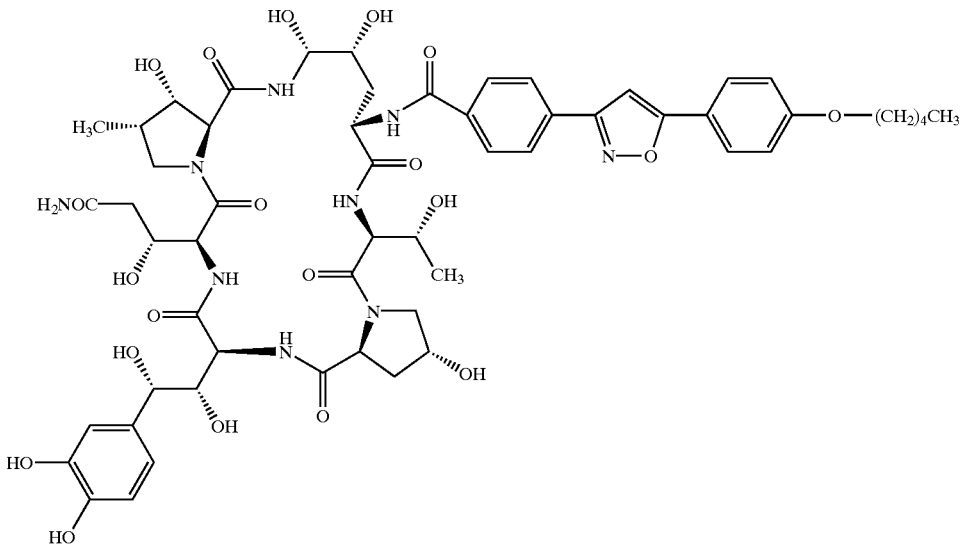

EXAMPLE 31

To a solution of Starting Compound (31) (5.2 g) in the mixture of tetrahydrofuran (105 ml), N,N-dimethylformamide (21 ml) and chlorotrimethylsilane (20.4 ml) was added triethylamine (33.6 ml) under ice-cooling and stirred for 12 hours at ambient temperature. The insoluble material was filtered off and the filtrate was evaporated under reduced pressure. The residue was purified by column chromatography on silica gel using n-hexane/ethyl acetate (4:1) as eluent. The fractions containing the object compound were combined and evaporated under reduced pressure. To the residue was added the mixture of acetic acid (10 ml) and methanol (30 ml) and stirred for 1 hour at ambient temperature. The reaction mixture was pulverized with diisopropyl ether. The precipitate was collected by filtration and dried over reduced pressure. The powder was added to 60% methanol in water and subjected to column chromatography on ODS (YMC-gel ODS-AM S-50) and eluted with 30% acetonitrile in water. The fractions containing the object compound were combined and evaporated under reduced pressure to remove acetonitrile. The residue was lyophilized to give Object Compound (31) (1.5 g).

IR (KBr): 3353.6, 1658.5, 1633.4, 1456.0 cm$^{-1}$

FAB-MASS: m/z=1211 (M+Na)$^+$

The Starting Compound (32) in the following Example 32 and the Object Compound (32) in the following Example 32 are illustrated by chemical formulae as below.

The Starting Compound (32)

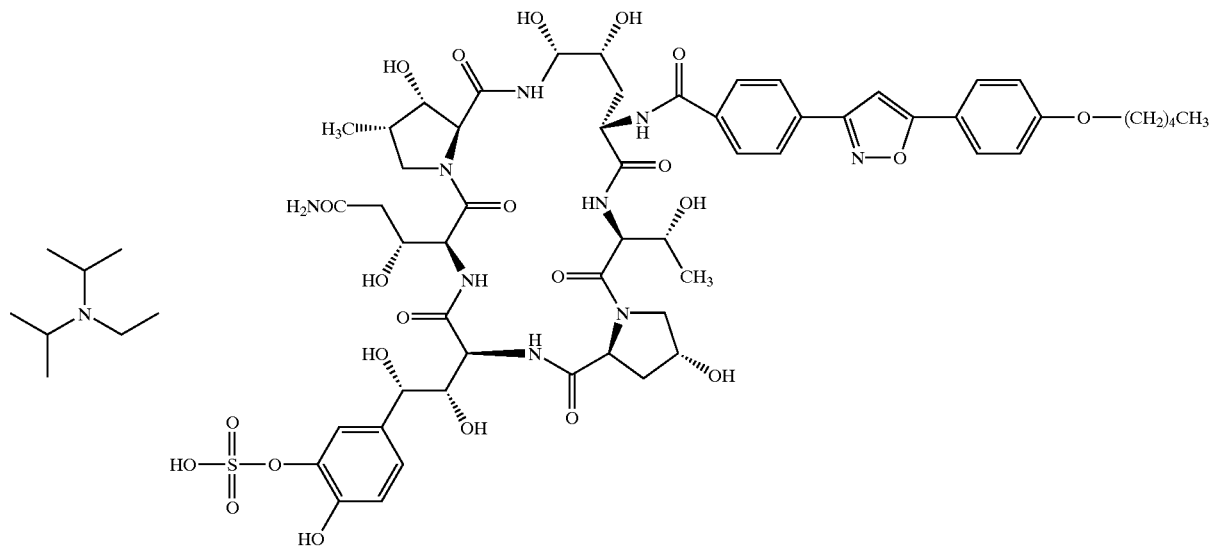

The Object Compound (32)

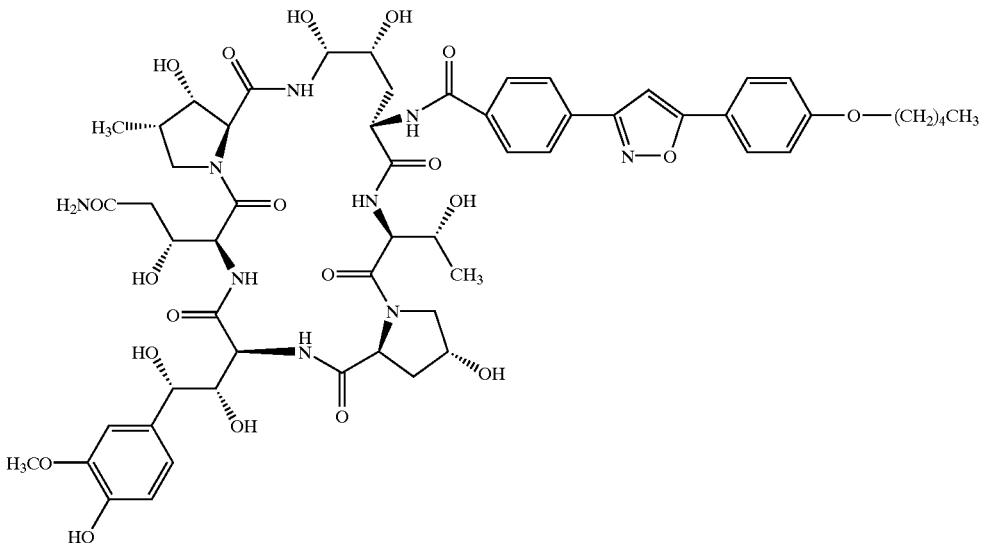

EXAMPLE 32

To a solution of Starting Compound (32) (10 g) in the mixture of tetrahydrofuran (200 ml), N,N-dimethylformamide (50 ml) and chlorotrimethylsilane (36.3 ml) was added triethylamine (59.8 ml) under ice-cooling and stirred for 12 hours at ambient temperature. The insoluble material was filtered off and the filtrate was evaporated under reduced pressure. The residue was purified by column chromatography on silica gel using n-hexane/ethyl acetate (4:1) as eluent. The fractions containing the object compound were combined and evaporated under reduced pressure. To a solution of the residue in the mixture of methanol (15 ml) and acetonitrile (15 ml) was added trimethylsilyl-diazomethane (2M solution in hexane, 0.98 ml) and diisopropylethylamine (0.343 ml) and stirred for 4 hours at ambient temperature. The reaction mixture was added to saturated sodium bicarbonate aqueous solution and extracted with ethyl acetate. The organic layer was dried over magnesium sulfate. Magnesium sulfate was filtered off, and the filtrate was evaporated under reduced pressure. To a solution of the residue in tetrahydrofuran (30 ml) was added the mixture of acetic acid (3.76 ml) and tetra-n-butylammonium fluoride (1M solution in tetrahydrofuran, 65.6 ml) and stirred for 2 hours under ice-cooling. The reaction mixture was pulverized with water. The precipitate was collected by filtration and dried over reduced pressure. The powder was purified by column chromatography on silica gel using dichloromethane/acetic acid/methanol/water (4:1:1:1) as eluent. The fractions containing the object compound were combined and evaporated under reduced pressure to give Object Compound (32) (280 mg).

NMR (DMSO-$d_6$, δ): 0.91 (3H, t, J=7.0 Hz), 0.96 (3H, d, J=6.5 Hz), 1.09 (3H, d, J=5.7 Hz), 1.3–1.5 (4H, m), 1.6–2.7 (9H, m), 3.16 (1H, m), 3.75 (3H, s), 3.9–4.6 (15H, m), 4.7–5.3 (11H, m), 5.54 (1H, d, J=5.8 Hz), 6.6–6.8 (3H, m), 6.87 (1H, s), 7.12 (2H, d, J=8.9 Hz), 7.2–7.5 (3H, m), 7.55 (1H, s), 7.85 (2H, d, J=8.9 Hz), 7.9–8.1 (5H, m), 8.29 (1H, d, J=7.7 Hz), 8.86 (1H, s), 8.85 (1H, s), 8.71 (1H, d, J=7 Hz)

FAB-MASS: m/z=1226 (M+Na)$^+$

---

What is claimed is:

1. A polypeptide compound of the following general formula

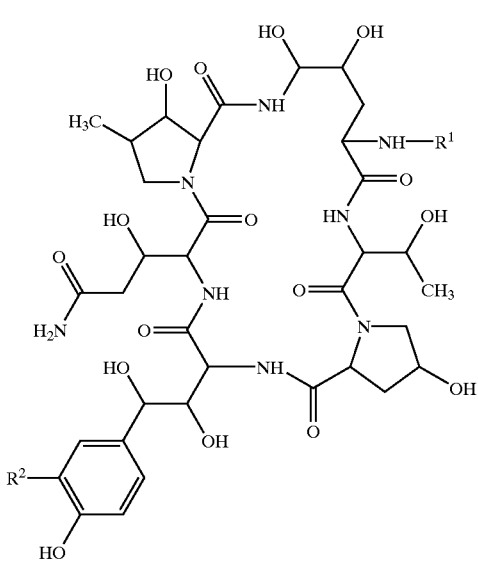

[I]

wherein $R^1$ is one member selected from the group consisting of benzoyl substituted with piperazinyl substituted with piperidyl substituted with cyclo(lower)alkyl, benzoyl substituted with piperazinyl substituted with piperidyl having higher alkyl, benzoyl substituted with piperazinyl substituted with cyclo(lower)alkyl having lower alkyl, benzoyl substituted with piperidyl having phenyl having cyclo(lower)alkyloxy benzoyl substituted with piperidyl having phenyl having morpholinyl, benzoyl substituted with piperidyl having phenyl having phenyl(lower)alkoxy, benzoyl substituted with piperidyl having piperidyl having higher alkyl, benzoyl substituted with piperidyl having phenyl (lower)alkyl having lower alkoxy, benzoyl substituted with piperidyl having cyclo(lower)alkyl, benzoyl substituted with piperidyl having cyclo(lower)alkyl having cyclo(lower)alkyl, benzoyl substituted with piperidyl having cyclo(lower)alkyl having lower alkyl, benzoyl substituted with piperidyl having hydroxy, benzoyl substituted with piperidyl having hydroxy and phenyl having lower alkoxy, beuzoyl substituted with piperidyl having phenyl having lower alkoxy, benzoyl substituted with thiadiazolyl having phenyl having methoxy, benzoyl substituted with 1,2,3,6-tetrahydropyridyl, benzoyl substituted with 1,2,3,6-tetrahydropyridyl having phenyl having lower alkoxy, benzoyl substituted with thienyl, benzoyl substituted with thienyl having phenyl having lower alkoxy, benzoyl substituted with furyl, benzoyl substituted with furyl having phenyl having lower alkoxy, benzoyl substituted with piperazinyl(lower)alkyl, benzoyl substituted with phenyl(lower)alkynyl, benzoyl substituted with phenyl (lower)alkynyl having phenyl having lower alkoxy, lower alkanoyl substituted with thiazolyl, lower alkanoyl substituted with thiazolyl having phenyl having phenyl substituted with lower alkoxy, benzoyl substituted with imidazothiazolyl, benzoyl substituted with imidazotbiazolyl having phenyl having lower alkoxy, benzoyl substituted with imidazothiazolyl having phenyl having phenyl substituted with lower alkoxy, benzoyl substituted with imidazothiazolyl having phenyl having phenyl, benzoyl substituted with isoxazolyl having halogen, benzoyl substituted with isoxazolyl having halogen having phenyl having lower alkyl, and 4-[5-(4-pentyloxyphenyl)isoxazol-3-yl] benzoyl; and $R^2$ is hydroxy, hydroxysulfonyloxy, or lower alkoxy, with the proviso that $R^2$ is not hydroxysulfonyloxy when $R^1$ is 4-[5-(4-pentyloxyphenyl)isoxazol-3-yl]benzoyl, and a salt thereof.

2. A polypeptide compound of the following general formula [I]:

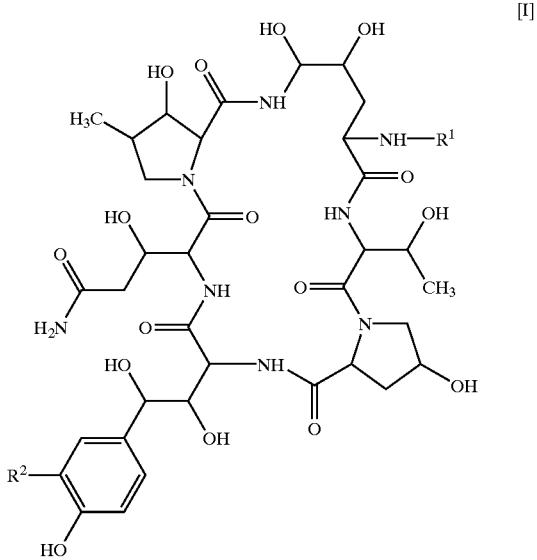

[I]

wherein

R¹ is 4-[5-(4-pentyloxyphenyl)isoxazol-3yl]benzoyl, and
R² is hydroxy or lower alkoxy.

3. The compound of claim 1, wherein
R¹ is benzoyl substituted with piperazinyl substituted with piperidyl having higher alkyl or benzoyl substituted with piperazinyl substituted with cyclo(lower)alkyl.

4. The compound of claim 1, wherein R¹ is benzoyl substituted with piperidyl having phenyl having cyclo(lower)alkyloxy, benzoyl substituted with piperidyl having phenyl having morpholinyl, beuzoyl substituted with piperidyl having phenyl having phenyl(lower)alkoxy, benzoyl substituted with piperidyl having piperidyl having higher alkyl, benzoyl substituted with piperidyl having phenyl (lower)alkyl having lower alkoxy, benzoyl substituted with piperidyl having cyclo(lower)alkyl, benzoyl substituted with piperidyl having cyclo(lower)alkyl having cyclo(lower)alkyl, or benzoyl substituted with piperidyl having cyclo(lower)alkyl having lower alkyl.

5. The compound of claim 1, wherein R¹ is benzoyl substituted with piperidyl having hydroxy or benzoyl substituted with piperidyl having hydroxy and phenyl having lower alkoxy.

6. The compound of claim 1, wherein R¹ is benzoyl substituted with piperidyl having phenyl having lower alkoxy.

7. The compound of claim 1, wherein R¹ is benzoyl substituted with thiadiazolyl having phenyl having methoxy.

8. The compound of claim 1, wherein R¹ is benzoyl substituted with 1,2,3,6-tetrahydropyridyl or benzoyl substituted with 1,2,3,6-tetrahydropyridyl having phenyl having lower alkoxy.

9. The compound of claim 1, wherein R¹ is benzoyl substituted with thienyl or benzoyl substituted with thienyl having phenyl having lower alkoxy.

10. The compound of claim 1, wherein R¹ is benzoyl substituted with furyl or benzoyl substituted with furyl having phenyl having lower alkoxy.

11. The compound of claim 1, wherein R¹ is benzoyl substituted with piperazinyl(lower)alkyl.

12. The compound of claim 1, wherein R¹ is benzoyl substituted with phenyl(lower)alkynyl or benzoyl substituted with phenyl(lower)alkynyl having phenyl having lower alkoxy.

13. The compound of claim 1, wherein R¹ is lower alkanoyl substituted with thiazolyl or lower alkanoyl substituted with thiazolyl having phenyl having phenyl substituted with lower alkoxy.

14. The compound of claim 1, wherein R¹ is benzoyl substituted with imidazothiazolyl, benzoyl substituted with imidazothiazolyl having phenyl having lower alkoxy, benzoyl substituted with imidazothiazolyl having phenyl having phenyl substituted with lower alkoxy, or benzoyl substituted with imidazothiazolyl having phenyl having phenyl.

15. The compound of claim 1, wherein R¹ is benzoyl substituted with isoxazolyl having halogen or benzoyl substituted with isoxazolyl having halogen having phenyl having lower alkyl.

16. A process for the preparing a polypeptide compound [I] of claim 1, which comprises 1) reacting a compound of the formula:

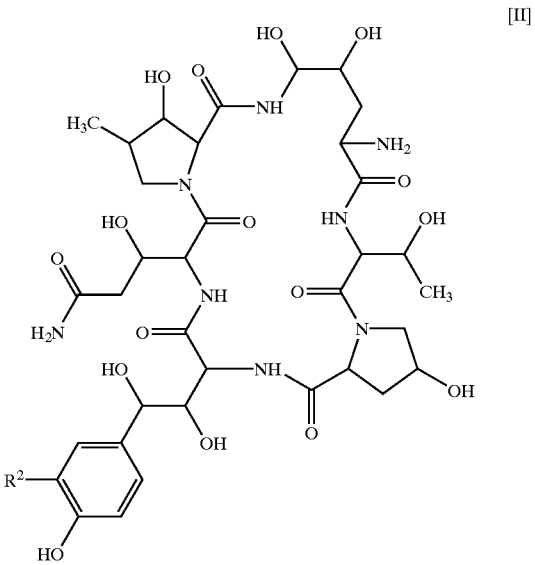

[II]

or its reactive derivative at the amino group or a salt thereof, with a compound of the formula:

R¹—OH [III]

wherein R¹ and R² are defined in claim 1, or its reactive derivative at the carboxy group or a salt thereof, to give a compound [I] or the formula:

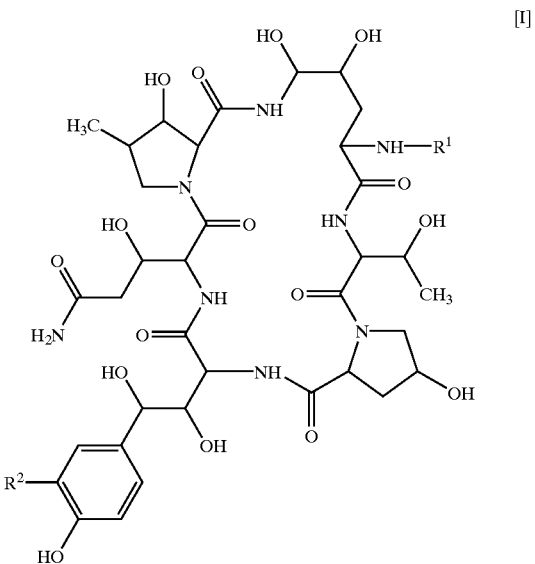

[I]

wherein R¹ and R² are defined in claim 1, or a salt thereof, or 2) subjecting a compound [Ia] of the formula:

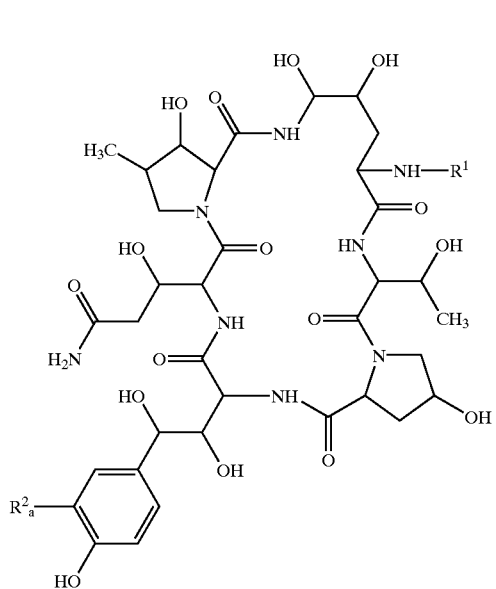

wherein $R^1$ is defined in claim 1, $R^2$ is hydroxysulfonyloxy or a salt thereof, to hydrolysis reaction of the sulfonic acid group, to give a compound [Ib] of the formula:

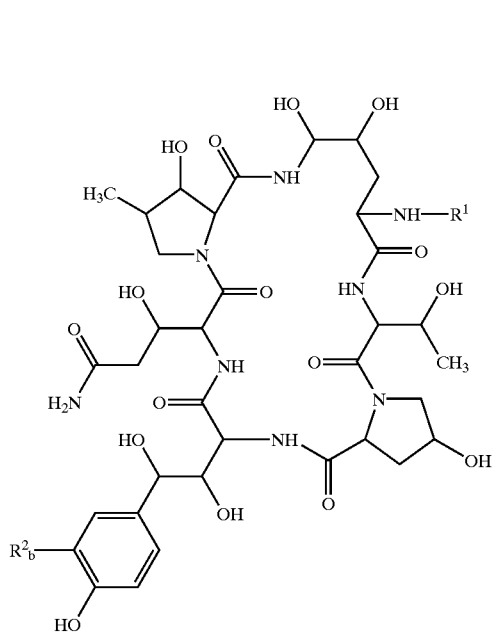

wherein $R^1$ is defined in claim 1, $R_b^2$ is hydroxy or a salt thereof, or 3) subjecting a compound [Ib] of the formula:

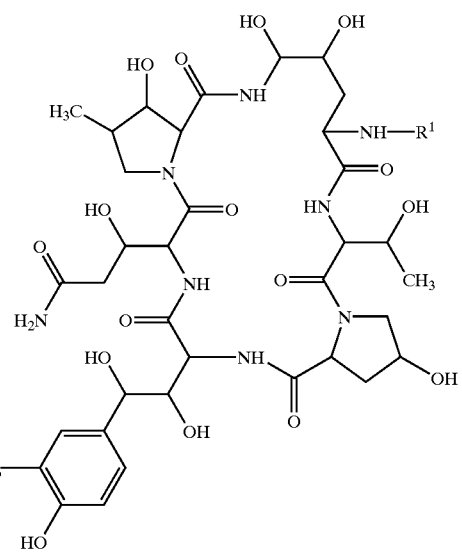

wherein $R^1$ is defined in claim 1, $R_b^2$ is hydroxy or its reactive derivative at the hydroxy group or a salt thereof, to alkylation reaction of the hydroxy group, to give a compound [Ic] of the formula:

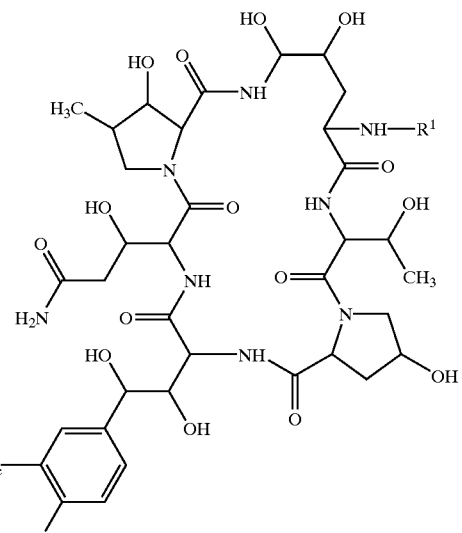

wherein $R^1$ is defined in claim 1, $R_c^2$ is lower alkoxy or a salt thereof.

17. A method for treating infectious diseases caused by pathogenic microorganisms comprising administering the compound of claim 1, or a pharmaceutically acceptable salt thereof in an amount effective to treat the infectious disease to a human or animal.

18. The method of Claim 17, wherein said pathogenic microorganism is of a genus selected from the group consisting of Aspergillus, Cryptococcus, Candida, Mucor, Actinomyces, Histoplasma, Dermatophyte, Malassezia, and Fusarium.

19. The method of claim 17, wherein said pathogenic microorganism is *Pneumocystis carinii*.

20. A composition comprising the polypeptide compound of claim 1 or a salt thereof; and a carrier.

21. A composition comprising the polypeptide compound of claim 2 or a salt thereof; and a carrier.

22. A composition comprising the polypeptide compound of claim 3 or a salt thereof; and a carrier.

23. A composition comprising the polypeptide compound of claim 4 or a salt thereof; and a carrier.

24. A composition comprising the polypeptide compound of claim 5 or a salt thereof; and a carrier.

25. A composition comprising the polypeptide compound of claim 6 or a salt thereof; and a carrier.

26. A composition comprising the polypeptide compound of claim 7 or a salt thereof; and a carrier.

27. A composition comprising the polypeptide compound of claim 8 or a salt thereof; and a carrier.

28. A composition comprising the polypeptide compound of claim 9 or a salt thereof; and a carrier.

29. A composition comprising the polypeptide compound of claim 10 or a salt thereof; and a carrier.

30. A composition comprising the polypeptide compound of claim 11 or a salt thereof; and a carrier.

31. A composition comprising the polypeptide compound of claim 12 or a salt thereof; and a carrier.

32. A composition comprising the polypeptide compound of claim 13 or a salt thereof; and a carrier.

33. A composition comprising the polypeptide compound of claim 14 or a salt thereof; and a carrier.

34. A composition comprising the polypeptide compound of claim 15 or a salt thereof; and a carrier.

* * * * *

SEQUENCE LISTING

<160> NUMBER OF SEQ ID NOS: 1

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence:peptide
<221> NAME/KEY: MOD_RES
<222> LOCATION: (1)
<223> OTHER INFORMATION: 4-hydroxy
<221> NAME/KEY: MOD_RES
<222> LOCATION: (2)
<223> OTHER INFORMATION: hydroxy, substituted phenyl
<221> NAME/KEY: MOD_RES
<222> LOCATION: (3)
<223> OTHER INFORMATION: hydroxy substituted

```
<221> NAME/KEY: MOD_RES
<222> LOCATION: (4)
<223> OTHER INFORMATION: 3-hydroxy, 4-methyl proline
<221> NAME/KEY: MOD_RES
<222> LOCATION: (5)
<223> OTHER INFORMATION: hydroxy subtituted
<221> NAME/KEY: MOD_RES
<222> LOCATION: (6)
<223> OTHER INFORMATION: hydroxy ethyl substituted
<223> OTHER INFORMATION: Glycine at position 6 is linked to Proline at
      position 1 by a peptide linkage

<400> SEQUENCE: 1

Pro Thr Gln Pro Gln Gly
  1               5
```